US008207365B2

(12) United States Patent
Zheng et al.

(10) Patent No.: US 8,207,365 B2
(45) Date of Patent: Jun. 26, 2012

(54) POLYMERIC SALEN COMPOUNDS AND METHODS THEREOF

(75) Inventors: Xiaolai Zheng, Atlanta, GA (US); Michael Johannes Holbach, Oberursel (DE); Marcus Weck, New York, NY (US); Christopher W. Jones, Mableton, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1098 days.

(21) Appl. No.: 11/908,192

(22) PCT Filed: Mar. 13, 2006

(86) PCT No.: PCT/US2006/008634
§ 371 (c)(1),
(2), (4) Date: Apr. 24, 2008

(87) PCT Pub. No.: WO2006/099162
PCT Pub. Date: Sep. 21, 2006

(65) Prior Publication Data
US 2009/0030172 A1    Jan. 29, 2009

Related U.S. Application Data

(60) Provisional application No. 60/661,549, filed on Mar. 14, 2005, provisional application No. 60/661,550, filed on Mar. 14, 2005, provisional application No. 60/710,269, filed on Aug. 22, 2005.

(51) Int. Cl.
*C09B 55/00* (2006.01)
*C07C 69/00* (2006.01)
*C07C 67/00* (2006.01)

(52) U.S. Cl. ............. 556/33; 556/34; 560/130; 560/131

(58) Field of Classification Search ........................ None
See application file for complete search history.

(56) References Cited

U.S. PATENT DOCUMENTS

| 5,663,393 | A | 9/1997 | Jacobsen et al. |
| 6,262,278 | B1 | 7/2001 | Jacobsen et al. |
| 6,884,750 | B2 | 4/2005 | Kim et al. |
| 2006/0149089 | A1 | 7/2006 | Malfroy-Camine et al. |

OTHER PUBLICATIONS

Holbach et al. (Modular Approach for the Development of Supported, Monofunctionalized, Salen Catalysts, J. Org. Chem. Feb. 2006, 71(5), pp. 1825-36).*
T. Reger et al, Polymer-Supported (Salen) Mn Catalysts for Asymmetric Epoxidation: A Comparison between Soluble and Insoluble Matrices, J. Am. Chem. Soc. 2000, 122, 6929-6934.
M. Angelino et al, Polymer-Supported Salen Complexes for Heterogeneous Asymmetric Synthesis: Stability and Selectivity, Journal of Polymer Science. vol. 37, 3888-3898 (1999).

L. Canali et al, Polystyrene and polymethacrylate resin-supported Jacobsen's alkene epoxidation catalyst, J. Chem. Soc., Perkin Trans. 1, 2000, 2055-2066.
F. Bigi et al, Heterogeneous enantioselective epoxidation of olefins catalysed by unsymmetrical (salen) Mn(III) complexes supported on amorphous or MCM-41 silica through a new triazine-based linker, Chem. Commun.. 2002, 716-717.
D. Park et al, Asymmetric epoxidation of styrene on the heterogenized chiral salen complexes prepared from organo-functionalized mesoporous materials, Catalysts Letters, vol. 78, Nos. 1-4, Mar. 2002, 145-151.
A. Heckel et al, Enantioselective Heterogeneous Epoxidation and Hetero-Diels-Alder Reaction with Mn- and Cr-salen Complexes Immobilized on Silica Gel by Radical Grafting, Helvetica Chimica Acta, vol. 85 (2002), 913-925.
H. Sellner, Preparation of Dendritic and Non-Dendritic Styryl-Substituted Salens for Cross-Linking Suspension Copolymerization with Styreme and Multiple Use of the Corresponding Mn and Cr Complexes in Enantioselective Epoxidations and Hetero-Diels-Alder Reactions, Chem. Eur. J. 2001, 7, No. 13, 2873-2887.
F. Minutolo et al, Heterogeneous Asymmetric Epoxidation of Unfunctionalized Olefins Catalyzed by Polymer-Bound (Salen) manganese Complexes, Tetrahedron: Asymmetry, vol. 7, No. 8, pp. 2293-2302, 1996.
M. Holbach et al, Modular Approach for the Development of Supported, Monofunctionalized, Salen Catalysts, J. Org. Chem. 2006, 71, 1825-1836.
X. Zheng et al, Poly(styrene)-Supported Co-Salen Complexes as Efficient Recyclable Catalysts for the Hydrolytic Kinetic Resolution of Epichlorohydrin, Chem. Eur. J. 2006, 12, 576-583.
R. Breinbauer et al, Cooperative Asymmetric Catalysis with Dendrimeric [Co(salen)] Complexes, Angew. Chem. Int. Ed. 2000, 39, No. 20.
J. Ready et al, A Practical Oligomeric [(salen)Co] Catalyst for Asymmetric Epoxide Ring-Opening Reactions, Angew. Chem. Int. Ed. 2002, 41, No. 8.
J. Ready et al, Highly Active Oligomeric (salen) Co Catalysts for Asymmetric Epoxide Ring-Opening Reactions, J. Am. Chem. Soc. 2001, 123, 2687-2688.

(Continued)

*Primary Examiner* — Alton Pryor
(74) *Attorney, Agent, or Firm* — Merchant & Gould

(57) ABSTRACT

The present disclosure provides a polymerizable compound of the formula (I)

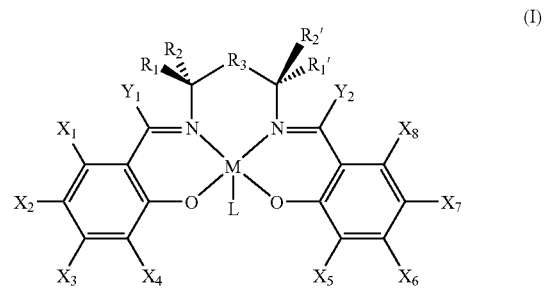

(I)

where the $R_1$, $R_2$, $R'_1$, $R'_2$, $X_1$ to $X_8$, $Y_1$, $Y_2$, M and L have any of values as defined in the specification. The disclosure also provides an oligomer, a homo-polymer, or a co-polymer of compound of the formula (I). The disclosure also provides methods for preparing the compound of the formula (I) and methods for preparing polymers of the compound of the formula (I), and to methods and intermediates useful for preparing them. The disclosure also provides methods for the use of the polymers of formula (I) as chiral catalysts in enantioselective preparative processes.

14 Claims, No Drawings

OTHER PUBLICATIONS

S. Schaus et al, Highly Selective Hydrolytic Kinetic Resolution of Terminal Epoxides Catalyzed by Chiral (salen) CoIII Complexes, Practical Synthesis of Enantioenriched Terminal Epoxides and 1,2-Diols, J. Am. Chem. Soc., vol. 124, No. 7, 2002.

L. Nielsen et al, Mechanistic Investigation Leads to a Synthetic Improvement in the Hydrolytic Kinetic Resolution of Terminal Epoxides, J. Am. Chem. Soc. 2004, 126, 1360-1362.

M. Tokunaga et al, Asymmetric Catalysts with Water: Efficient Kinetic Resolution of Terminal Epoxides by Means of Catalytic Hydrolysis, Science 277, 936 (1997).

D. White et al, New oligomeric catalyst for the hydrolytic kinetic resolution of terminal epoxides under solvent-free conditions, Science Direct, Tetrahedron: Asymmetry 14 (2003) 3633-3638.

* cited by examiner

POLYMERIC SALEN COMPOUNDS AND METHODS THEREOF

This application is a 35 USC 371 national stage patent application derived from PCT International Patent Application No. PCT/US2006/008634 filed on 13 Mar. 2006, in the name of Georgia Tech Research Corporation, a U.S. national corporation, applicant for the designation of all countries except the U.S., and Xiaolai Zheng, citizen of China P. R., Michael Johannes Holbach and Marcus Weck, both German citizens, and Christopher W. Jones, a U.S. citizen; applicants for the designation of the U.S. only, and claims priority to U.S. Applications Ser. Nos. 60/661,549, filed 14 Mar. 2005, 60/661,550, filed 14 Mar. 2005 and 60/710,269, filed 22 Aug. 2005.

BACKGROUND

Methods for making and using chiral catalyst for use in stereoselective chemical reaction processes are known, see for example, U.S. Pat. Nos. 5,663,393 and 6,262,278, to Jacobsen, et al., and U.S. Pat. No. 6,884,750, to Kim et al. Supported chiral catalysts are also known, see for example, Reger, T. S., et al., *J. Am. Chem. Soc.*, 2000, 122, 6929.

Challenges associated with supported chiral catalyst compositions and their use can include, for example, difficult separation from product, non-reuse or poor reuse (reusability) performance, low or reduced activity, and low or reduced selectivity. These and other challenges can prohibit broad industrial application or at least contribute to a higher total cost of manufacture and use of chiral catalyst compositions and to higher total cost of manufacture of chemical products produced therewith.

There is a need for improved supported chiral catalyst compositions and to improved methods for making and using the compositions.

SUMMARY

In general terms, the claimed invention relates to certain transition metal salen complexes, polymers thereof, and use of the polymers as catalysts, for example, in preparing organic compounds having high optical purity, such as in asymmetric epoxidation or hydrolytic kinetic resolution processes.

One possible aspect of the disclosure is a polymerizable compound of the formula (I)

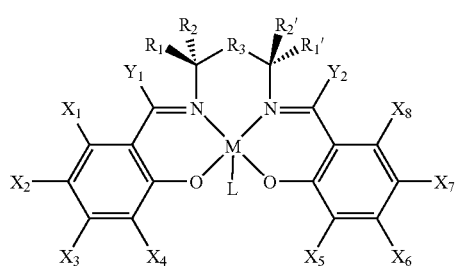

wherein $R_1$, $R_2$, $R'_1$, $R'_2$, $X_1$, $X_2$, $X_3$, $X_4$, $X_5$, $X_6$, $X_7$, $X_8$, $Y_1$ and $Y_2$ are independently H, $C_1$-$C_6$ alkyl, $C_{3-12}$ cycloalkyl, $C_1$-$C_6$ alkoxy, halogen, —OH, —SH, —$NO_2$, —$NH_2$, amino, imine, amide, carbonyl, carboxy, silyl, ether, thio ether, seleno ether, ketone, aldehyde, ester, phosphoryl, phosphonate, phosphine, sulfonyl, or —$(CH_2)_k$—$R_4$ group, wherein $R_4$ is aryl, heteroaryl, cycloalkyl, heterocycle, or polycycle, and k is an integer of 0 to 8, or any two or more proximate $R_1$, $R_2$, $R'_1$, $R'_2$, $X_1$, $X_2$, $X_3$, $X_4$, $X_5$, $X_6$, $X_7$, $X_8$, $Y_1$ and $Y_2$ form a ring of a carbocycle or heterocycle comprising 4 to 10 atoms, where at least one $X_1$, $X_2$, $X_3$, $X_4$, $X_5$, $X_6$, $X_7$, $X_8$, $Y_1$ and $Y_2$ is independently of the formula -L'-Z-P, where L' is a divalent linker which is independently a single carbon-carbon bond, —$(CH_2)_k$—$R_5$—, —$(CH=CH)_k$—$R_5$—, or —$(C≡C)_k$—$R_5$—, wherein —$R_5$— is arylene, heteroarylene, cycloalkylene, heterocyclene, or polycyclene, and k is an integer of 0 to 8, —$R_5$— can optionally be further substituted, Z is a divalent connector which is independently a single carbon-carbon bond, —C(=O)—, —C(=S)—, —C(=S)S—, —SC(=S)—, —$SO_2$—, —S(=O)$_2$O—, —O—S(=O)$_2$—, —C(=O)N($R_a$)—, —C(=S)N($R_a$)—, —$SO_2$N($R_a$)—, —C(=O)O—, —O—C(=O)—, —C(=S)O—, $C_1$-$C_8$ alkylenyl, or alkyl substituted $C_1$-$C_8$ alkylenyl, where $R_a$ is —H, alkyl, acyl, aryl, alkylaryl, arylalkyl, aryloxy, alkoxylcarbonyl, or benzyloxycarbonyl, and P is a polymerizable group which is independently $C_2$-$C_6$ alkenyl, $C_2$-$C_6$ alkynyl, arylene-$C_2$-$C_6$ alkenyl, cycloalkenyl, cycloalkynyl, heterocycloalkenyl, or polycycloalkenyl;

$R_3$ is independently which is a single carbon-carbon bond, —$CH_2$—, —$CH_2CH_2$—, —NH—, —O—, or —S—;

M is absent or a metal atom or ion of at least one of Co, Mn, Cr, Al, Zn, Ru, Fe, Mo, Ni, Ti, Zr, or mixtures thereof; and L is absent, or a counter anion selected from F, Cl, Br, I, —O(C=O)alkyl, —O—S(=O)$_2$—R'$_4$, wherein R'$_4$ is aryl, aryl$C_2$-$C_6$ alkyl, heteroaryl, $C_1$-$C_6$ alkyl, cycloalkyl, heterocycle, $PF_6$, $B(Ar)_4$, or $B(halo)_4$, where halo is F, Cl, Br, or I; or a salt or hydrate thereof.

Another possible aspect of the disclosure is a polymerizable compound of the formula (I) wherein only one $X_1$, $X_2$, $X_3$, $X_4$, $X_5$, $X_6$, $X_7$, $X_8$, $Y_1$ and $Y_2$ is independently of the formula -L'-Z-P, that is, a single polymerizable group of the formula -L'-Z-P.

Another possible aspect of the disclosure is a polymer of the compound of the formula (I) wherein only one of the substituents $X_1$, $X_2$, $X_3$, $X_4$, $X_5$, $X_6$, $X_7$, $X_8$, $Y_1$ and $Y_2$ is of the formula -L'-Z-P, that is, each compound of formula (I) has a single polymerized group of the formula -L'-Z-(P)<.

Another possible aspect of the disclosure is a polymer of the compound of formula (I), such as an oligomer or homopolymer of formula (I), or an oligomer or a copolymer of formula (I) with other polymerizable monomers.

Another possible aspect of the disclosure is a preparative method for a homo-polymer of the compound of formula (I).

Another possible aspect of the disclosure is a preparative method for a co-polymer of the compound of formula (I).

Another possible aspect of the disclosure is a preparative method for an oligomeric-ring or macrocyclic-ring polymer of the compound of formula (I).

Another possible aspect of the disclosure is a preparative method for novel intermediates useful for preparing a compound of formula (I) and its polymers.

Another possible aspect of the disclosure is a catalytic preparative method, comprising reacting a suitable substrate molecule with a polymer of the compound of formula (I) to form a reaction product of the substrate molecule having high enantiomeric excess.

Another possible aspect of the disclosure is a supported compound of formula (I).

Another possible aspect of the disclosure is a supported polymer of the compound of formula (I), such as an oligomer, a homopolymer, or a copolymer of formula (I).

DETAILED DESCRIPTION

Various embodiments of the present disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Definitions

Unless otherwise stated, the following terms used in the specification and claims have the meanings given below.

In various embodiments, halo includes fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

"Acyl" refers to a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cyclohexylcarbonyl, cyclohexylmethylcarbonyl, benzoyl, benzylcarbonyl, and the like.

"Acylalkyl" refers to a radical -alkylene-C(O)R where R is hydrogen, alkyl, haloalkyl, cycloalkyl, cycloalkyl-alkyl, optionally substituted phenyl, benzyl, hydroxy, alkoxy, amino, monoalkylamino or dialkylamino Representative examples include methylcarbonyl-methyl, 2-(ethoxycarbonyl)ethyl, 2-(methoxycarbonyl)ethyl, 2-carboxyethyl, and like radicals.

"Acylamino" or refers to an amide radical —NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethylcarbonylamino, benzoylamino, benzylcarbonylamino, and like radicals.

"Alkoxy" refers to a radical —OR where R is an alkyl as defined herein, e.g., methoxy, ethoxy, propoxy, butoxy, and like radicals. Similarly, "alkenyloxy" refers to a radical —OR where R is instead an alkenyl as defined herein, e.g., ethenyloxy, propenyloxy, butenyloxy, and like radicals.

"Alkoxycarbonyl" refers to a radical —C(O)—R where R is alkoxy is as defined herein.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and like radicals.

"Alkyl" refers to a linear saturated monovalent hydrocarbon radical of one to ten carbon atoms or a branched saturated monovalent hydrocarbon radical of three to six carbon atoms, e.g., methyl, ethyl, propyl, 2-propyl, n-butyl, iso-butyl, tert-butyl, pentyl, and like radicals. "Alkyl" includes linear alkyls, branched alkyls, and cycloalkyls.

"Alkylamino" or "monoalkylamino" refers to a radical —NHR where R represents an alkyl, cycloalkyl or cycloalkyl-alkyl group as defined herein. Representative examples include, but are not limited to methylamino, ethylamino, isopropylamino, cyclohexylamino, and like radicals.

"Alkylene" refers to a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and like radicals.

"Alkynyl" refers to a linear monovalent hydrocarbon radical of two to six carbon atoms or a branched monovalent hydrocarbon radical of three to six carbon atoms, containing at least one triple bond, e.g., ethynyl, propynyl, and like radicals.

"Alkylsulfonyl" refers to a radical —S(O)$_2$R where R is an alkyl, cycloalkyl or cycloalkyl-alkyl group as defined herein, e.g., methylsulfonyl, ethylsulfonyl, propylsulfonyl, butylsulfonyl, cyclohexylsulfonyl, and like radicals.

"Alkylsulfinyl" refers to a radical —S(O)R where R is an alkyl, cycloalkyl or cycloalkylalkyl group as defined herein, e.g., methylsulfinyl, ethylsulfinyl, propylsulfinyl, butylsulfinyl, cyclohexylsulfinyl, and like radicals.

"Alkylthio" refers to a radical —SR where R is an alkyl as defined above, e.g., methylthio, ethylthio, propylthio, butylthio, and like radicals.

"Aryl" refers to a monocyclic, bicyclic, or polycyclic aromatic hydrocarbon radical which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term aryl includes, but is not limited to, phenyl, chlorophenyl, fluorophenyl, methoxyphenyl, 1-naphthyl, 2-naphthyl, and like radicals, and derivatives thereof "Aryl" includes a phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkylene, alkoxy, halo, and like substituents.

"Arylene" refers to a divalent aryl group as defined above, e.g., 1,4-phenylene-(1,4-Ph-), 1,4-arylene-C$_2$-C$_6$ alkenyl such as —Ar—CH═CH$_2$, and like radical "Arylalkyl" refers to an alkyl radical as defined herein in which one of the hydrogen atoms of the alkyl group is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl, and like radicals.

"Aryloxy" refers to a radical —O—R where R is an aryl group as defined herein.

"Cycloalkyl" refers to a saturated monovalent cyclic hydrocarbon radical of three to seven ring carbons e.g., cyclopropyl, cyclobutyl, cyclohexyl, 4-methylcyclohexyl, and like radicals.

"Cycloalkylene" refers to a divalent saturated monovalent cyclic hydrocarbon radical as defined above.

"Cycloalkenyl" refers to an unsaturated monovalent cyclic hydrocarbon radical of three to ten ring carbons and containing at least one double bond, e.g., cyclopropylene, cyclobutylene, cyclohexylene, 4-methylcyclohexylene, cyclooctene, and like radicals.

"Cycloalkyl-alkyl" refers to a radical —R$^x$R$^y$ where R$^x$ is an alkylene group and R$^y$ is cycloalkyl group as defined herein, e.g., cyclohexylmethyl, and like radicals.

"Dialkylamino" refers to a radical —NRR' where R and R' independently represent an alkyl, cycloalkyl, or cycloalkylalkyl group as defined herein. Representative examples include, but are not limited to dimethylamino, methylethylamino, di(1-methylethyl)amino, (cyclohexyl)(methyl) amino, (cyclohexylmethyl)(methyl)amino, and like radicals.

"Haloalkyl" refers to alkyl substituted with one or more same or different halo atoms, e.g., —CH$_2$Cl, —CF$_3$, —CH$_2$CF$_3$, —CH$_2$CCl$_3$, and like radicals.

"Het" includes a four- (4), five- (5), six- (6), seven- (7), or eight- (8) membered saturated or unsaturated heterocyclic ring having 1, 2, 3, or 4 heteroatoms of the group oxy, thio, sulfinyl, sulfonyl, silyl, or nitrogen, which ring is optionally fused to a benzene ring. Het also includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, (C$_{1-4}$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. "Heteroaryl" refers to a monocyclic or bicyclic radical of 5 to 12 ring atoms having at least one aromatic ring containing one, two, or three ring heteroatoms such as N, O, or S, the remaining ring atoms being C, with the understanding that the attachment point of the heteroaryl radical will be on an aromatic ring. The heteroaryl ring can be optionally substituted independently with one or more substituents, preferably one or two substituents, such as alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy, ethylenedioxy, or optionally substituted phenyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, tetrahydropyranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl, benzothienyl, and like radicals, or derivatives thereof.

"Heterocyclyl" or "heterocycle" refers to a saturated or unsaturated non-aromatic cyclic radical of 3 to 8 ring atoms in which one or two ring atoms can be a heteroatom, such as NR$^x$ {wherein each R$^x$ is independently hydrogen, alkyl, acyl, alkylsulfonyl, aminosulfonyl, (alkylamino)sulfonyl, (dialkylamino)sulfonyl, carbamoyl, (alkylamino)carbonyl, (dialkylamino)carbonyl, (carbamoyl)alkyl, (alkylamino)carbonylalkyl, or dialkylaminocarbonylalkyl}, O, or S(O)$_n$ (where n is an integer from 0 to 2), the remaining ring atoms being C. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino, dialkylamino, aralkyl, —(X)$_n$—C(O)R (where X is O or NR', n is 0 or 1, R is hydrogen, alkyl, haloalkyl, hydroxy, alkoxy, amino, monoalkylamino, dialkylamino or optionally substituted phenyl, and R' is hydrogen or alkyl), -alkylene-C(O)R (where R is hydrogen, alkyl, haloalkyl, hydroxy, alkoxy, amino, monoalkylamino, dialkylamino or optionally substituted phenyl) or —S(O)$_n$R$^d$ (where n is an integer from 0 to 2, and R is hydrogen (provided that n is 0), alkyl, haloalkyl, cycloalkyl, cycloalkylalkyl, amino, monoalkylamino, dialkylamino, or hydroxyalkyl).

"Heterocyclene" refers to a divalent saturated or unsaturated non-aromatic heterocycle or heterocyclyl as defined herein.

"Heteroarylene" refers to a divalent heteroaryl group as defined above.

"Heteroarylalkyl" refers to an alkyl radical as defined herein in which one of the hydrogen atoms of the alkyl group is replaced with a heteroaryl group.

"Heteroalkyl" refers to an alkyl radical as defined herein wherein one, two or three hydrogen atoms have been replaced with a substituent independently selected from the group consisting of —OR$^{a'}$, —NR$^b$R$^c$, and —S(O)$_n$R$^d$ (where n is an integer from 0 to 2), with the understanding that the point of attachment of the heteroalkyl radical is through a carbon atom, wherein R$^{a'}$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and like radicals.

"Hydroxyalkyl" refers to an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Phenylalkyl" refers to an alkyl radical as defined herein in which one of the hydrogen atoms of the alkyl radical has been replaced by an optionally substituted phenyl.

"Polycycle" or "polycyclyl" refers to an alkyl radical having two or more joined rings or cycles.

"Polycyclene" refers to a divalent polycycle alkyl radical as defined herein.

"Polycycloalkenyl" refers to a monovalent polycyclic unsaturated hydrocarbon radical of six to ten ring carbons and containing at least one double bond, e.g., norbornene, and like radicals.

"Homopolymer" and "copolymer" refer to polymer substances having substantially, respectively, homogeneous (i.e., the same) and heterogeneous (i.e., mixed) monomer contents in the polymer chain. A homopolymer of the disclosure has at least two or more of the same monomers covalently-linked. A homopolymer of the disclosure can have, in embodiments, individual polymer chains having from 2 to about 200,000 total monomer units or more, from 2 to about 100,000 total monomers, from 2 to about 10,000 total monomers, from 2 to about 1,000 total monomers, from 2 to about 100 total monomers, from 2 to about 50 total monomers, and from 2 to more than about 25 total monomers, depending upon, for example, the monomer reactant and reaction conditions selected, the molecular weight, polydispersity, and like considerations. A copolymer of the disclosure has at least two or more different monomers covalently-linked. A copolymer of the disclosure can have, in embodiments, individual polymer chains with from 2 to about 200,000 total monomer units or more, from 2 to about 100,000 total monomers, from 2 to about 10,000 total monomers, from 2 to about 1,000 total monomers, from 2 to about 100 total monomers, from 2 to about 50 total monomers, and from 2 to more than about 25 total monomers, depending upon for example, the reactants and reaction conditions selected, the molecular weight, polydispersity, and like considerations. "Oligomer," "oligomeric," or like terms refer to a subset of either the above "homopolymer" or "copolymer" terms. An oligomer of the disclosure has at least two or more monomers, the monomers being the same or different, and are covalently-linked. An oligomer of the disclosure can have, in embodiments, individual polymer chains having, for example, from 2 to about 25 total monomers or less, such as from 2 to about 20 total monomers, from 2 to about 15 total monomers, from 2 to about 10 total monomers, and from 2 to about 5 total monomers, depending upon for example, the reactants and reaction conditions selected, the desired molecular weight, polydispersity, and like considerations.

"Supported" in the phrase "supported compound of formula (I)" refers to any compound of formula (I) of the disclosure being associated with a suitable carrier. A suitable carrier, in embodiments, can be an oligomeric, a polymeric, a non-polymeric material, or mixtures thereof. The support or carrier can be covalently attached to the compound of formula (I), physically associated with the compound of formula (I) such as coated with or imbibed with the compound or polymer of compound of formula (I), or both covalently attached and physically associated with the compound or polymer of compound of formula (I). A suitable carrier can be, for example, metal oxide or mixed metal oxide particles, such as silicas, aluminas, borates, and like particles, or mixtures thereof, particles having surface structure such as pores or cavities, such as mesoporous silicas, zeolites, and like particles, magnetic nanoparticles, finely divided metals or metal salts, or mixtures or combinations of the above carriers. Similarly, "supported" in the phrase "supported polymer of the compound of formula (I)" refers to any oligomer, a homopolymer, or a copolymer of formula (I) of the disclosure being the carrier for an integral or covalently bonded catalytic site of the formula (I), or alternatively, being associated with a suitable carrier as defined above.

The indefinite article "a" or "an" and its corresponding definite article "the" as used herein means at least one, or one or more, unless specified otherwise.

"About" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

"Consisting essentially of" in embodiments refers, for example, to a single compound, mixture of compounds, a polymer or polymers of a compound, or a composition, the method of using the compound or compounds to catalyze reactions, and the resulting enantioselective products of the catalysis of the disclosure, and can include the components or steps listed in the claim, plus other components or steps that do not materially affect the basic and novel properties of the compounds, polymers, compositions, and methods of use of the disclosure, such as the particular substrates, particular catalysts, the particular process conditions, or like structure or process variables selected. Items that may materially affect the basic properties of the components or steps of the disclosure may impart undesirable characteristics to the present disclosure include, for example, decreased enantioselection, decreased resolution, decreased yield, decreased recyclability of the catalyst, and like characteristics. In embodiments, the compounds, the polymers, or the methods of the present disclosure preferably eliminate or avoid such undesirable characteristics.

"Optionally substituted" refers to any radical which is capable of substitution, such as an alkyl or phenyl group, is further substituted with one or more substituents, preferably one, two or three, substituents selected from, for example, alkyl, haloalkyl, hydroxyalkyl, heteroalkyl, acyl, acylamino, amino, alkylamino, dialkylamino, alkylthio, alkylsulfinyl, alkylsulfonyl, —$SO_2NR'R''$ (where R' and R'' are independently hydrogen or alkyl), alkoxy, haloalkoxy, alkoxycarbonyl, carbamoyl, hydroxy, halo, nitro, cyano, mercapto, methylenedioxy, or ethylenedioxy. More specifically the term includes, but is not limited to chlorophenyl, fluorophenyl, bromophenyl, methylphenyl, ethylphenyl, methoxyphenyl, cyanophenyl, 4-nitrophenyl, 4-trifluoromethylphenyl, 4-chlorophenyl, 3,4-difluorophenyl, 2,3-dichlorophenyl, 3-methyl-4-nitrophenyl, 3-chloro-4-methylphenyl, 3-chloro-4-fluorophenyl or 3,4-dichlorophenyl, and like substituted radicals.

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

"Salt" of a compound refers to a salt that possesses the desired chemical activity of the parent compound or polymer. Such salts include: (1) acid addition salts, formed with inorganic acids such as hydrochloric acid, hydrobromic acid, sulfuric acid, nitric acid, phosphoric acid, and like acid salts, such as $BF_3$, $BCl_3$, $BBr_3$ or $AlCl_3$; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, nitromethamine, N-methylglucamine, and like salts. Salts may be obtained using standard procedures well known in the art, for example, by reacting a sufficiently basic compound such as an amine with a suitable acid affording an acceptable anion. Alkali metals, for example, sodium, potassium or lithium, or alkaline earth metal salts, for example, calcium, of carboxylic acids can also be made. In embodiments, certain of the abovementioned salts can be selected as a suitable L counterion or ligand in a compound or a polymer of the formula (I) of the disclosure.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $(C_1-C_6)$alkyl or $C_{1-6}$alkyl refers to alkyl of one to seven carbon atoms, inclusive, and $(C_1-C_4)$alkyl or $C_{1-4}$alkyl refers to alkyl of one to four carbon atoms, inclusive.

The compounds of the present disclosure are generally named according to the IUPAC nomenclature system. Abbreviations, which are well known to one of ordinary skill in the art, may be used (e.g., "Ph" for phenyl, "Me" for methyl, "Et" for ethyl, "h" for hour or hours, "g" or "gm" for gram(s), "mL" for milliliters, and "rt" for room temperature).

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". The compounds of this disclosure may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

Specific and preferred values listed below for radicals, substituents, and ranges, are for illustration only; they do not exclude other defined values or other values within defined ranges for the radicals and substituents. The compounds of the disclosure include compounds of formulas (I) and like compounds having any combination of the values, specific values, more specific values, and preferred values described herein. Specifically, aryl can be phenyl, naphthyl, anthracenyl, phenanthrenyl, fluorenyl, tetrahydronaphthyl, or indanyl.

Specifically, $C_1$-$C_6$ alkyl can be methyl, ethyl, propyl, isopropyl, butyl, iso-butyl, sec-butyl, tert-butyl, pentyl, 3-pentyl, or hexyl; $C_{3-12}$ cycloalkyl can be cyclopropyl, cyclobutyl, cyclopentyl, cyclohexyl, cycloheptyl, cyclooctyl, and bicyclic, or multi- or polycyclic substituents, such as of the formulas

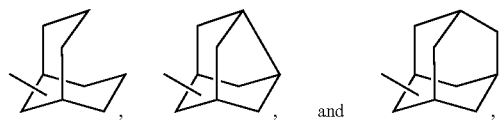

and unsaturated or polycycloalkenyl analogs; $C_1$-$C_6$ alkoxy, can be methoxy, ethoxy, propoxy, isopropoxy, butoxy, isobutoxy, sec-butoxy, pentoxy, 3-pentoxy, or hexyloxy; —C(=O)alkyl or $(C_{2-7})$alkanoyl or ketone can be acetyl, propanoyl, butanoyl, pentanoyl, 4-methylpentanoyl, hexanoyl, or heptanoyl; aryl can be phenyl, indenyl, or naphthyl; Het or heterocycle can be pyrrolidinyl, piperidinyl, morpholinyl, thiomorpholinyl, or heteroaryl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Specifically, —$(CH_2)_k$— can be a —$(C_{1-8}$alkylene)- when k is an integer from 1 to about 8, which can be methylenyl, ethylenyl, propylenyl, butylenyl, pentylenyl, 3-pentylenyl, hexylenyl, heptylenyl, or octylenyl.

A specific value for Het includes a five- (5), six- (6), or seven- (7) membered saturated or unsaturated ring containing 1, 2, 3, or 4 heteroatoms, for example, non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic Het diradical thereto.

A specific value for the linker L' is —(C≡C)$_k$—R$_5$, wherein R$_5$ is arylene, and k is 1.

Another specific value for the linker L' is —(C≡C)$_k$—R$_5$, wherein R$_5$ is an optionally substituted arylene, and k is 0.

Another specific value for the linker L' is an optionally substituted -Ph-.

Another specific value for the linker L' is an optionally substituted -Ph-Ph-.

Another specific value for the linker L' is an optionally substituted napthalyl.

Another specific value for the linker L' is —$C_1$-$C_6$ alkylene-O—$C_1$-$C_6$ alkylene-.

Another specific value for the linker L' is —$CH_2$—O—$(CH_2)_2$—.

Another specific value for L' is single carbon-carbon bond.

A specific value for the connector Z is —C(=O)O— or —O—C(=O)—.

Another specific value for Z is —C(=O)O—.

Another specific value for Z is single carbon-carbon bond.

A specific value for the polymerizable group P is $C_2$-$C_6$ alkenyl.

Another specific value for P is $C_2$ alkenyl.

Another specific value for P is arylene-$C_2$-$C_6$ alkenyl.

Another specific value for P is -Ph-CH$_2$=CH$_2$.

Another specific value for P is cycloalkenyl.

Another specific value for P is cyclo-octene.

Another specific value for P is norbornene.
A specific value for $R_3$ is a single carbon-carbon bond.
Another specific value for $R_3$ is —$CH_2$—.
Another specific value for $R_3$ is —O—.
A specific value for M is absent.
Another specific value for M is Co.
Another specific value for M is Mn.
Another specific value for M is Ru.
Another specific value for M is Cr.
Another specific value for M is Al.
A specific value for L is absent.
Another specific value for L is halide.
Another specific value for L is Cl.
Another specific value for L is I.
Another specific value for L is —OAc or acetate.
Another specific value for L is —OTs or -tosylate.

A specific compound of the formula (I) is the formula (I) wherein $X_1$, $X_2$, $X_3$, $X_4$, $X_5$, $X_6$, $X_7$, $X_8$, $Y_1$ and $Y_2$ are independently H, $C_1$-$C_6$ alkyl, and $C_1$-$C_6$ alkoxy, and at least one $X_1$, $X_2$, $X_3$, $X_4$, $X_5$, $X_6$, $X_7$, $X_8$, $Y_1$ and $Y_2$ is -L'-Z-P.

Another specific compound of the formula (I) is the formula (I) wherein $X_1$, $X_3$, $X_4$, $X_5$, $X_6$, $X_7$ and $X_8$ are independently H or t-butyl; $Y_1$ and $Y_2$ are H; $R_1$ and $R'_2$ are a carbocycle or heterocycle comprising 4 to 10 atoms, when $R_2$ and $R'_1$ are H, or $R_1$ and $R'_2$ are H, when $R_2$ and $R'^1$ are a carbocycle or heterocycle comprising 4 to 10 atoms; $R_3$ is a single carbon-carbon bond; and $X_2$ is -L'-Z-P.

Another specific compound of the formula (I) is formula (I) wherein $X_1$, $X_3$, $X_6$, and $X_8$ are H; $X_4$, $X_5$, and $X_7$ are t-butyl; $Y_1$ and $Y_2$ are H; $R_1$ and $R'_2$ are a —$(CH_2)_4$—, when $R_2$ and $R'^1$ are H, or $R_1$ and $R'_2$ are H, when $R_2$ and $R'^1$ are a —$(CH_2)_4$—; $R_3$ is a single carbon-carbon bond; $X_2$ is -L'-Z-P where L' is a single carbon-carbon bond or —(C≡C)$_k$—Ar—, where k is 1;

Z is —C(=O)O— or —O—C(=O)—;

P is $C_2$-$C_6$ alkenyl, cycloalkenyl, or polycycloalkenyl;

M is Co, Mn, or mixtures thereof; and

L is absent or a halide anion selected from F, Cl, Br, and I; or a salt or hydrate thereof.

Another specific compound of the formula (I) is formula (I) wherein $X_2$ is -L'-Z-P where L' is a single carbon-carbon bond or —(C≡C)$_k$—Ar—, where k is 1; Z is —C(=O)O— or —O—C(=O)—; P is ethenyl, 5-cyclooctenyl, or 4-norbornenyl; M is Co or Mn; and L is absent or a halide anion such as F, Cl, Br, and I; or a salt or hydrate thereof.

A specific homopolymer of the compound of the formula (I) is of the formula:

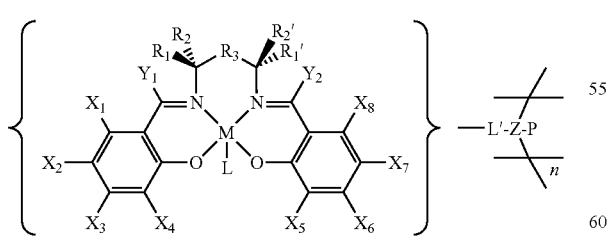

wherein $R_1$, $R_2$, $R'_1$, $R'_2$, $X_1$, $X_2$, $X_3$, $X_4$, $X_5$, $X_6$, $X_7$, $X_8$, $Y_1$ and $Y_2$ are as defined herein, and at least one $X_1$, $X_2$, $X_3$, $X_4$, $X_5$, $X_6$, $X_7$, $X_8$, $Y_1$ and $Y_2$ is independently of the formula -L'-Z-P as defined herein;

M is a metal atom or ion is at least one of Co, Mn, Cr, Al, Zn, Ru, Fe, Mo, Ni, or mixtures thereof;

L is a halide anion selected from F, Cl, Br, and I; and n is 2 to 2,500;

or a salt or hydrate thereof.

Another specific homopolymer of the compound of the formula (I) is of the above formula wherein $R_1$, $R_2$, $R'_1$, $R'_2$, $X_1$, $X_2$, $X_3$, $X_4$, $X_5$, $X_6$, $X_7$, $X_8$, $Y_1$ and $Y_2$ are as defined above, and only one of $X_1$, $X_2$, $X_3$, $X_4$, $X_5$, $X_6$, $X_7$, $X_8$, $Y_1$ and $Y_2$ is of the formula -L'-Z-P as defined herein.

Another specific homopolymer of the compound of the formula (I) is of the formula:

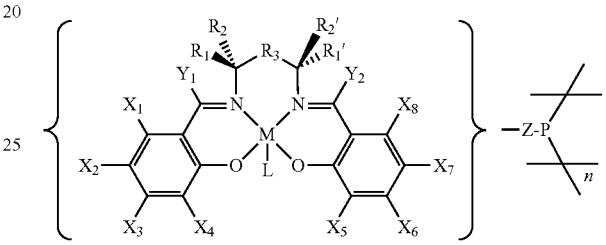

where $R_1$, $R_2$, $R'_1$, $R'_2$, $X_1$, $X_2$, $X_3$, $X_4$, $X_5$, $X_6$, $X_7$, $X_8$, $Y_1$ and $Y_2$ are as defined herein, and at least one $X_1$, $X_2$, $X_3$, $X_4$, $X_5$, $X_6$, $X_7$, $X_8$, $Y_1$ and $Y_2$ is independently of the formula -L'-Z-P as defined herein; and L' is a single carbon-carbon bond.

Another specific homopolymer of the compound of the formula (I) is of the

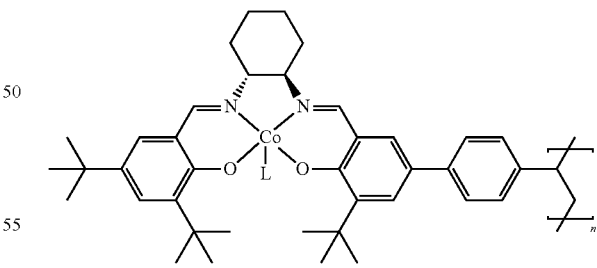

wherein

L is absent, or a tosylate, an acetate, or a halide anion selected from F, Cl, Br, and I; and n is 2 to 2,500; or a salt or hydrate thereof.

Another specific homopolymer of the compound of the formula (I) is of the formula:

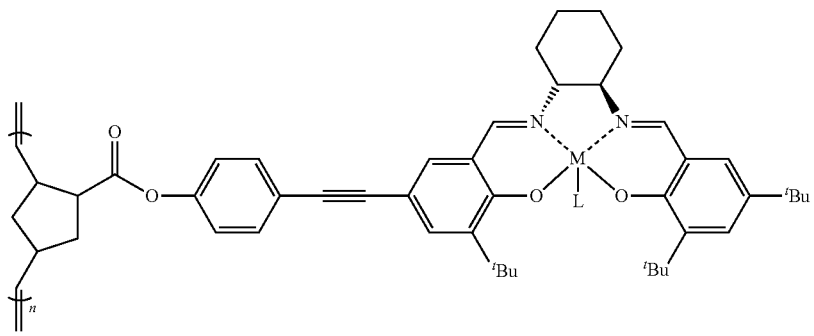

wherein

M is a metal atom or ion of at least one of Co, Mn, or mixtures thereof;

L is absent, or a tosylate, an acetate, or a halide anion selected from F, Cl, Br, and I; and n is 2 to 2,500; or a salt or hydrate thereof.

Another specific homopolymer or oligomer of the compound of the formula (I) is the ring-expanded formula:

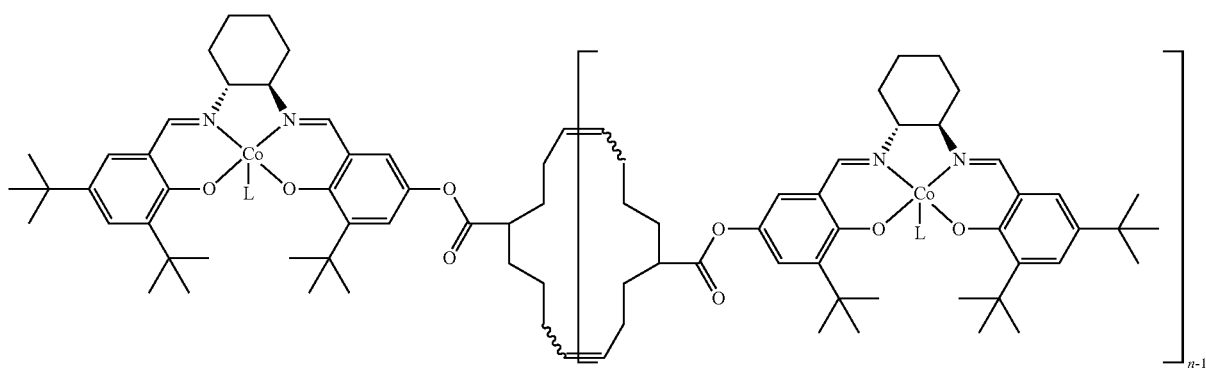

wherein L is a counterion as defined herein, for example, a tosylate, an acetate, or a halide anion selected from F, Cl, Br, and I; and n is 2 to 100; or a salt or hydrate thereof.

A specific copolymer of the compound of the formula (I) is of the formula:

$\{(A)_m\text{-}(B)_p\}$ where

A is a mer representing the polymerized compound of formula (I);

B is a co-polymerized monomer;

m is an integer from 1 to about 1,000; and p is an integer from 1 to about 10,000.

Another specific copolymer of the compound of the formula (I) is of the formula:

$\{(A)_m\text{-}(B)_p\}$ where

A is the polymerized compound of formula (I);

B is a co-polymerized monomer of at least one of an olefin, a perfluorinated olefin, a silane or siloxane substituted olefin, a diene, an alkenylaryl, an acylate, or mixtures thereof;

m is an integer from 10 to about 100; and p is an integer from 10 to about 1,000.

Another specific copolymer of the compound of the formula (I) is of the formula $\{(A)_m\text{-}(B)_p\}$ where A is a mer representing the polymerized compound of formula (I) and B is a co-polymerized monomer of, for example, ethylene, propylene, butadiene, styrene, norbornene, an alkylcarboxy substituted norbornene, an acylate, or mixtures thereof;

Another specific copolymer of the compound of the formula (I) is of the formula:

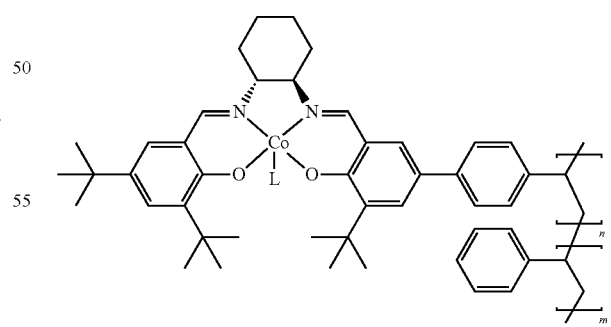

wherein

L is a counterion as defined herein, for example, a tosylate, an acetate, or a halide anion selected from F, Cl, Br, and I;

m is 2 to 100; and n is 2 to 50; or a salt or hydrate thereof.

Another specific copolymer of the compound of the formula (I) is of the formula:

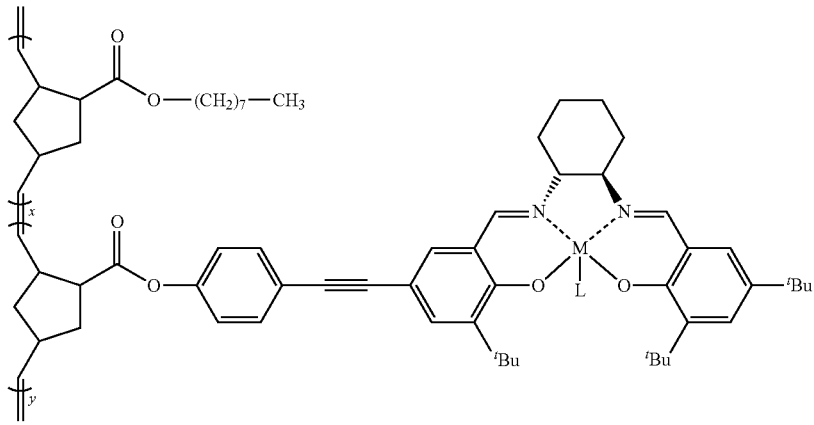

wherein
M is Mn, Co, or mixtures thereof;
L is absent, or a counterion as defined herein, for example, a tosylate, an acetate, or a halide anion selected from F, Cl, Br, and I;
x is 2 to 100; and
y is 2 to 50; or a salt or hydrate thereof.

A specific homopolymer or oligomer of formula (I) is the unsymmetrical oligomeric macrocycle of the formula:

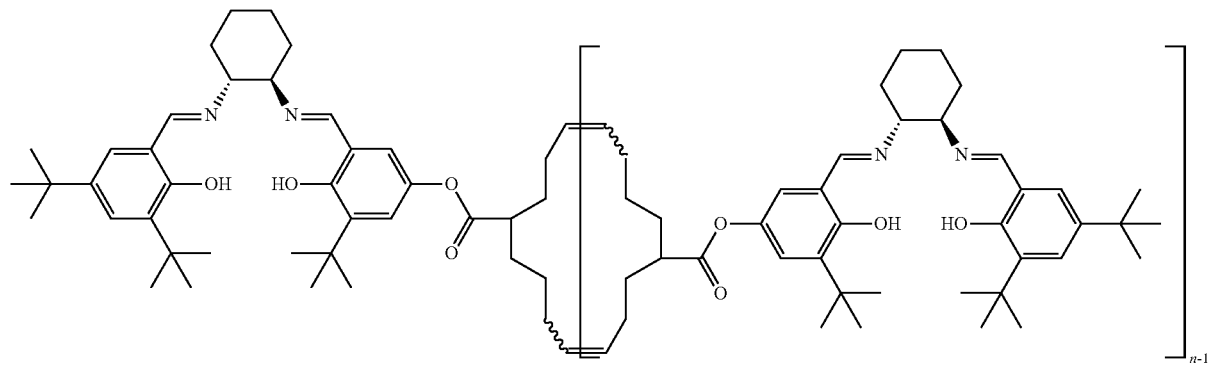

where M and L are absent, and n is from 2 to about 2,500.

Another specific cyclic homopolymer or oligomer of formula (I) is the metalated unsymmetrical oligomeric macrocycle catalyst of the formula:

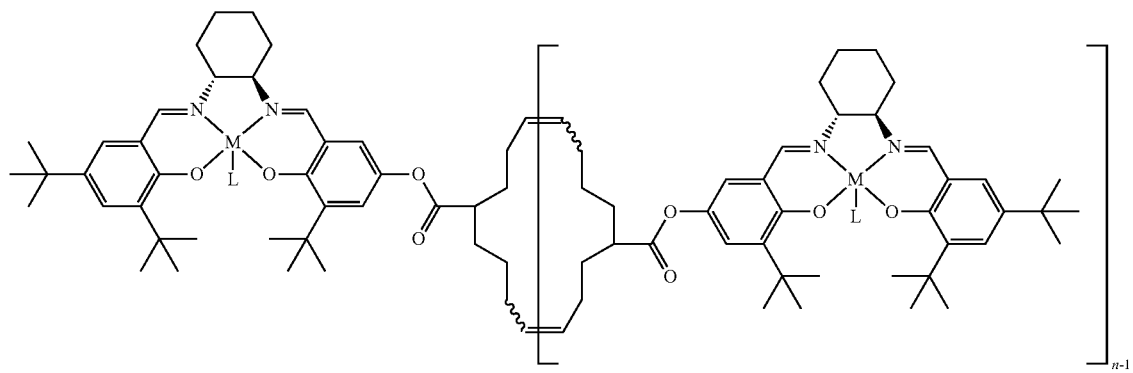

where M is Co, L is absent or a counter ion, and n is from 2 to about 100.

Another specific oligomer of formula (I) is the metalated unsymmetrical dimeric macrocycle of the formula:

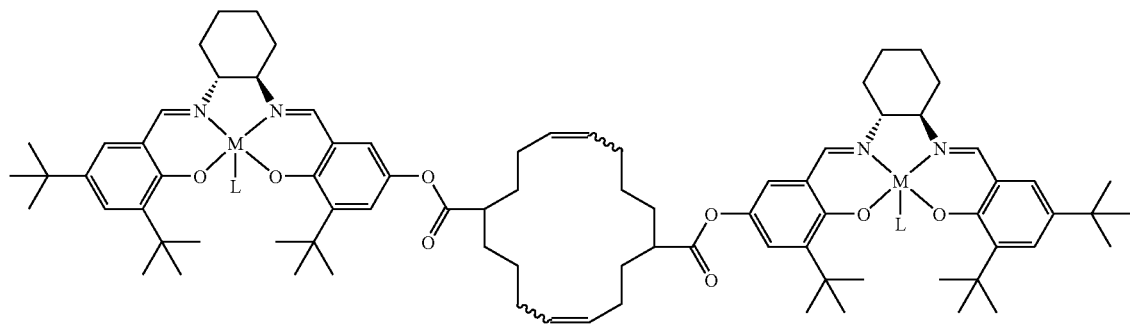

where M is Co, and L is absent or a counter ion.

Another specific oligomer of formula (I) is the unmetalated unsymmetrical dimer macrocycle of the above formula, i.e., M and L absent.

The abovementioned specific and preferred compounds and polymers can include, for example, individual isomers, racemic and non-racemic mixtures of isomers, and salts and solvates thereof.

In embodiments, the present disclosure provides a method for preparing a homo-polymer of the compound of formula (I), comprising: heating the compound of formula (I) with a free radical initiator, for example, a carbon centered free radical source such as AIBN, or like carbon centered free radical source, or an oxygen centered free radical source such as an benzoyloxy radical (Ph-CO—O.), or like oxygen centered free radical source.

In embodiments, the present disclosure provides a method for preparing an oligomeric-ring or macrocyclic-ring homo-polymer of the compound of formula (I) comprising: reacting the compound of formula (I) with a second or a third generation (3°) Grubbs catalyst, for example, of the formulas:

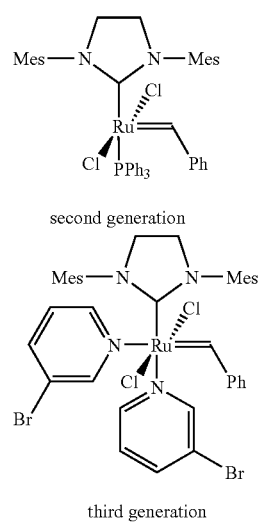

second generation third generation where Mes is a mesylate radical, —O(S=O)$_2$—CH$_3$, or like substituents.

In embodiments, the present disclosure provides a method for preparing a co-polymer of the compound of formula (I)

comprising: heating the compound of formula (I) with a free radical initiator and at least one monomer selected from olefin, diene, alkenylaryl, acylate, or mixtures thereof.

In embodiments, the present disclosure provides a method of preparing a chiral epoxide or chiral 1,2-diol by stereoselective hydrolysis (HKR) of a racemic epoxide of the formula

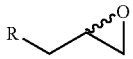

wherein R is hydrogen, $C_1$-$C_{10}$ alkyl, $C_2$-$C_6$ alkenyl, $C_2$-$C_6$ alkynyl, $C_3$-$C_8$ cycloalkyl, $C_1$-$C_{10}$ alkoxy, aryl, carbonyl, carboxy, ketone, aldehyde, ester, phosphoryl, phosphonate, phosphine, sulfonyl, or —$(CH_2)_k$—$R_5$ wherein, $R_5$ is $C_2$-$C_6$ alkenyl, $C_2$-$C_6$ alkynyl, $C_2$-$C_6$ alkoxy, unsaturated alkoxy, aryl, cycloalkyl, cycloalkenyl, heterocycle, polycycle, halogen, hydroxy, amino, thiol, nitro, amine, imine, amide, carbonyl, carboxy, silyl, ether, thioether, seleno ether, ketone, aldehyde, ester, phosphoryl, phosphonate, phosphine, sulfonyl and k is an integer of 0 to 8, the method comprising:

contacting the racemic epoxide with water in the presence of a catalytic amount of a chiral homo-polymer, a chiral copolymer, or a chiral oligomer of the compound of formula (I) as defined herein,
wherein
$X_1$, $X_3$, $X_6$, and $X_8$ are H;
$X_4$, $X_5$, and $X_7$ are t-butyl;
$Y_1$ and $Y_2$ are H;
$R_1$ and $R'_2$ are a —$(CH_2)_4$—, when $R_2$ and $R'^1$ are H, or $R_1$ and $R'_2$ are H, when $R_2$ and $R'^1$ are a —$(CH_2)_4$—;
$R_3$ is a single carbon-carbon bond;
$X_2$ is -L'-Z-P where
L' is —$(C\equiv C)_k$—Ar— where k is 1;
Z is —C(=O)O— or —O—C(=O)—;
P is a polymerized $C_2$-$C_6$ alkenyl, or polycycloalkenyl;
M is Co; and
L is absent or a counterion as defined herein, for example, a tosylate, an acetate, or a halide anion;
or a salt or hydrate thereof;

In embodiments, the present disclosure also provides a method of preparing an asymmetric epoxide of an olefin comprising:

contacting the olefin with a catalytic amount of a chiral homo-polymer or chiral copolymer of the compound of formula (I) as defined herein, and optionally in the presence of an oxygen source, such as N-methyl-morpholino-N-oxide, wherein
$X_1$, $X_3$, $X_6$, and $X_8$ are H;
$X_4$, $X_5$, and $X_7$ are t-butyl;
$Y_1$ and $Y_2$ are H;
$R_1$ and $R'_2$ are a —$(CH_2)_4$—, when $R_2$ and $R'^1$ are H, or $R_1$ and $R'_2$ are H, when $R_2$ and $R'^1$ are a —$(CH_2)_4$—;
$R_3$ is a single carbon-carbon bond;
$X_2$ is -L'-Z-P where
L' is —$(C\equiv C)_k$—Ar—;
Z is —C(=O)O— or —O—C(=O)—;
P is $C_2$-$C_6$ alkenyl, or polycycloalkenyl;
M is Mn; and
L is absent or as define herein;
or a salt or hydrate thereof.

In embodiments, the present disclosure provides a single-pot method for preparing the compound of formula (I), the method comprising:

reacting a salicylaldehyde compound of the formula (A):

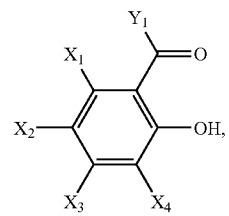

with an (R,R)-diamino mono-ammonium salt of the formula:

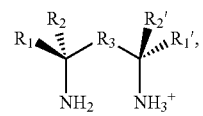

to form a mono-ammonium imine of the formula (B):

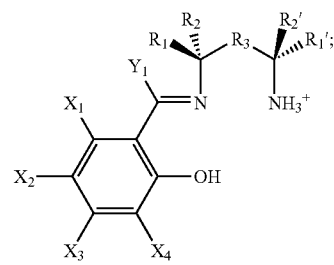

deprotecting the mono-ammonium imine of formula (B) with a base and thereafter reacting the deprotected imine with an aldehyde of formula (C):

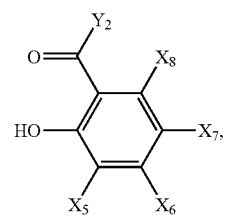

to form an unsymmetrical substituted salen of formula (D):

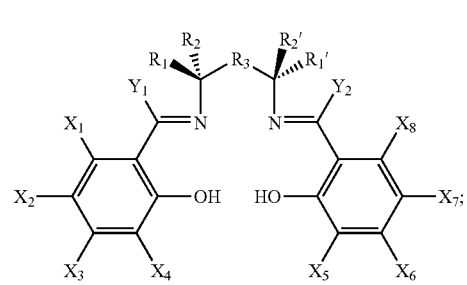

and optionally reacting the salen of formula (D) with a metal salt to form the metalated-salen complex of the formula (I):

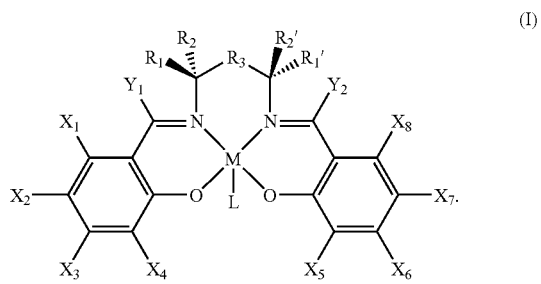

In embodiments, the present disclosure provides a single-pot method for preparing a compound of formula (I) in high yield, wherein the compound of formula (I) can be, for example:

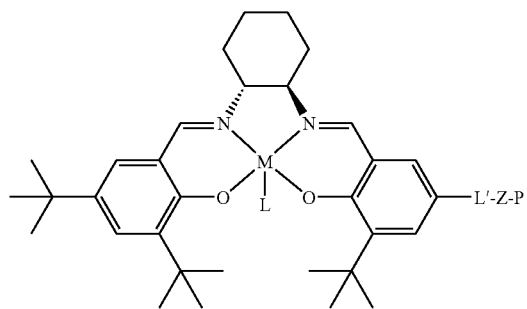

where -L'-Z-P, M, and L can be any of the values as defined herein.

In embodiments, the above methods for preparing the compound of formula (I) can include isolation of intermediate compounds, if desired, although generally unnecessary.

General Synthetic Schemes

The compounds of the present invention can be prepared in a number of ways known to one skilled in the art. Preferred methods include, but are not limited to, the general synthetic procedures described below. These schemes are merely illustrative of some methods by which the compounds of this disclosure can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography, and like methods. Such materials may be characterized using conventional means, including physical constants and spectral data.

The starting materials and reagents used in preparing these compounds are either available from commercial suppliers, such as Sigma-Aldrich Chemical Co., (St. Louis, Mo., USA), Maybridge (Dist: Ryan Scientific, P.O. Box 6496, Columbia, S.C. 92960), Bionet Research Ltd., (Cornwall PL32 9QZ, UK), Menai Organics Ltd., (Gwynedd, N. Wales, UK), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 1992), House's Modern Synthetic Reactions (W. A. Benjamin, New York, 1972); and Larock's Comprehensive Organic Transformations (VCH Publishers Inc., 1989). It may be desirable to optionally use a protecting group during all or portions of the above described or alternative synthetic procedures. Such protecting groups and methods for their introduction and removal are well known in the art. See Greene's "Protecting Groups In Organic Synthesis," (John Wiley & Sons, 1991).

Styrene is one of the monomers used in the example co-polymerizations. Many other monomers are also equally suitable, and include for example, a substituted styrene such as vinyltoluene and bromostyrene, an acrylic acid, an acrylonitrile, an acrylamide, an alkylacrylate such as methyl methacrylate, a diene such as a butadiene, an isoprene, a vinyl ester, a vinyl ether, a vinyl pyridine, a vinylidene chloride, a vinyl chloride, a fluorinated or perfluorinated alkylene such as tetrafluoroethylene, a silane substituted monomer, a siloxane substituted monomer, an epoxy monomer, and derivatives of these compounds. Other suitable monomers can include, for example, cyclic, bicyclic, or polycyclic monomers, for example, norbornene, cyclooctene, cyclooctadiene, cylcooctatetraene, cyclobutene, cyclopentene, cyclopentadiene, barrelenes such as bicyclo[2.2.2]octenes, and functionalized versions thereof. Functionalized versions include, for example, optionally substituted olefins or dienes, such as substituted with an acid, ester, aldehyde, ketone, amide, $C_1$-$C_6$ alkyl, $C_{3-12}$ cycloalkyl, aryl, het, $C_1$-$C_6$ alkoxy, halogen, —OH, —SH, —$NO_2$, —$NH_2$, amino, imine, carboxy, silyl, ether, thio ether, seleno ether, phosphoryl, phosphonate, phosphine, sulfonyl, and like functional groups, or combinations thereof. Additionally, suitable co-monomers can include mixtures of two or more different monomer, such as styrene/butadiene, styrene/vinyltoluene, vinyltoluene/tert-butylstyrene, and like combinations. Copolymers can include two or more monomers in combination with a polymerizable catalyst monomer to form for example, terpolymers, and like mixed copolymers, and including all permutations of monomer combinations and geometries, such as random, alternating, block, di-block, multi-block, graded, tapered, linear, branched, comb, dendritic, and like forms. If desired, known cross-linking agents, such as divinylbenzene, and cross-linking methodologies can be used, either during polymerization or in post-polymerization processing, to further tailor the physical parameters and catalytic properties of the catalyst complexes. Similarly, known branching agents and branching methodologies can be used, either during polymerization or in post-polymerization processing, to further tailor the physical parameters and catalytic properties of the catalyst complexes. In addition to ring-opening metathesis polymerization (ROMP) and the polymerizations processes illustrated herein, other polymerization methodologies can be used in conjunction with a compound of formula (I), if desired, to obtain the polymer or oligomer products of the disclosure, for example, other olefin metathesis methods such as ADMET (acyclic diene metathesis), controlled radical polymerization techniques such as ATRP (atom transfer radical polymerization), RAFT (reversible addition fragmentation transfer polymerization), NMP (nitroxide mediate polymerizations), or SFR (stable free radical polymerizations, see for example U.S. Pat. No. 5,322,912 and its progeny).

Preparation of compounds of formula (I) and their conversion to homopolymers, copolymers, and oligomers, are illustrated in Schemes 1-9.

Synthesis of Compounds of Formula (I)—Monomer Ligands

Compounds of formula (I) are generally prepared as shown schematically below and as described in greater detail in the Experimental and Examples section.

Several salicylaldehydes functionalized with an immobilizing or coupling group, such as, —OH, —SAc, or —CH=CH$_2$, and a linker (L') of either a rigid spacer (phenylacetylene or phenylene) or a flexible spacer (alkyl or ethylene glycol) were prepared as precursors in the synthesis of unsymmetrical salen ligands, as outlined in Scheme 1.

For the preparation rigid of linker-based compounds, a Pd-catalyzed Sonogashira or Suzuki coupling reactions to yield 2a-c (Path A) was employed. Both coupling reactions showed tolerance to the presence of hydroxy, acetylsulfanyl, vinyl, or formyl functional groups. Salicylaldehydes 2d and 2e were produced by nucleophilic substitutions of 3-tert-butyl-5-chloromethylsalicylaldehyde with RONa (R=—H, —CH$_2$CH$_2$OH) (Path B). Friedel-Crafts alkylation of 2-tert-butylphenol with 7-methyl-7-octenoic acid, followed by the reduction of the carboxylic acid with LiAlH$_4$ and the acid-catalyzed formylation reaction produced 2f with a long alkyl chain (Path C).

Scheme 1. Synthesis of the salicylaldehydes 2.

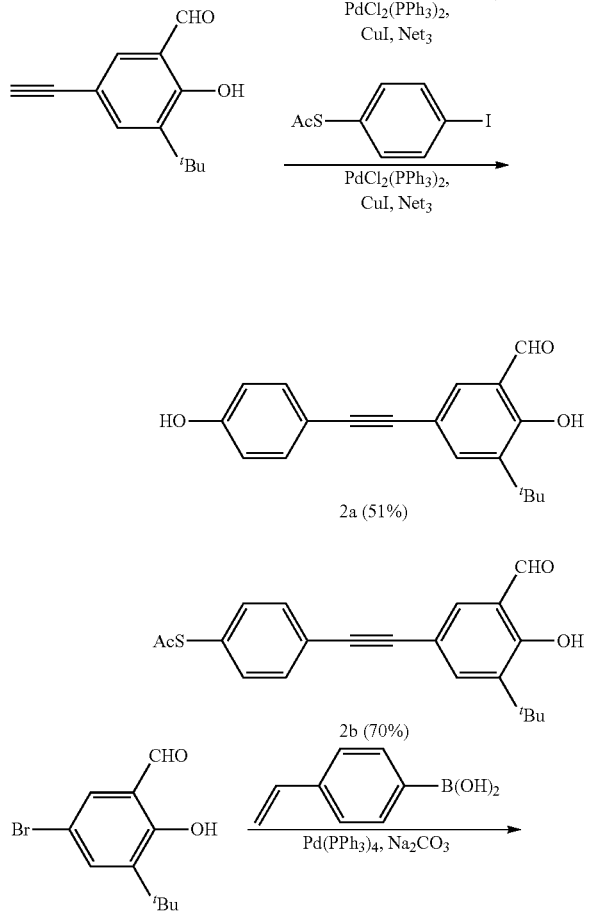

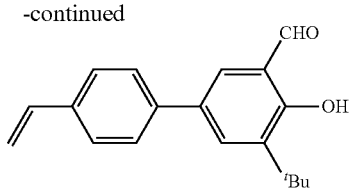

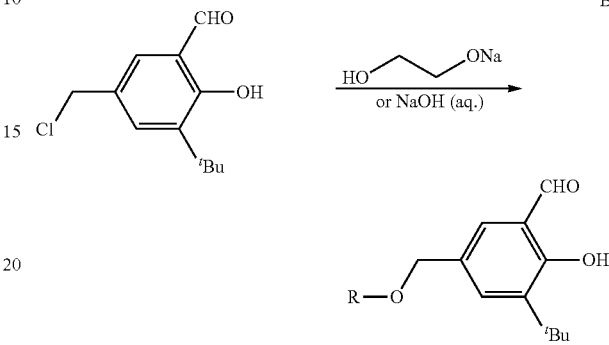

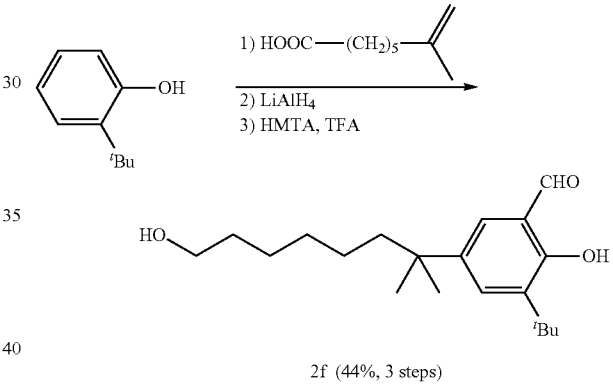

As shown in Scheme 2, for the preparation of enantiopure unsymmetrical salen ligands, a one-pot approach was used to avoid the isolation step of the mono-imine intermediate that is prone to the undesired disproportionation reaction. Hydrogen chloride was selected to form a protective acid salt of one amine group of the diamine. The mono-ammonium salt 3 was prepared in near quantitative yield from a 1:1 molar ratio of (R,R)-diaminocyclohexane and 2.0 M hydrogen chloride in ether. The first condensation between 3 and 3,5-di-tert-butyl-salicylaldehyde was carried out in a 1:1 (v/v) mixture of anhydrous methanol and ethanol at ambient temperature. Use of activated 4 Å molecular sieves to remove the water formed during the reaction was found significant in reducing the reaction time to four hours and depressing the exchange of the salicylidene moieties. After the first condensation was complete, a solution of the functionalized salicylaldehyde 2 in dichloromethane was added to the reaction system, followed by the slow addition of an excess of anhydrous triethylamine as a deprotective base. The TLC analysis and $^1$H NMR spectra showed that the second condensation was completed within four hours and only traces of symmetrical salens were detected.

The target unsymmetrical salen ligands 4 were isolated in 60-85% yields as light yellow solids by means of column chromatography on silica gel pretreated with methanol or methanol/triethylamine. The reaction was very time and reproducibility efficient and was easily scaled up and carried out on a multigram scale.

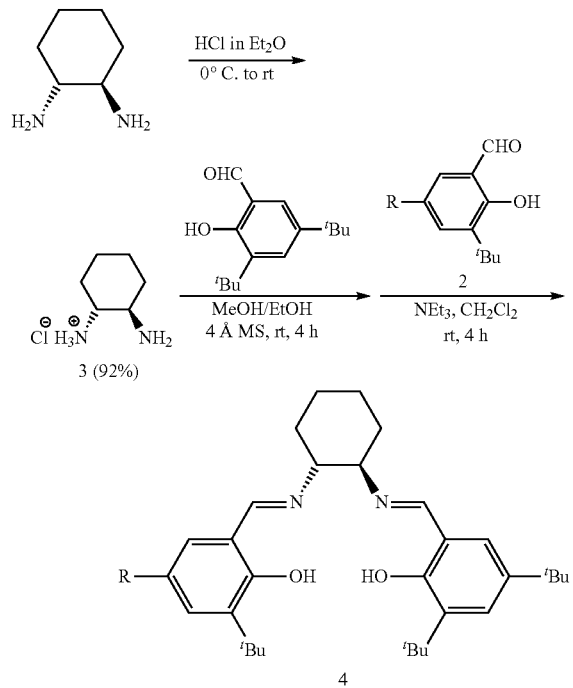

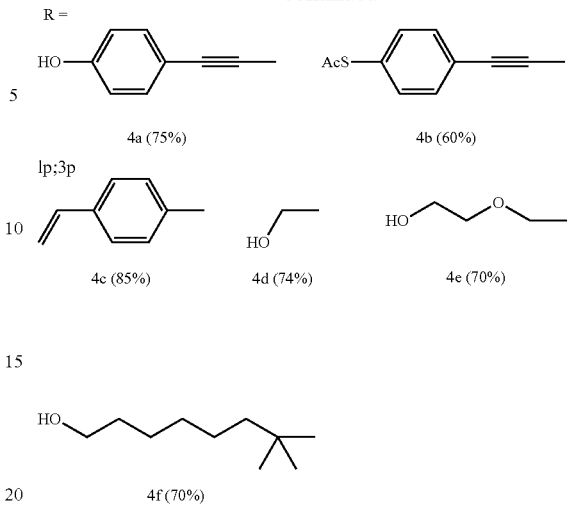

The preparation of mono-functionalized Mn- and Co-salen complexes 9 and 10 attached to a norbornene monomer via a stable phenylacetylene linker are shown in Scheme 3. The mono-functionalized salens were obtained by the de-symmetrization of 1,2-diaminocyclohexane 2 with HCl to yield the mono-ammonium salt 3. After reaction of 3 with 4, the resulting mono-ammonium imine 5 was deprotected with NEt$_3$ in the above described one-pot procedure and reacted with the functionalized aldehyde 6. After an esterification of the resulting unsymmetrically substituted salen 7 with 8 and subsequent metalation, the functionalized Mn- and Co-salen norbornenes 9 and 10 were obtained in good yield.

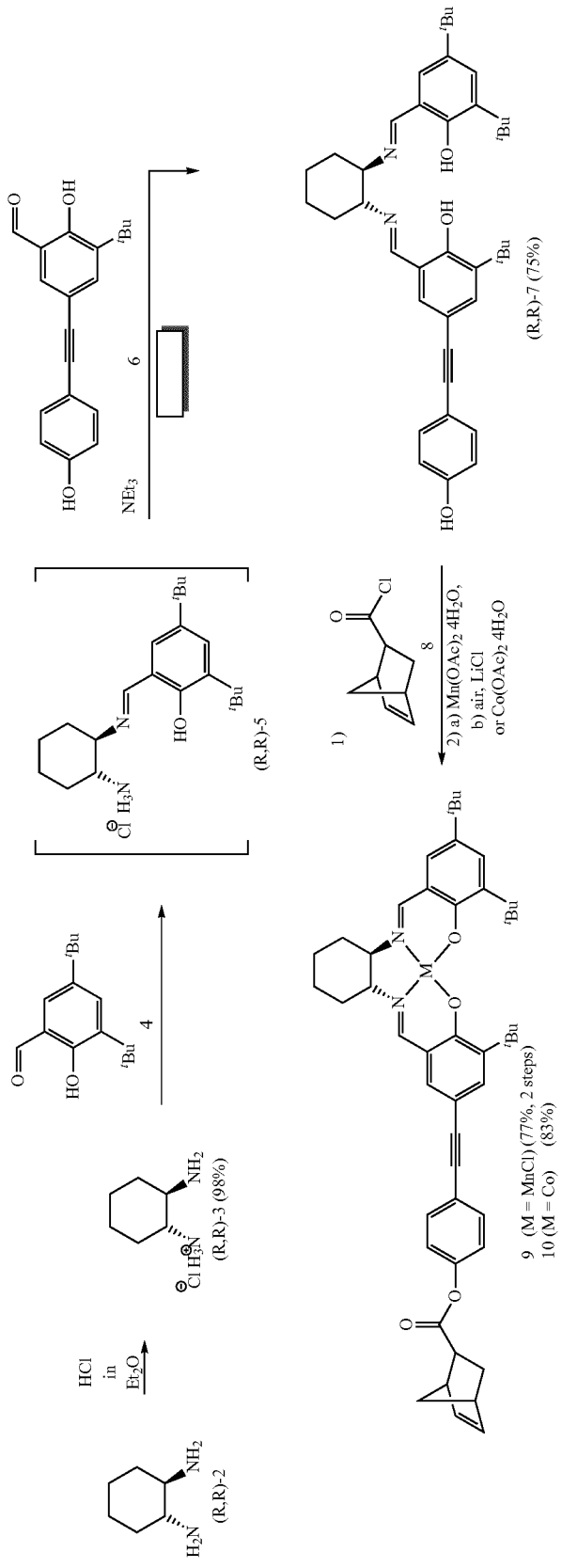
Scheme 3. Synthesis of the norbornene-functionalized salen ligand and their manganese- and cobalt complexes 9 and 10.

Cyclooctene-functionalized salen ligands were prepared, for example, as shown Scheme 4. Esterification of 3-t-butyl-2,5-dihydroxybenzaldehyde and cyclooct-4-enecarboxylic acid in the presence of 1,3-dicyclohexylcarbodiimide (DCC) and 4-dimethylaminopyridine (DMAP) yield the salicylaldehyde cyclooct-4-enecarboxylate product. A one-pot stepwise condensation of (R,R)-diaminocyclohexane mono-ammonium salt with 3,5-di-t-butylsalicylaldehyde and the salicylaldehyde cyclooct-4-enecarboxylate in a 1:1:1 molar ratio afforded cyclooct-4-en-1-yl substituted unsymmetrical salen ligand in 84% yield.

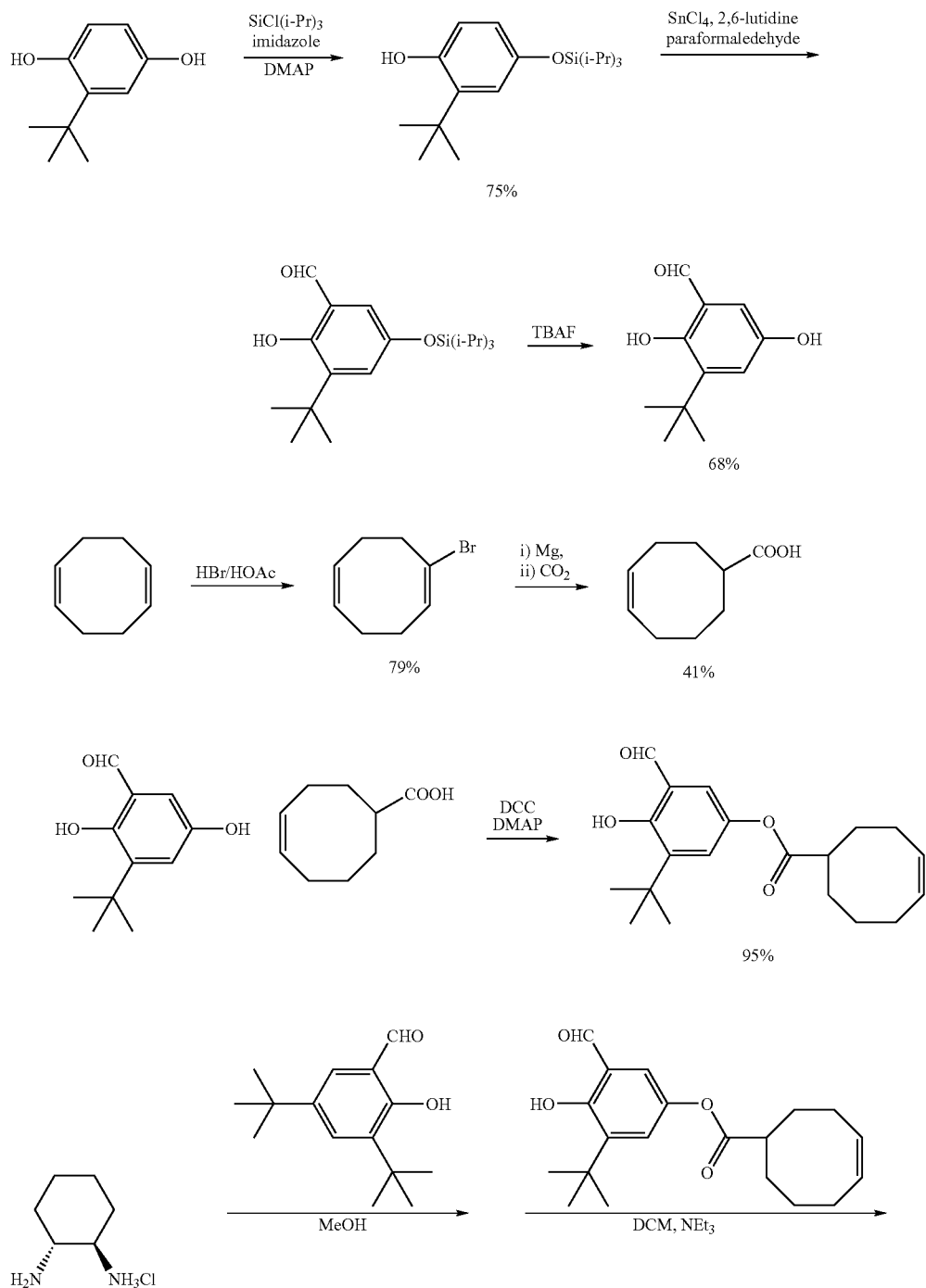

Scheme 4. Synthesis of cyclooctene-functionalized salen ligands.

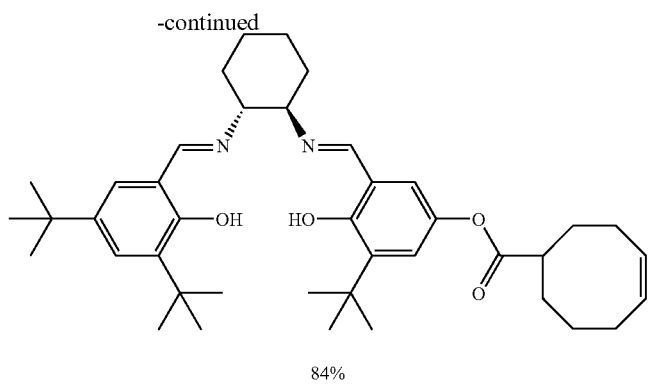

84%

Polymerization of Compounds of Formula (I)

Synthesis and Polymerization of the Mono-Norbornene Functionalized Salens

The monomeric metalized complexes 9 and 10 were homo- and co-polymerized using a controlled polymerization method, such as ring-opening metathesis polymerization (ROMP), and thereby avoided a post-polymerization metal complexation step. The polymeric manganese and cobalt complexes were used as supported catalysts, for example, for asymmetric epoxidations of different olefins and for the hydrolytic kinetic resolution of epoxides. The polymeric catalysts showed excellent catalytic activity and selectivity. Unexpectedly, the activity and selectivity of the catalyst was found to depend upon the density of the catalytic moieties along the polymer backbones. In general, the copolymer complexes were slightly more active and selective as catalysts compared to the homopolymer complex analogues. This was true for both the manganese and the cobalt-based catalysts. When the cobalt-salen moieties were present in the copolymer chain at less than about 15% (i.e., cobalt-salen derived monomer:co-monomer molar ratio) in the polymer backbone a drop in catalytic activity was observed.

ROMP of the analytically pure and fully characterized monomers using the [Ru] 3°-generation Grubbs catalyst, yielded p(9) and p(10) as shown in Scheme 5. Furthermore, copolymers of 9 and 10 were prepared with the unfunctionalized norbornene 11 to (i) site-isolate individual catalyst sites and (ii) probe the effect of catalyst loadings on the catalytic activity.

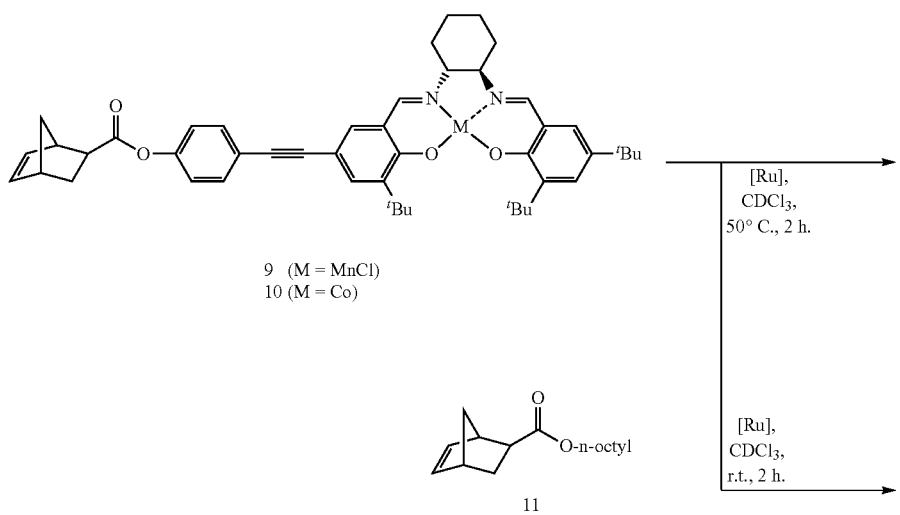

Scheme 5. Ring-opening metathesis polymerization (ROMP) of the norbornene-functionalized metal-salen-complexes 9 and 10

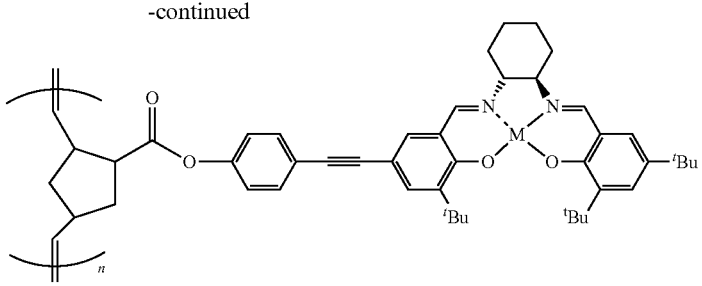

p(9)  (M = MnCl, n = 50)
p(10) (M = Co, n = 20)

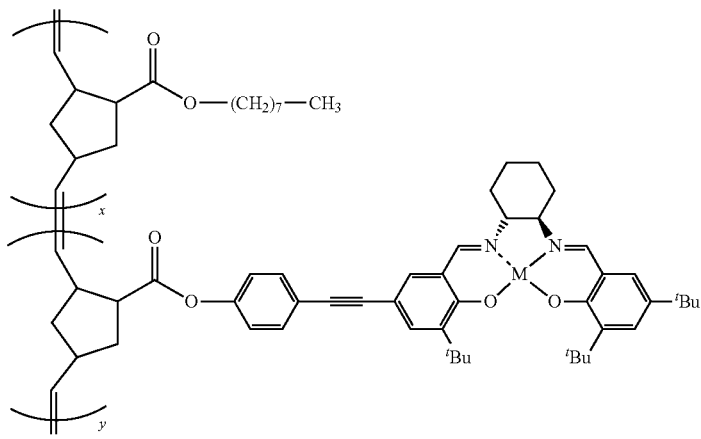

p(9.11)₁₁ (M = MnCl), p(10.11)₁₁ (M = Co) (x/y = 1:1, x + y = 50)
p(9.11)₁₃ (M = MnCl), p(10.11)₁₃ (M = Co) (x/y = 3:1, x + y = 100)
p(9.11)₁₉ (M = MnCl), p(10.11)₁₉ (M = Co) (x/y = 9:1, x + y = 100)

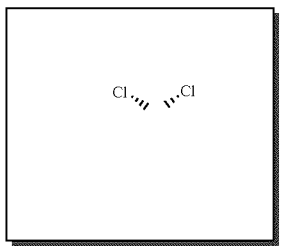

As shown in Scheme 6 the monomeric cobalt salen complex 38 was obtained via an acylation of salen ligand 25c with norbornene chloride 26, followed by a complexation of Co(OAc)$_2$. ROMP of the analytically pure and fully characterized metalated monomer using the 3°-generation Grubbs catalyst, yielded homopolymer p(38). Copolymers of 38 were prepared with the unfunctionalized norbornene 29 to (i) site-isolate individual catalyst sites and (ii) probe the effect of catalyst loadings on the catalytic activity. The polymerization rates were followed using $^1$H-NMR spectroscopy by focusing on the signals of the olefin protons. In all cases, monomer conversions (monomer to catalyst ratios up to 100:1) were quantitative after one to two hours. Moreover, $^1$H-NMR spectroscopy of the homopolymerizations of ten equivalents of 29 and 38 using the 3°-generation Grubbs catalyst revealed that the polymerization kinetics were similar with complete monomer-conversion achieved after about 2-5 minutes. The results suggest that the copolymerization of 38 and 29 yield statistical copolymers p(38.29), i.e., the monomers containing the catalytic moiety of formula (I) are randomly dispersed in the alkyl-norbornene copolymer matrix. These polymeric Co(II)-complexes could be oxidized to the corresponding Co(III) compounds p(38a) and p(38a-co-29) by O$_2$ in the presence of acetic acid to afford the corresponding acetate (L=-OAc).

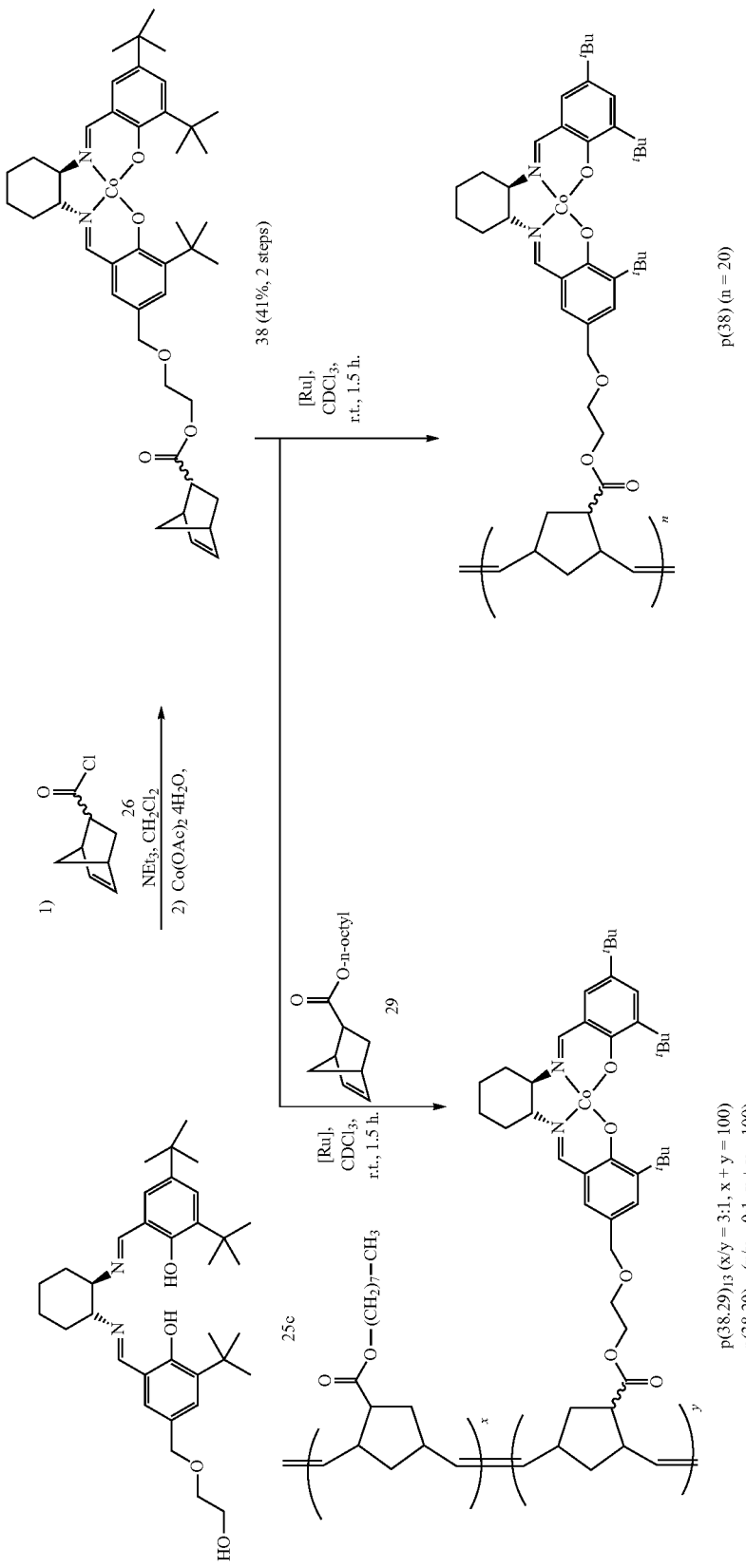

Homopolymer and Poly(styrene)-Supported Co(Salen) Complexes

The reuse (reusability or recyclability) of a metal-based catalyst is a fundamental characteristic for the broad commercial acceptance of homogeneous or heterogeneous catalysts. One reaction that has potentially large industrial implication is the hydrolytic kinetic resolution (HKR) of diols from racemic epoxide mixtures using cobalt-salen complexes. While a wide variety of supported Co-salen complexes have been reported, they often decompose (at least partially) under the catalyzed reaction conditions. Thus, the robust poly(norbornene) and poly(styrene) supported salen ligands of the present disclosure were prepared. The polymer supported ligands could be metalated, for example, with cobalt to yield the fully supported Co-salen complexes that were as active as their non-supported analogs. This complex can be recycled and reused without decomposition.

Homopolymer chiral Co(salen) and copoly(styrene)-immobilized chiral Co(salen) complexes were prepared by the free radical polymerization of a styryl-substituted unsymmetrical salen monomer, alone or with a styrene co-monomer, as shown in Scheme 7.

Scheme 7. Synthesis of homopolymeric salen ligand and co-polymeric polystyrene-supported salen ligands.

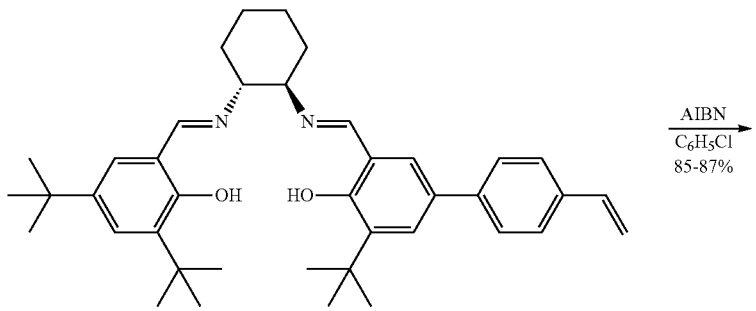

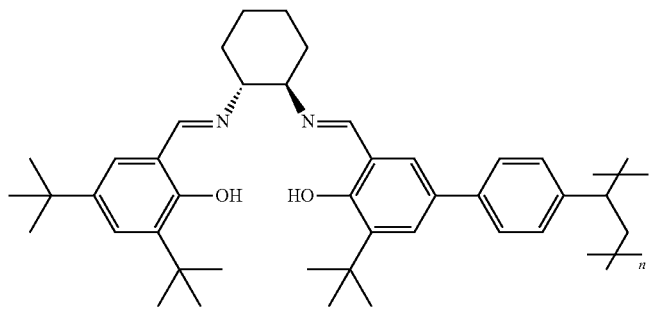

2: n = 12, 3: n = 18, 4: n = 24

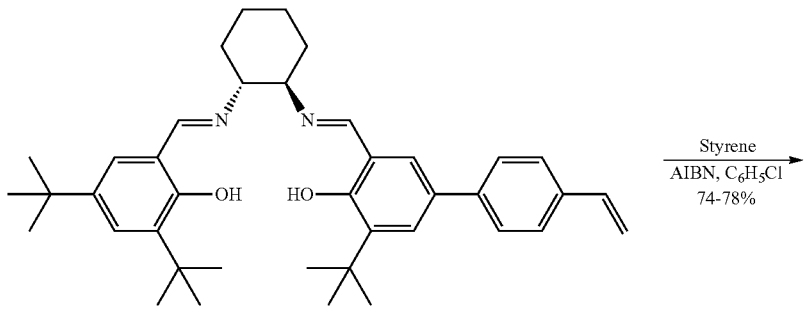

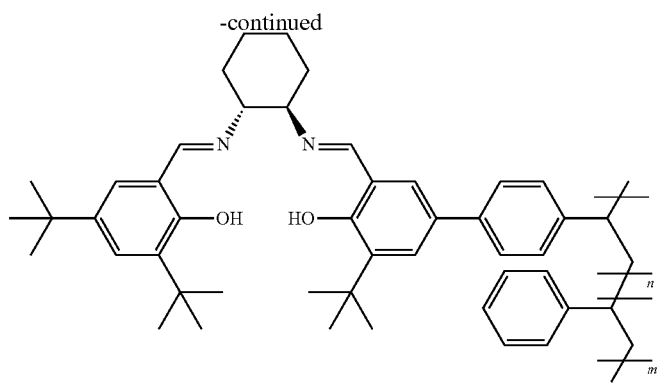
5: m/n = 1, 6: m/n = 4, 7: m/n = 9
Subsequent metalation with Co(OAc)₂ provided the metalated products as shown in Scheme 8, which products exhibited desirable catalytic properties in, for example, the hydrolytic kinetic resolution of racemic epichlorohydrin.
Scheme 8. Metalation of homopolymeric salen ligands and polystyrene-supported salen ligands.
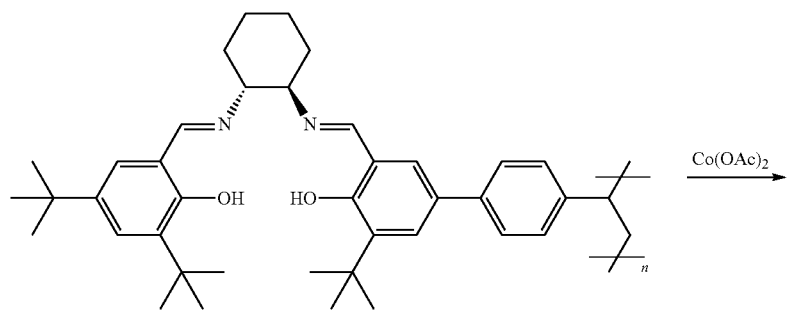
1
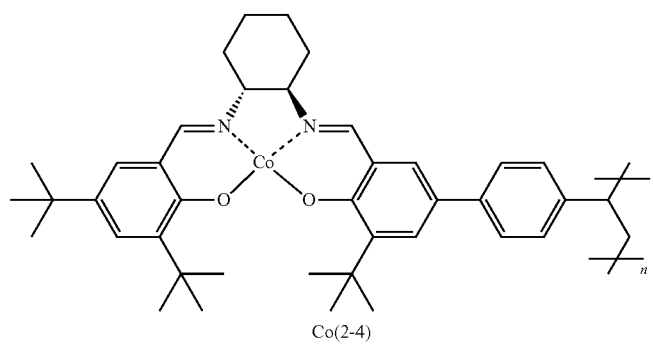
Co(2-4)

-continued

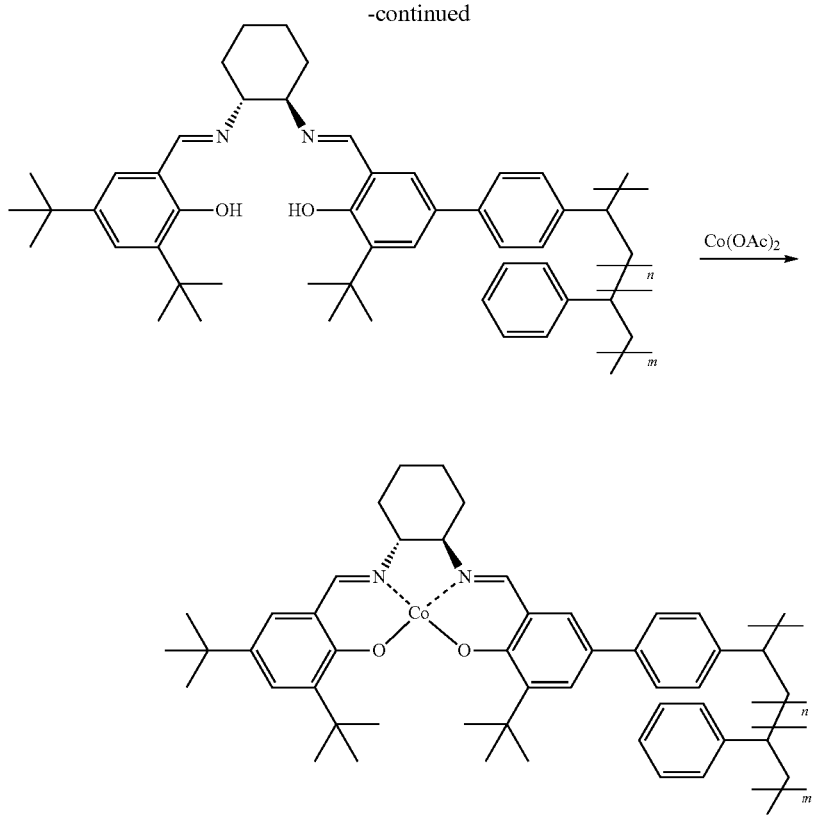

Co(5-7)

For example, a one-pot condensation reaction of (1R,2R)-1,2-diaminocyclohexane monohydrochloride salt, 3,5-di-t-butyl-2-hydroxybenzaldehyde, and 3-(4-vinylphenyl)-5-t-butyl-2-hydroxybenzaldehyde in a 1:1:1 ratio afforded the desired unsymmetrical mono-styryl substituted salen ligand (1) of Scheme 7 in 85% isolated yield. Free radical polymerization of 1 in the presence of various amounts of the initiator AIBN gave the corresponding homopolymers 2-4 with different chain lengths. Copolymerization of the styryl-salen and styrene in the absence or presence of divinylstyrene produced soluble linear copolymers (5-7) or insoluble cross-linked resins of Scheme 8, respectively. Metalation of the polymers and the copolymers of the styryl-salen with cobalt (II) acetate generated the corresponding polymer-supported cobalt-salen precatalysts (Co(2-7)) in quantitative yields with cobalt loadings of 0.38-1.53 mmol/g.

Synthesis of Oligomeric Co(Salen) Complexes Via Ring-Expanded Olefin Metathesis of Cyclooctene Substituted Salen Monomers.

As shown in Scheme 9, catalyst 4 was prepared on multi-gram scale from starting materials described above in Scheme 4. Treatment of the cyclooct-4-en-1-yl substituted unsymmetrical salen ligand 7 with Co(OAc)$_2$.4H$_2$O, produced the corresponding Co(II) complex 3 as a brick red solid. In the presence of 2-4 mol % of the third generation (3°) Grubbs catalyst 9, both 7 and 3 underwent the ring-expanding olefin metathesis in dichloromethane to give unsymmetrical oligomeric macrocycles 8 and 4, respectively. These ring-expanding reactions were found to be rather fast and clean. In situ $^1$H NMR revealed that the metathesis of 7 was complete in 20 min, as evidenced by the up-field shift of the alkenyl proton signals from 5.72 ppm for oligomer 7 to 5.42 ppm for oligomer 8 and line-broadening of almost all peaks. The oligomeric nature of 8 was verified by an analysis with the gel permeation chromatography (GPC) although the absolute value of the number-average molecular weight (M$_n$) would have a substantial error due to the lack of appropriate standards. However, the MALDI mass spectrometry provided unambiguous details of the structures of these oligomers at a molecular level. The spectrum of 4 (not shown) indicated the exclusive formation of oligomeric macrocycles as a mixture of predominantly dimeric to tetrameric species with observable traces of higher homologues up to a decamer (3: m/z=700, 4: m/z=1,400 (dimer), 2,099 (trimer), 2,799 (tetramer), and so forth). Furthermore, 4 can alternatively be prepared from the metalation of the oligomeric ligand 8 with Co(OAc)$_2$.4H$_2$O, and demonstrated an identical mass spectrum to that obtained from the metathesis route.

HKR of allyl glycidyl ether with polymeric co-salen catalysts was also evaluated. The resolution reactions were carried out at ambient temperature with 0.6 equiv of water and 0.01 mol % loading of catalysts calculated on the basis of cobalt. The resolution was completed in 12 h in the presence of 4 (OAc) as the catalyst as shown in Scheme 10. The remaining allyl glycidyl ether was determined by the chiral GC method to have an enantiomeric excess (ee) of over 99% in a conversion of 51%. Despite a brief induction period in the initial HKR, catalyst 4 (OTs) of Scheme 9 readily completed the resolution in 6 h with over 99% ee for the epoxide. In comparison, the monometallic unsupported complex 3 (OAc) gave less than 1% ee for the epoxide in 12 h, suggesting that complex 3 had little if any affect on the HKR of allyl glycidyl ether in such a low catalyst loading.

A number of other HKR examples were accomplished on various terminal epoxide substrates and the conditions and results are tabulated in Table 1.

Scheme 9. Synthesis of oligomeric salens and oligomeric Co(salen) complexes via ring-expanded olefin metathesis of cyclooctene substituted salen monomers.
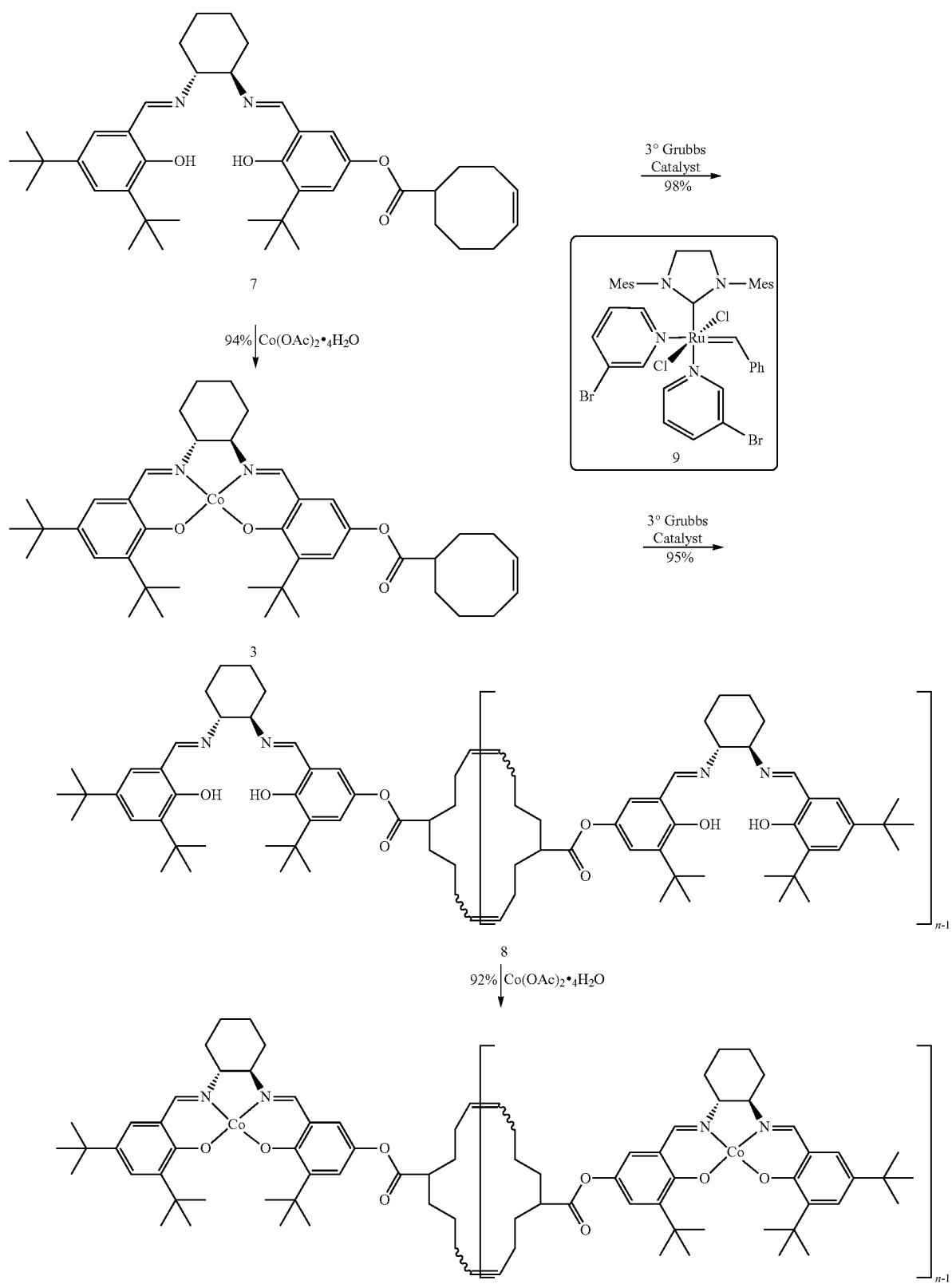

Supported Metal-Salen Catalyzed Preparative Processes

The cobalt-salen polymer supported catalysts were discovered to be useful as generally highly active for hydrolytic kinetic resolution (HKR) of terminal epoxides. The manganese-salen polymer supported catalysts were discovered to be useful as generally highly active for the asymmetric epoxidation (AE) of olefins. In embodiments, design criteria for salen polymer supported catalysts of the disclosure include: (i) the supported catalyst should possess an optimized salen ligand sphere, (ii) the salen ligand preferably can be attached to the support via a single linker (L') to minimize steric restrictions; (iii) for Mn-salen species, the catalyst loading should be sufficiently low to maximize site isolation of the catalytic centers to minimize the formation of catalytic inactive oxo-bridged dimers, whereas for Co-salen species, the active catalyst is preferably selected at a high enough density to permit the proposed simultaneous activation of epoxide and nucleophile via two different cobalt centers; and (iv) the morphology of the supports should ensure free access of reactants to all active sites. Accordingly, in embodiments, mono-functionalized salen cores were attached via a single site to a soluble poly(norbornene) backbone. For the attachment, chemically inert C—C bond linkages via a phenylene-acetylene linker were used and were found to minimize catalyst degradation during the epoxidation reactions. Variations of the catalyst active site density could be readily achieved by homo- or co-polymerizing metalated salen monomers having a polymerizable group by, for example, ROMP.

Hydrolytic Kinetic Resolution (HKR)

The oligo(cyclooctene)-supported Co(II)(salen) complex 4 of Scheme 9 was examined for catalytic efficiency in the HKR of terminal epoxides. Two methods were developed to generate the Co(III)(salen) species, the active catalytic species for the HKR, with different counterions. Method A involved the aerobic oxidation in the presence of an excessive amount of acetic acid. After the mixture was stirred in dichloromethane in the open air for 30 min, all volatiles were removed in vacuo to afford 4 (OAc) as a brown solid. Method B used 1.05 equiv of p-toluenesulfonic acid in THF as the acid reagent. The oxidation and workup under the similar conditions gave green 4 (OTs) as the crude catalyst. Both of these catalysts were highly soluble in common epoxides and enabled the resolution reactions to be performed neat.

In embodiments, the polymeric cobalt-salen catalysts of the disclosure were used in HKR of racemic substrates, such as rac-epichlorohydrin or allyl glycidyl ether as shown in Scheme 10. HKR of rac-epichlorohydrin was accomplished with, for example, 0.5% of the polymeric cobalt-salen catalyst of Scheme 8 and afforded the (S)-epichlorohydrin in 44% yield (88% theoretical yield) and >99% ee. The catalyst could be reused with almost identical reactivity and enantio-selectivity after isolation and reactivation.

Scheme 10. Hydrolytic kinetic resolution of substrates epichlorohydrin and allyl glycidyl ether.

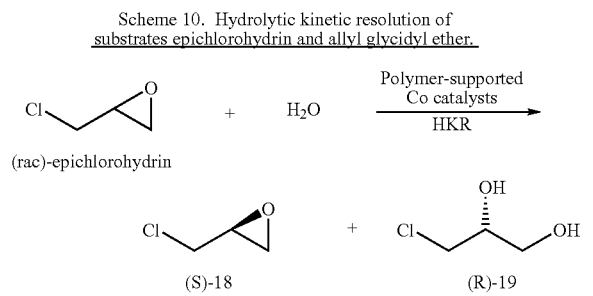

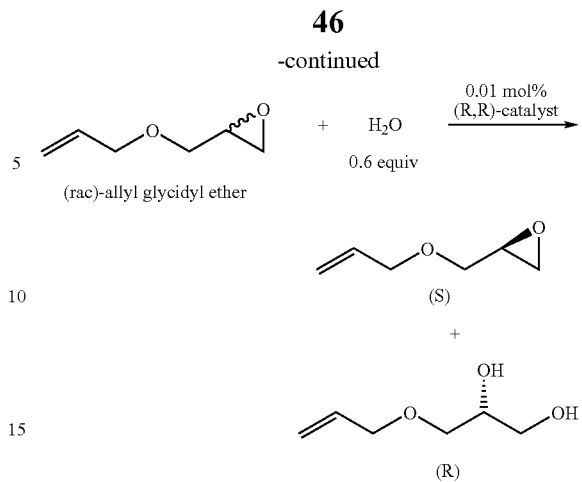

TABLE 1

Hydrolytic kinetic resolution of various terminal epoxides.[a]

| Entry | R | Method[b] | Loading (mol %) | Time (h) | ee[c] (%) | Yield[d] (%) |
|---|---|---|---|---|---|---|
| 1a | n-Bu | A | 0.01 | 2.0 | >99 | 43 |
| 2a | Cl | A | 0.01 | 2.5 | >99 | 44 |
| 2b | Cl | B | 0.01 | 2.5 | >99 | 43 |
| 3a | AllylOCH$_2$ | A | 0.01 | 12 | >99 | 48 |
| 3b | AllylOCH$_2$ | B | 0.01 | 6.0 | >99 | 46 |
| 4a | PhOCH$_2$ | A | 0.01 | 20 | >99 | 46 |
| 5a[e] | Ph | A | 0.1 | 24 | >99 | 45 |
| 5b | Ph | B | 0.1 | 18 | >99 | 48 |

[a] Reactions were performed on 0.05-0.1 mol scales under solvent-free (neat) conditions.
[b] Method A: 4(OAc) as the catalyst; Method B: 4(OTs) as the catalyst.
[c] Determined by chiral GC or HPLC methods.
[d] Isolated yield.
[e] 1 mol % (based on the epoxide) of HOAc was added.

Asymmetric Epoxidation

As shown in Scheme 11, the polymeric Mn-salen complexes were evaluated as asymmetric epoxidation catalysts. The olefins styrene 12, 1,2-dihydronaphthalene 14, and cis-β-methyl styrene 16, were selected as substrates, representing a terminal, a cyclic and a cis-disubstituted, non-cyclic olefin, respectively. Following published procedures, the polymeric catalysts of the present disclosure, N-methyl-morpholino-N-oxide (NMO), the olefin, and chlorobenzene or dodecane as an internal standard, were dissolved in methylene chloride, cooled the solutions to –20° C., and the peracid meta-chloroperoxybenzoic acid (m-CPBA) was added in three equal portions over a period of two minutes.

Scheme 11. Epoxidations of unfunctionalized olefins.

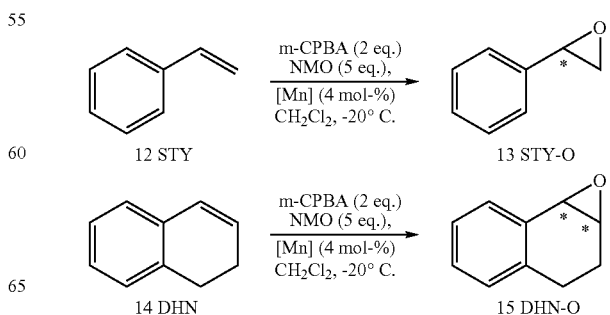

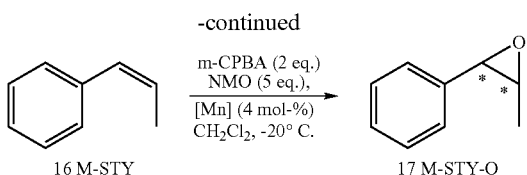

Kinetic studies of the reactions via GC-analysis showed the high activities of the polymer-supported Mn-salen catalyst systems of Scheme 5 with quantitative conversion using four mol % Mn after 150-300 seconds. The epoxidations of styrene 12 and cis-β-methyl styrene 16 were as fast as control experiments that used an original non-supported Jacobsen complex. Only in the case of 1,2-dihydronaphthalene 14, the epoxidation rate with p(9) is somewhat slower than the rate of the original Jacobsen-catalyst. The copolymer complexes p(9.11) had catalytic activities that were higher than the homopolymer complex analog p(9). All reactions are quantitative after five minutes or less, suggesting excellent substrate access to metal-complex catalytic sites. Table 2 lists additional results for catalytic epoxidation of olefins 12, 14, and 16.

TABLE 2

Epoxidation of unfunctionalized olefins. [1]

| Entry | Olefin [2] | Epoxide | Catalyst | Temp. (° C.) | Conv. (%) [3] | ee (%) |
|---|---|---|---|---|---|---|
| 1 | 12 | 13 | Jacobsen | −20 | 100 | 34 |
| 2 | 12 | 13 | p(9) | −20 | 100 | 32 |
| 3 | 12 | 13 | p(9.11)$_{11}$ | −20 | 100 | 33 |
| 4 | 12 | 13 | p(9.11)$_{13}$ | −20 | 100 | 32 |
| 5 | 12 | 13 | p(9.11)$_{19}$ | −20 | 100 | 33 |
| 6 | 14 | 15 | Jacobsen | −20 | 100 | 88 |
| 7 | 14 | 15 | p(9) | −20 | 100 | 76 |
| 8 | 14 | 15 | p(9.11)$_{11}$ | −20 | 100 | 81 |
| 9 | 14 | 15 | Cycle 2 | −20 | 100 | 47 |
| 10 | 14 | 15 | Cycle 3 | −20 | 85 | 6 |
| 11 | 14 | 15 | p(9.11)$_{13}$ | −20 | 100 | 81 |
| 12 | 14 | 15 | p(9.11)$_{19}$ | −20 | 100 | 82 |
| 13 | 16 | 17 | Jacobsen | −20 | 100 | 93 |
| 14 | 16 | 17 | p(9.11)$_{11}$ | −20 | 100 | 92 |

All epoxidations were carried out at −20° C.:
[1] with m-CPBA (2 eq.), NMO (5 eq.) and 4 mol-% Mn-catalyst in CH$_2$Cl$_2$.
[2] Styrene (STY) or 1,2-dihydronaphthalene (DHN).
[3] after five minutes.

The supported catalysts also had outstanding selectivities. For the epoxidation of styrene 12 and cis-β-methyl styrene 16 the enantiomeric excesses (ee's) are comparable to the unsupported Jacobsen catalyst (32-33% ee vs. 34% ee for 13 and 92% ee vs. 93% ee for 17). For the epoxidation of 1,2-dihydronaphthalene 14, the ee's with the polymeric catalysts are slightly lower than with the Jacobsen catalyst (76-82% ee vs. 88% ee) but among the highest ee's reported for any immobilized salen complexes (10-84% ee). Although not limited by theory, a possible reason for the somewhat lower selectivities of the presently disclosed supported systems is their slower reaction rate, which increases the amount of racemic epoxide produced by a slow background reaction without the need of a catalyst. As observed for the epoxidation rates, the enantioselectivities of the copolymers p(9.11) are very similar (81-82% ee) and higher than the homopolymer p(9) (76% ee), suggesting a good site-isolation of the manganese centers even for the 1:1-copolymer.

The polymeric Mn-complexes could be separated easily from the reaction mixtures by precipitation into Et$_2$O/MeOH and subsequent centrifugation. In all cases, the polymer catalyst was recovered quantitatively. In one study of the reusability, p(9.11)$_{11}$ was selected and represented the copolymer system with the best catalytic performance and the highest manganese loading. Unfortunately, after separating the polymer by precipitation, the residue was no longer completely soluble in methylene chloride. When the resulting suspension was used as a catalyst for the epoxidation of 14, the epoxidation rate was slower than the one with the non-recycled polymer. This drop of activity after recycling is even more pronounced in the third cycle, where only 85% conversion of 14 after 300 seconds was achieved. Even more dramatic was the decline of enantioselectivity from 81% ee over 47% ee (second cycle) to only 6% ee after the third cycle, demonstrating that p(9.11)$_{11}$ was not reusable. Whether the observed reduced solubilities and the subsequent drops in activity and selectivity are a result of the dimerization of Mn(III)- and Mn(V)=O centers (i.e., leading to cross-links between different polymer chains), or a degradation/chemical modification of the catalyst, i.e., the backbone olefins of the poly(norbornene)s could be crosslinked or epoxidized, remains uncertain.

The results with the Mn-poly(norbornene)s as chiral epoxidation catalysts clearly reveal that by following the above described criteria, immobilized catalysts with outstanding activities and selectivities that are comparable with the catalytic activities and selectivities of the original non-polymeric Jacobsen catalyst, can be prepared and utilized. Furthermore, the polymeric Mn-salen complexes can be easily removed by precipitation and subsequent centrifugation allowing for the removal of the vast majority of the metal species after complete reactions.

Similarly, the polymeric Co-catalysts of the disclosure can be easily and readily removed or separated from a reaction mixture and desired reaction products. The separated polymeric cobalt-salen catalysts can be reused or recycled, for example, at least once in a second reaction with high retention of activity and selectivity. Although not limited by theory, the effect of the linker group (L') and polymer backbone flexibility on the activity and selectivity of immobilized metal-salen catalysts is believed to be significant in bi-metallic processes with polymeric Co-catalysts, and less significant or insignificant in mono-metallic processes with polymeric Mn-catalysts.

Experimental Section

All reactions with air- and moisture sensitive compounds were carried out under an argon atmosphere using standard Schlenk techniques. Diethylether (Et$_2$O), tetrahydrofuran (THF), methanol (MeOH) and ethanol (EtOH) were distilled over sodium/benzophenone, and dichloromethane (CH$_2$Cl$_2$) and triethylamine (NEt$_3$) were distilled over calcium hydride and stored in dry Schlenk-flasks under argon. All other reagents and solvents were purchased from commercial sources and used as received unless otherwise noted.

Gas-chromatographic analyses were performed on a gas chromatograph equipped with a flame-ionization detector and a HP-5 column (30 m×0.25 mm×0.25 μm). The temperature program for GC analysis was as follows: 2 min. 50° C. followed by heating to 140° C. at 30K/min and heating to 300° C. at 40 K/min under constant pressure with inlet and detector temperatures kept constant at 330° C. The enantiomeric excess of the epoxides of styrene 12, 1,2-dihydronaphthalene 14 and cis-β-methylstyrene 16 were determined using a GC-MS with a Dex 120 column (30 m×0.25 mm×0.25 μm). The temperature programs were as follows: for Sty-O 13: 80° C. for 50 min, 20 K/min to 200° C. (t$_R$(first enantiomer)=46.3 min, t$_R$(second enantiomer)=49.5 min); for DHN—O 15: 125° C. for 40 min, 20 K/min to 205° C. (t$_R$(first enantiomer)=

34.9 min, $t_R$(second enantiomer)=36.8 min); for MSty-O 17: 90° C. for 40 min, 20 K/min to 190° C. ($t_R$(first enantiomer)= 33.3 min, $t_R$(second enantiomer)=36.4 min).

Kinetics and selectivities of the hydrolytic kinetic resolution of epichlorohydrin 18 was analyzed on a GC-FID with a γ-TA column (30 m×0.25 mm×0.25 μm). The temperature was kept at 60° C. for 15 min followed by heating at 10 K/min to 160° C. ($t_R$(S-18)=10.2 min, $t_R$(R-18)=11.7 min, $t_R$(diol R-19)=25.1 min).

NMR spectra were recorded on a 300 MHz or a 500 MHz instrument. Chemical shifts (ppm) of $^1$H- and $^{13}$C-spectra are referenced to residual solvent signals as internal standards. The fine structure of the proton signals were specified with "s" (singlet), "d" (doublet), "t" (triplet), "q" (quartet), "m" (multiplet), "dd" (double-doublet) and "br s" (broad singlet).

Gel-permeation Chromatography analyses (GPC) were carried out using a binary pump coupled to a refractive index detector. The GPC was calibrated using poly(styrene) standards using a column set with $CH_2Cl_2$ as the eluent.

Column-chromatography was carried out on technical grade silica gel (60 Å, 40-63 μm) at a pressure of ca. 50 kPa.

Polymer Characterization Although the metal complexes 9 and 10 are paramagnetic, it was possible to investigate the polymerization rates using $^1$H-NMR spectroscopy by solely focusing on the signals of the olefin protons. In all cases, monomer conversions (monomer to catalyst ratios up to 100: 1) were quantitative after one to two hours. Moreover, following the homopolymerizations of ten equivalents of 9, 10 or 11 by $^1$H-NMR, it was found that the polymerization kinetics of all three monomers using the 3°-generation Grubbs catalyst were similar with complete monomer-conversion after about 2-5 minutes. These results suggest that the copolymerization of 9 and 11 and 10 and 11 yield statistical copolymers p(9.11) and p(10.11), i.e., the monomers containing the catalytic moiety are randomly dispersed within the alkyl-norbornene matrix.

It is well known that polyelectrolyte and metal-salt containing polymers cannot be characterized by gel-permeation chromatography (GPC), most likely due to interactions of the polymers with the packing material and the formation of aggregates during the process. The same limitation holds true for the present metal-containing polymers and no GPC results of any polymer containing more than ten repeating units could be obtained in either THF, chloroform, or methylene chloride. Therefore, no polydispersities (PDIs) or molecular weights for the high molecular weight polymers are included. However, the values for the molecular weights and the polydispersities of p(9) ($M_w$=5,900, $M_n$=4,400, PDI=1.34) and p(10) ($M_w$=55,400, $M_n$=18,300, PDI=3.03) confirmed a successful and quantitative ROMP of the monomeric complexes.

Three different analysis methods were used to determine the metal contents of all monomers and polymers. First, all compounds were ICP. Second, the C, H, N, and O-contents were analyzed by elemental analysis. Since the monomers contain only the elements C, H, N, and O but for the metal and its ligands (such as chlorine, etc.) one can calculate the metal content by subtracting the C, H, N, O— (and in case of the Mn-complexes Cl) contents from 100 percent. The remaining contents are the metal complex. The results of these two methods are shown in Table 3.

TABLE 3

Elemental analysis and ICP-data of the polymers.

| | | %-found/(%-calcd.) | | | | | |
|---|---|---|---|---|---|---|---|
| Entry | Polymer | C [1] | H [1] | N [1] | O [1] | Cl/S [2] | Me [3] | Me [4] |
| 1 | p(9) | 68.67 | 7.02 | 3.27 | 9.09 | n.d. [5] | 11.95[6] | 5.00 |
| | | (70.71) | (6.92) | (3.44) | (7.85) | — | (11.09) | (6.74) |
| 2 | p(9.11)$_{11}$ | 71.10 | 7.65 | 2.64 | 9.72 | 2.26 | 5.68 | 4.68 |
| | | (72.13) | (7.78) | (2.63) | (9.01) | (3.33) | (5.15) | (5.15) |
| 3 | p(9.11)$_{13}$ | n.d. [5] | n.d. [5] | n.d. [5] | n.d. [5] | n.d. [5] | n.d. [5] | 3.86 |
| | | | | | | | | (3.51) |
| 4 | p(9.11)$_{19}$ | 75.05 | 9.63 | 0.84 | 11.69 | 0.96 | 1.83 | 1.39 |
| | | (75.15) | (9.53) | (0.91) | (11.47) | (1.16) | (1.79) | (1.79) |
| 5 | 10 | 73.33 | 7.21 | 3.49 | 8.33 | — | 7.64 | 8.00 |
| | | (73.54) | (7.20) | (3.57) | (8.16) | — | (7.52) | (7.52) |
| 6 | p(10) | 71.06 | 7.06 | 3.57 | 8.95 | — | 9.36 | 6.96 |
| | | (73.54) | (7.20) | (3.57) | (8.16) | | (7.52) | (7.52) |
| 7 | p(10.11)$_{11}$ | 72.88 | 7.89 | 2.76 | 9.89 | — | 6.58 | 5.96 |
| | | (74.32) | (7.99) | (2.71) | (9.28) | | (5.70) | (5.70) |
| 8 | p(10.11)$_{13}$ | 74.25 | 8.73 | 1.95 | 11.15 | — | 3.92 | 3.95 |
| | | (75.11) | (8.80) | (1.82) | (10.42) | | (3.84) | (3.84) |
| 9 | p(10.11)$_{19}$ | 75.50 | 9.50 | 0.90 | 11.96 | — | 2.14 | 2.02 |
| | | (75.92) | (9.62) | (0.92) | (11.59) | | (1.94) | (1.94) |
| 10 | p(10c) | 65.42 | 6.79 | 2.60 | 15.02 | 3.97 | 6.20 | 5.60 |
| | | (69.16) | (6.65) | (2.93) | (11.73) | (3.36) | (6.17) | (6.17) |
| 11 | p(10c)_rec | 57.65 | 6.27 | 2.58 | 20.47 | 5.10 | 7.93 | 4.27 |
| | | (69.16) | (6.65) | (2.93) | (11.73) | (3.36) | (6.17) | (6.17) |

[1] Determined by elemental analysis.
[2] Determined by elemental analysis, S only for p(10c.11) and p(10c.11)_rec (entry 10, 11).
[3] Determined by 100 − (sum of percentages of other elements).
[4] Determined by ICP.
[5] Not determined due to lack of sample material.
[6] Content of MnCl, determined by 100 − (sum of percentages of other elements).

Finally, where possible, the chlorine content of all polymers was determined. The manganese compounds generally contain one Cl ligand on all metals. Therefore, by analyzing the chlorine content, one can calculate the metal content. Using this methodology, the manganese contents of p(9.11)$_{11}$ was calculated to be 3.50% (calcd. 5.15%) and that of p(9.11)$_{19}$ to be 1.48% (calcd. 1.79%). While one should expect these three methods to agree in the metal contents, it was found that all three methods slightly diverge from the theoretical expected metal values (some methods suggest a higher metal content while others suggest a lower one), which is attribute to the error of the three analytical methods due to the small sample sizes and the low metal percentage of all polymers. With these limitations in mind, the values for the metal loadings of the polymers are within the error range (in most cases ±0.5% for all three methods) in good agreement with the theoretical values. These results suggest that the metalated salen complexes do not decompose during the ROMP. It is important to note that always fully characterized and purified, i.e., by column chromatography, metalated monomers were employed during the ROMP, and that the co-monomer ratios are approximately the same as the theoretical targeted ratios.

Hydrolytic Kinetic Resolution Reaction Analysis The catalytic performance of the polymeric cobalt complexes p(10) and p(10.11) were studied in the HKR of racemic epichlorohydrin (ECH) 18 (Scheme 10). Since only the Co(III) complexes are catalytically active in this reaction, we oxidized the obtained Co(II) polymers p(10) and p(10.11) were oxidized by stirring methylene chloride solutions of the polymers with acetic acid under an atmosphere of air (X=OAc). After removal of the solvent and the excess AcOH in vacuo, the desired Co(III)-salen polymers p(10a) and p(10a.11) with acetates as counterions were obtained. For the HKR reactions, the Co(III)-polymers were dissolved in a mixture of methylene chloride, 18, and chlorobenzene as an internal standard, followed by the addition of 0.7 equivalents of water to start the resolution. The addition of some methylene chloride as a solvent was necessary because the copolymers were not fully soluble in 18. Similar procedures were used to obtain p(10b)(X=I) and p(10c)(X=OTs).

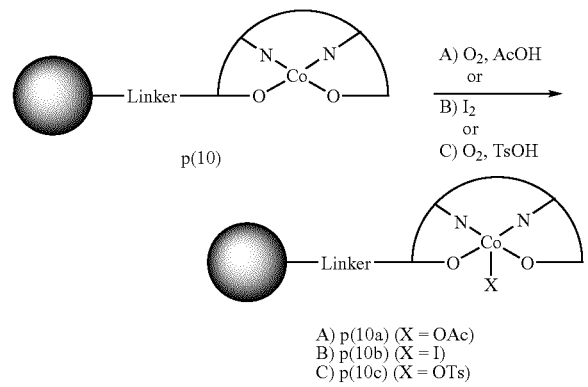

The reaction kinetics of the HKR were studied via chiral GC-analysis. Using either the homopolymer p(10a) (X=OAc) or the two copolymers p(10a.11)$_{11}$ and p(10a.11)$_{13}$, epoxide (R)-18 was fully converted after five hours to its corresponding diol, leaving pure (S)-18 in the reaction mixture in above 99% enantiomeric excesses. After this time period, 55% of the racemic 18 is converted, i.e., all of the unwanted R enantiomer is converted to the diol while only 5% of the desired epoxide has been converted, indicating selectivities similar to the original Jacobsen CoOAc catalyst (53% conversion, >99% ee under solvent-free conditions). The epoxidation rates with p(10a.11)$_{11}$ and p(10a.11)$_{13}$ are slightly higher than the ones using p(10a). This finding, at first impression contradicts the assumption of a bimetallic mechanism for the HKR, and may be the result of a higher backbone flexibility of the copolymers in comparison to the sterically more congested homopolymers. However, further dilution of the salen-moieties along the polymer backbone (polymers p(10a.11)$_{19}$) resulted in a dramatic drop of the activity (only 43% conversion and 80% ee after five hours), while the selectivities remained the same (e.g., p(10a.11)$_{11}$: 44.5% conv., 78.4% ee and p(10a.11)$_{13}$: 45.5% conv., 81.0% ee after one hour). This result suggests that the extreme dilution of the catalytic moieties along the polymer backbone results in the deactivation of the catalysts due to the unlikelihood of two catalytic moieties being in close proximity to each other, a prerequisite for the bimetallic catalytic pathway.

Using p(10a), the HKR of 18 can also be carried out under solvent-free conditions. In this case, the reaction rates are faster than the rate with p(10a) using $CH_2Cl_2$ as the solvent as well as the rate of the original Jacobsen complex, resulting in (S)-18 with >99% ee after less than two hours. However, an increase in conversion (62%) suggests that the polymeric catalyst is less selective under these reaction conditions. When comparing the kinetics of the non-polymeric Jacobsen CoOAc-salen catalyst (X=OAc) of the formula:

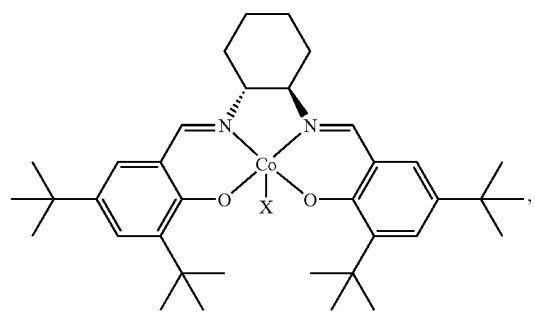

with the monomeric catalysts 10a, it was found that 10a is slightly less selective than the Jacobsen catalyst indicating that the lower selectivity of the polymers are primarily a result of the different catalyst structure (phenylene-acetylene linker instead of a tert-butyl group in the 5-position of one of the aromatic rings) and not based on the polymeric support. This result suggests that even small changes in the structure of the salen core can have a significant effect on the catalytic properties of the resulting complexes.

Another important variable that has been studied with Co-salen catalysts is the choice of the counterion on the metal center. It has been reported that very nucleophilic counterions like Cl can attack the epoxide very fast resulting in small amounts of byproduct, while catalyst activity can be increased dramatically with more electronegative counterions, such as —OTs, and like counterions. Finally, non-coordinating counterions like $PF_6^-$ or $BF_4^-$ can suppress the undesired reduction of Co(III) to Co(II). To investigate if this counterion effect holds true in the present polymeric system and to investigate whether changes to counterion of the polymeric catalyst can be used to control their activities and selectivities, polymers p(10b) and p(10c) were prepared with iodide and tosylate counterions, respectively. Polymer p(10b) was obtained by oxidizing 10 with iodine and subsequent ROMP of 10•I. In contrast, p(10c) (X=OTs) was obtained by oxidizing the polymer p(10) with $O_2$/p-toluenesulfonic acid. Interestingly, when either p(10b) or p(10c) were employed as catalysts in the HKR of 18 under solvent-free conditions, both catalysts showed higher activities than p(10a). In particular p(10b) was highly active, with (S)-18 being obtained in >99% ee after less than one hour. However, the selectivities of p(10b) and p(10c) are somewhat lower than that of p(10a) (conversions for obtaining (S)-18 with >99% ee: 66.7% using p(10b), 69.7% using p(10c) and 62.0% using p(10a)). These results demonstrate that a counterion effect exists for the polymer-supported Co-salen catalysts of the present disclosure.

As a result of the outstanding activities of p(10c), this polymeric catalyst was used to optimize other reaction conditions. In an attempt to improve selectivities, $CH_2Cl_2$ was added to the reaction as a solvent. Unfortunately, the reaction was significantly slower with only about 49.0% 18 converted after 11.5 hours (87.9% ee of (S)-18). Nevertheless, higher enantiomeric excess of (S)-18 at 50% conversion observed under these reaction conditions indicate an increase in selectivity of p(10c) when a solvent is added. The effect of decreasing catalyst loading on the activities and the selectivities was also investigated. When the catalyst loading of the polymeric CoOTs-catalyst was decreased to 0.2 mol-% Co for the HKR of 18, a decrease in activity (the reaction took eleven hours for a complete conversion of (R)-18) and a decrease in selectivity were observed (after 11 hours, 67.2% of the racemic epoxide was converted). Moreover, a comparison of the enantiomeric excess of the remaining (S)-18 at similar conversions suggested an increased selectivity with a decrease of the CoOTs-amount (0.2 mol-% p(10c): 47.4% conv., 78.2% ee, 0.5 mol %:51.4% conv., 64.4% ee). These results demonstrate that for the CoOTs-poly(norbornene) catalyst the use of less catalyst loading can be advantageous in embodiments.

All polymeric Co-complexes could be easily separated from the reaction mixtures by precipitation into $Et_2O$ and subsequent centrifugation. By simply washing the obtained $Et_2O$-solution with water (R)-3-chloro-1,2-propanediol 19 was removed nearly quantitatively resulting in pure (S)-18. This protocol is considered to be an important advantage to the normally used methodology of distilling off 18 from the crude reaction mixture since remaining Co(III)-salen complexes are reported to catalyze the decomposition and the racemization of the epoxide during the purification process. Since the polymeric Co-OAc complex p(10a) gave the best selectivities, this catalyst was selected to study the reusability of polymeric Co-salen catalysts. After re-oxidation with $O_2$ in the presence of acetic acid, recycled p(10c) showed the same resolution rate and selectivities as the original polymeric catalyst p(10c) (i.e., 61.8% conv.>99% ee of (S)-18 after 150 min) However, the need of ultra-sonication in order to dissolve p(10a) fully in a solution of 18 and chlorobenzene before the catalysis indicated reduced solubility. The solubility of the polymeric catalyst declined further for the third catalytic cycle. It was not possible to dissolve the twice-recycled p(10a) fully in the reaction mixture, even after the addition of $CH_2Cl_2$ as solvent and ultra-sonicating the mixture. As a result of the lower solubility, the reaction rate dropped for the third cycle with only 78.8% ee after three hours (49.6% conversion). However, after 11 hours 61.0% of the racemic epoxide was converted and (S)-18 was obtained with 97.8% ee, indicating that the polymeric catalyst was still active and very selective, and that after an appropriate reaction time enantiomerically pure (S)-18 could be isolated in good yields. Similar results for the reusability (i.e., the solubility problems and subsequent low resolution rates) were obtained with the polymeric Co-OTs-salen p(10c). Analysis of p(10c) by ICP before starting the recycling experiments and after the third catalysis cycle showed that the metal content of the polymer decreased from 5.60% to 4.27%. This decrease in metal content cannot be explained with the error range of the elemental analysis. Since a leaching of metallic cobalt has not been reported in the literature, it is suggested that this slight decrease in metal content may be due to a cleavage of the ester bonds resulting in a loss of a complete salen moiety from the polymer. Accordingly, more chemically robust or inert Z connector groups are suggested, such as a —$CH_2$— or —Ar— in place of —C(=O)O—. Nevertheless, in a recent report on the stability of the norbornene ester linkages under a variety of reaction conditions, one cannot completely rule out (although unlikely) some metal leaching of the cobalt from the polymer. Additionally, the percentages of carbon, oxygen, and sulfur increased, indicating that either para-toluenesulfonic acid is not completely separated during the precipitation or that the acid may be reacting with the double bond along the polymer backbone.

A second recycling method in the literature involves removal of the substrates by fractionated distillation followed by the addition of more starting material to the metal containing residue. While this method suggests repeated usability of the Co-catalysts, it has several disadvantages including the potential for the undetected decomposition of the catalyst (i.e., leaching of cobalt) and that epoxides such as (S)-18 may racemize during this process. However, because of the solubility-issues encountered during the separation of the catalyst by precipitation, this recycling method was also investigated whereby $CH_2Cl_2$ was also used as a solvent. Starting with 11 mg p(10a) in the first cycle, 56 mg of an red-brown solid were obtained after distilling off $CH_2Cl_2$, (S)-18 and 19. Subsequently, the residue was dried in vacuo and the Co(II)-complex reoxidized with $O_2$/AcOH. The increased mass indicates an incomplete removal of the substrates, in particular 3-chloro-propane-1,2-diol (boiling point 213° C.). The recycled polymeric catalyst showed a somewhat lower activity in the second cycle. It took eleven hours instead of five to obtain (S)-18 with >99% ee (57% conv.). After recycling and reoxidation, 99 mg of a brown residue were isolated after the second catalysis cycle. In the third cycle this residue showed a catalytic performance that was comparable to the one described for the second cycle. Interestingly, no solubility problems were observed using this methodology in contrast to the results with the precipitation method. Thus, the method of recycling selected may be an important factor in determining the properties and performance of a recycled catalyst.

The polymeric cobalt-salen results demonstrate a highly active and selective supported cobalt salen catalyst. Furthermore, copolymer complexes were slightly more active than their homopolymer analogs. Finally, a counterion effect was observed in the present supported catalyst systems that enable a tailoring of their activities and selectivities. The present supported catalysts can be easily removed from the reaction mixture and allow for the easy removal of metal species from the product. However, using the precipitation method, the supported catalysts were recycled once as a result of their decreased solubility after the reoxidation step.

Preparation of Starting Materials
(R,R)-N-(3,5-Di-tert-butylsalicylidene)-N'-[3-tert-butyl-5-(4'-hydroxyphenylethynyl)salicylidene]-1,2-cyclohexanediamine (4a) (Scheme 2)

(R,R)-1,2-Diaminocyclohexane mono(hydrogen chloride) (108 mg, 0.72 mmol), 3,5-di-tert-butyl-2-hydroxybenzaldehyde (168 mg, 0.72 mmol), and 4 Å molecular sieves (100 mg) were charged into a 25 mL flask equipped with a magnetic stir bar and a septum. Anhydrous ethanol (3 mL) and anhydrous methanol (3 mL) were added and the bright yellow solution was stirred at room temperature for four hours. A solution of 5-(4'-hydroxyphenylethynyl)-3-tert-butyl-2-hydroxy-benzaldehyde (211 mg, 0.72 mmol) in anhydrous $CH_2Cl_2$ (6 mL) and anhydrous $NEt_3$ (0.20 mL, 1.44 mmol) were added. The red solution was stirred at room temperature for additional four hours. The reaction mixture was filtered through a short pad of dry silica gel and the silica gel was flushed with $CH_2Cl_2$. The solvent was removed under reduced pressure. The residue was purified by column chromatography on silica gel (ethyl acetate/hexanes=1:5) to afford 4a (323 mg, 75%) as a yellow-orange powder. $R_F$ (SiO$_2$, ethyl acetate/hexanes=1:5)=0.13. $[\alpha]^{20}_D$-136° (c 0.5, DCM). $^1$H NMR (500 MHz, CDCl$_3$): δ=1.26 (s, 9H), 1.44 (s, 9H), 1.46 (s, 9H), 1.40-1.53 (m, 2H), 1.82-1.93 (m, 2H), 1.66-1.81 (m, 2H), 1.93-2.05 (m, 2H), 3.25-3.77 (m, 4H), 6.81 (d, J=8.7 Hz), 7.00 (d, J=2.5 Hz), 7.19 (d, J=2.0 Hz, 1H), 7.35 (d, J=2.5 Hz, 1H), 7.40 (d, J=8.7 Hz, 2H), 7.41 (d, J=2.0 Hz, 1H), 8.22 (s, 1H), 8.28 (s, 1H). $^{13}$C NMR (125 MHz, CDCl$_3$): δ=24.4, 29.4, 29.6, 31.5, 33.1, 33.2, 35.0, 34.2, 35.1, 72.0, 2.2, 87.2, 88.3, 112.5, 115.7, 115.6, 117.7, 118.4, 126.1, 127.3, 132.7, 133.1, 133.2, 136.7, 137.9, 140.1, 155.7, 158.4, 161.5, 165.2, 166.2. MS (ESI): m/z ($I_{rel}$)=607 (56, [M+1]$^+$), 291 (84, C$_{25}$H$_{31}$N$_2$O$_2$$^+$). HRMS (ESI) calcd for C$_{40}$H$_{51}$N$_2$O$_3$ ([M+1]$^+$): 607.3899. found: 607.3888. Anal. Calcd for C$_{40}$H$_{50}$N$_2$O$_3$ (606.38): C, 79.17; H, 8.30; N, 4.62; O, 7.91. found: C, 78.61; H, 8.26; N, 4.63; O, 8.03.

(R,R)-N-(3,5-Di-tert-butylsalicylidene)-N'-[5-(4'-acetylsulfanylphenylethynyl)-3-tert-butylsalicylidene]-1,2-cyclohexanediamine (4b) (Scheme 2)

(R,R)-1,2-Diaminocyclohexane mono(hydrogen chloride) (128 mg, 0.85 mmol), 3,5-di-tert-butyl-2-hydroxybenzaldehyde (199 mg, 0.85 mmol), and 4 Å molecular sieves (100 mg) were charged into a 25 mL flask equipped with a magnetic stir bar and a septum. Anhydrous ethanol (3 mL) and anhydrous methanol (3 mL) were added and the bright yellow solution was stirred at room temperature for four hours. A solution of 3-tert-butyl-5-(4'-acetylsulfanylphenylethynyl)-2-hydroxybenzaldehyde (300 mg, 0.85 mmol) in anhydrous CH$_2$Cl$_2$ (6 mL) and anhydrous NEt$_3$ (0.27 mL, 1.9 mmol) were added. The red solution was stirred at room temperature for additional four hours. The reaction mixture was filtered through a short pad of dry silica gel and the silica gel was flushed with CH$_2$Cl$_2$. The solvent was removed under reduced pressure. The residue was purified by column chromatography on silica gel (ethyl acetate/hexanes=1:10) to afford 4b (339 mg, 60%) as a yellow powder. $R_F$ (SiO$_2$, ethyl acetate/hexanes=1:5)=0.47. $[\alpha]^{20}_D$-144° (c 0.5, DCM). $^1$H NMR (300 MHz, CDCl$_3$): δ=1.24 (s, 9H), 1.42 (s, 9H), 1.43 (s, 9H), 1.43-1.60 (m, 2H), 1.84-1.94 (m, 2H), 1.66-1.83 (m, 2H), 1.94-2.08 (m, 2H), 2.43 (s, 3H), 3.24-3.44 (m, 2H), 6.96 (d, J=2.4 Hz, 1H), 7.21 (d, J=2.0 Hz, 1H), 7.32 (d, J=2.4 Hz, 1H), 7.37 (d, J=8.4 Hz, 2H), 7.40 (d, J=2.4 Hz, 1H), 7.51 (d, J=8.4 Hz, 1H), 8.26 (s, 4H), 8.28 (s, 4H), 13.60 (br s, 1H), 14.33 (br s, 1H). $^{13}$C{$^1$H}NMR (75 MHz, CDCl$_3$): δ=24.4, 29.3, 29.6, 30.4, 31.6, 33.1, 33.3, 34.2, 35.0, 35.1, 72.4, 72.5, 86.7, 91.6, 111.9, 117.8, 118.6, 125.2, 126.0, 127.1, 127.5, 132.1, 134.3, 132.7, 133.5, 136.6, 137.9, 140.2, 158.0, 161.5, 165.0, 166.2, 193.8. MS (ESI): m/z ($I_{rel}$)=665 (59, [M+1]$^+$), 449 (69, C$_{27}$H$_{33}$N$_2$O$_2$S$^+$), 331 (100, C$_{21}$H$_{35}$N$_2$O). Anal. Calcd for C$_{42}$H$_{52}$N$_2$O$_3$S (664.37): C, 75.86; H, 7.88; N, 4.21; O, 7.22. found: C, 75.79; H, 7.93; N, 4.06; O, 7.19.

(R,R)-N-(3,5-Di-tert-butylsalicylidene)-N'-[3-tert-butyl-5-(4'-vinylbenzene)salicylidene]-1,2-cyclohexanedediamine (4c)(Scheme 2)

A 250 mL flask was charged with (1R,2R)-1,2-diaminocyclohexane monohydrochloride salt (1.51 g, 10 mmol), activated 4 Å molecular sieves (4.0 g), anhydrous methanol (40 mL), and anhydrous ethanol (40 mL). 3,5-Di-tert-butyl-2-hydroxybenzaldehyde (2.34 g, 10 mmol) was added in one portion and the reaction mixture was stirred at room temperature for four hours. After complete consumption of the aldehyde as monitored by the TLC, a solution of 3-tert-butyl-2-hydroxy-5-(4'-vinylphenyl)benzaldehyde (2.74 g, 10 mmol) in dichloromethane (80 mL) was added to the reaction system, followed by the slow addition of triethylamine (2.8 mL, 20 mmol). The reaction mixture was stirred at room temperature for additional four hours followed by the removal of the solvents. The residue was dissolved in dichloromethane (100 mL), washed with aqueous hydrochloric acid (1 M, 50 mL) and water (2×50 mL), and dried with magnesium sulfate. Flash chromatography of the crude product with (ether/hexanes=1:50) afforded 4c (5.05 g, 85%) as a yellow solid. Mp: 177-178° C.; $[\alpha]^{20}_D$-156° (c 0.5, DCM). $^1$H NMR (400 MHz, CDCl$_3$): δ=1.22 (s, 9H), 1.42 (s, 9H), 1.44-1.51 (m, 2H), 1.46 (s, 9H), 1.70-1.84 (m, 2H), 1.88-1.91 (m, 2H), 1.97-2.02 (m, 2H), 3.30-3.38 (m, 2H), 5.25 (d, J=11.0 Hz, 1H), 5.77 (d, J=17.6 Hz, 1H), 6.74 (dd, J=11.0, 17.6 Hz, 1H), 6.97 (d, J=2.5 Hz, 1H), 7.21 (d, J=2.5 Hz, 1H), 7.31 (d, J=2.5 Hz, 1H), 7.40-7.45 (m, 4H), 7.49 (d, J=2.5 Hz, 1H), 8.30 (s, 1H), 8.35 (s, 1H), 13.69 (s, br, 1H), 14.01 (s, br, 1H). $^{13}$C{$^1$H}NMR (100 MHz, CDCl$_3$): δ=24.5, 24.6, 29.5, 29.6, 31.6, 33.3, 33.4, 34.2, 35.1, 35.2, 72.6, 113.6, 118.0, 119.0, 126.2, 126.7, 126.9, 127.1, 128.2, 128.3, 130.5, 136.0, 136.6, 136.7, 137.8, 140.2, 140.7, 158.2, 160.2, 165.8, 166.2. IR: ν=3082, 2999, 2952, 2933, 2860, 1628, 1467, 1440, 1390, 1271, 1252, 1171, 840 cm$^{-1}$. UV-vis (THF): λ=262, 300, 340 nm. MS (FAB): m/z ($I_{rel}$)=592 (100, M$^+$). Anal. Calcd for C$_{40}$H$_{52}$N$_2$O$_2$ (592.85): C, 81.04; H, 8.84; N, 4.73. found: C, 81.06; H, 8.95; N, 4.72.

(R,R)-N-(3,5-Di-tert-butylsalicylidene)-N-[3-tert-butyl-5-(hydroxymethyl)salicylidene]-1,2-cyclohexanedediamine (4d)(Scheme 2)

A 100 mL flask was charged with (1R,2R)-1,2-diaminocyclohexane monohydrochloride salt (151 mg, 1.0 mmol), activated 4 Å molecular sieves (200 mg), and anhydrous methanol (10 mL). 3,5-Di-tert-butyl-2-hydroxybenzaldehyde (234 mg, 1.0 mmol) was added in one portion and the reaction mixture was stirred at room temperature for four hours. A solution of 3-tert-butyl-2-hydroxy-5-(hydroxymethyl)benzaldehyde (208 mg, 1.0 mmol) in dichloromethane (10 mL) was added to the reaction mixture, followed by the slow addition of triethylamine (0.27 mL, 2.0 mmol). The reaction mixture was stirred at room temperature for additional four hours followed by the removal of the solvents. The residue was dissolved in dichloromethane (20 mL), washed with water (2×20 mL), and dried with magnesium sulfate. Flash chromatography of the crude product on silica gel (ether/hexanes=1:4 to 1:1) afforded 4d (0.39 g, 75%) as a light yellow solid. $[\alpha]^{20}_D$-318° (c 0.5, DCM). $^1$H NMR (400 MHz, CDCl$_3$): δ=1.23 (s, 9H), 1.41 (s, 9H), 1.42 (s, 9H), 1.43-1.51 (m, 2H), 1.70-1.80 (m, 2H), 1.88-1.92 (m, 2H), 1.96-2.02 (m, 2H), 3.29-3.38 (m, 2H), 4.52 (s, 2H), 6.96 (d, J=2.2 Hz, 1H), 7.01 (d, J=2.0 Hz, 1H), 7.25 (d, J=2.0 Hz, 1H), 7.31 (d, J=2.4 Hz, 1H), 8.28 (s, 1 H), 8.29 (s, 1H), 13.68 (s br, 1H), 13.97 (s br, 1H). $^{13}$C{$^1$H}NMR (100 MHz, CDCl$_3$): δ=24.5, 24.6, 29.5, 29.6, 31.6, 33.3, 33.4, 34.2, 35.0, 35.2, 65.6, 72.60, 72.61, 118.0, 118.5, 126.2, 127.0, 129.0 (2 overlapping lines), 130.1, 136.6, 137.7, 140.1, 158.1, 160.3, 165.5, 166.1. MS (EI): m/z ($I_{rel}$)=520 (100, M$^+$). Anal. Calcd for C$_{33}$H$_{48}$N$_2$O$_3$: C, 76.11; H, 9.29; N, 5.38. found: C, 76.19; H, 9.51; N, 5.07.

(R,R)-N-(3,5-Di-tert-butylsalicylidene)-N'-[3-tert-butyl-5-(2'-hydroxyethoxymethyl)salicylidene]-1,2-cyclohexanediamine (4e)(Scheme 2)

(R,R)-1,2-Diaminocyclohexane mono(hydrogen chloride) (276 mg, 1.83 mmol), 3,5-di-tert-butyl-2-hydroxybenzaldehyde (460 mg, 1.83 mmol), and 4 Å molecular sieves (200 mg) were charged into a 50 mL flask equipped with a magnetic stir bar and a septum. Anhydrous ethanol (5 mL) and anhydrous methanol (5 mL) were added and the bright yellow solution was stirred at room temperature for four hours.

A solution of 3-tert-butyl-2-hydroxy-5-(2'-hydroxyethoxymethyl)benzaldehyde (460 mg, 1.83 mmol) in anhydrous CH$_2$Cl$_2$ (10 mL) and anhydrous NEt$_3$ (0.51 mL, 3.66 mmol) were added. The red solution was stirred at room temperature for additional four hours. The reaction mixture was filtered through a short pad of dry silica gel and the silica gel was flushed with CH$_2$Cl$_2$. The solvent was removed under reduced pressure. The residue was purified by column chromatography on silica gel (ethyl acetate/hexanes=1:3) to afford 4e (725 mg, 70%) as a yellow powder. R$_F$ (SiO$_2$, ethyl acetate/hexanes=1:3)=0.23. [α]$^{20}_D$-262° (c 0.5, DCM) $^1$H NMR (500 MHz, CDCl$_3$): δ=1.24 (s, 9H), 1.41 (s, 9H), 1.42 (s, 9H), 1.43-1.55 (m, 2H), 1.83-1.92 (m, 2H), 1.61-1.81 (m, 2H), 1.93-2.08 (m, 2H), 2.01 (br s), 3.28-3.38 (m, 2H), 3.54 (m, 2H), 3.72 (br s, 2H), 4.40 (s, 2H), 6.98 (d, J=2.3 Hz, 1H), 7.01 (d, J=1.6 Hz, 1H), 7.22 (d, J=1.6 Hz, 1H), 7.31 (d, J=2.3 Hz, 1H), 8.29 (s, 1H), 8.30 (s, 1H), 13.70, (br s, 1H), 14.00 (br s, 1H). $^{13}$C{$^1$H}NMR (125 MHz, CDCl$_3$): δ=24.3, 29.4, 29.5, 31.5, 33.3, 34.2, 34.9, 35.1, 63.0, 71.2, 72.5, 72.6, 73.4, 117.9, 118.4, 126.1, 126.8, 126.9, 129.6, 129.8, 136.5, 137.4, 140.0, 158.1, 160.3, 165.3, 166.0. MS (ESI): m/z (I$_{rel}$)=565 (13, [M+1]$^+$), 349 (48, C$_{20}$H$_{33}$N$_2$O$_3^+$), 331 (100, C$_{21}$H$_{35}$N$_2$O$^+$). HRMS (ESI) calcd for C$_{35}$H$_{53}$N$_2$O$_4$ ([M+1]$^+$): 565.4005. found: 565.4001. Anal. Calcd for C$_{35}$H$_{52}$N$_2$O$_4$ (564.39): C, 74.43; H, 9.28; N, 4.96. found: C, 74.38; H, 9.30; N, 4.85. (R,R)-N-(3,5-Di-tert-butylsalicylidene)-N'-[3-tert-butyl-5-(7'-hydroxy-1',1'-dimethylheptyl)salicylidene]-1,2-cyclohexanedediamine (4f)(Scheme 2)

(R,R)-1,2-Diaminocyclohexane mono(hydrogen chloride) (59 mg, 0.39 mmol), 3,5-di-tert-butyl-2-hydroxybenzaldehyde (92 mg, 0.39 mmol), and 4 Å molecular sieves (200 mg) were charged into a 25 mL flask equipped with a magnetic stir bar and a septum. Anhydrous methanol (5 mL) was added and the bright yellow solution was stirred at room temperature for four hours. A solution of 3-tert-butyl-2-hydroxy-5-(7'-hydroxy-1',1'-dimethylheptyl)benzaldehyde (125 mg, 0.39 mmol) in anhydrous CH$_2$Cl$_2$ (10 mL) and anhydrous NEt$_3$ (0.15 mL, 0.90 mmol) were added. The red solution was stirred at room temperature for additional four hours. The reaction mixture was filtered through a short pad of dry silica gel and the silica gel was flushed with ethyl acetate. The solvent was removed under reduced pressure. The residue was purified by column chromatography on silica gel (ethyl acetate/hexanes=1:3) to afford 4f (208 mg, 84%) as a bright yellow powder. [α]$^{20}_D$-200° (c 0.5, DCM). $^1$H NMR (300 MHz, CDCl$_3$): δ=1.00-1.15 (m, 2H), 1.16-1.31 (m, 2H), 1.25 (s, 6H), 1.23 (s, 9H), 1.28 (s, 9H), 1.42 (s, 9H), 1.43-1.59 (m, 6H), 1.70-1.80 (m, 2H), 1.88-1.92 (m, 2H), 1.93-2.08 (m, 4H), 2.01 (s, 1H), 3.29-3.38 (m, 2H), 3.54 (t, 2H), 6.98 (d, J=2.2 Hz, 1H), 7.01 (d, J=1.8 Hz, 1H), 7.25 (d, J=2.0 Hz, 1H), 7.31 (d, J=2.4 Hz, 1H), 8.29 (s, 1H), 8.31 (s, 1H), 13.71 (s br, 2 H). $^{13}$C{$^1$H}NMR (125 MHz, CDCl$_3$): δ=24.6, 24.8, 25.7, 29.1, 29.2, 29.3, 29.6, 29.7, 30.3, 31.6, 31.7, 33.0, 33.4, 33.5, 33.6, 34.3, 35.2, 37.2, 44.6, 63.2, 72.6, 76.8, 77.3, 77.7, 118.1, 126.2, 126.9, 127.0, 136.5, 136.6, 138.7, 140.1, 158.1, 158.2, 165.9, 166.0, 166.1, 220.2. MS (ESI): m/z (I$_{rel}$)=635.6 (13, [M$^+$1]+). HRMS (ESI) calcd for C$_{41}$H$_{64}$N$_2$O$_3$ ([M+1]$^+$): 633.4996. found: 633.4995. Anal. Calcd for C$_{41}$H$_{64}$N$_2$O$_3$ (633.49): C, 77.80; H, 10.19; N, 4.43. found: C, 77.88; H, 10.20; N, 4.39.

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

Example 1

(R,R)-N-(3,5-Di-tert-butylsalicylidene)-N'-(3-(4'-vinylbenzene)-5-tert-butylsalicylidene)-1,2-cyclohexanedediamine (1)(4c of Scheme 2)

To a 500 mL flask was charged with (1R,2R)-1,2-diaminocyclohexane monohydrochloride salt (1.51 g, 10 mmol), activated 4 A molecular sieve (4.0 g), anhydrous methanol (40 mL) and ethanol (40 mL). 3,5-Di-t-butyl-2-hydroxybenzaldehyde (2.34 g, 10 mmol) was added in one portion and the reaction mixture was stirred at rt for 4 h. TLC showed that all the aldehyde was consumed. A solution of 3-(4'-vinylphenyl)-5-t-butyl-2-hydroxybenzaldehyde (2.74 g, 10 mmol) in dichloromethane (80 mL) was added to reaction system, followed by the addition of triethylamine (2.8 mL, 20 mmol) in a dropwise fashion. After the reaction mixture was stirred at rt for additional 4 h, all the solvents were removed by rotovap. The residue was dissolved in dichloromethane (100 mL), washed with aqueous hydrochloric acid (1 M, 50 mL) and water (2×50 mL), and dried with magnesium sulfate. The desired compound 1 (5.05 g, 85.2%) was isolated by flash chromatography of the crude product with 1/50 ether/hexanes.

Example 2

Polymerization of (R,R)-N-(3,5-Di-tert-butylsalicylidene)-N'-(3-(4'-vinylbenzene)-5-tert-butylsalicylidene)-1,2-cyclohexanediamine (Scheme 7)

The monomer 1 (237 mg, 0.40 mmol) of Example 1 and AIBN (2.5 mol %, 1.7 mg, 0.010 mmol) were charged into a Schlenk tube. The system was purged with argon for three times. Under the protection of positive pressure of argon, degassed chlorobenzene (2 mL) was added to the system. The reaction mixture was stirred at 80° C. for 48 h. After it was cooled to rt, the solution was poured in to methanol (20 mL) and a yellow solid precipitated. The solid was collected by filtration and washed with 1/20 dichloromethane/methanol (3×10 mL). It was dissolved in dichloromethane (2 mL) and reprecipitated with methanol (20 mL). The solid was collected on a frit, washed with methanol (10 mL), and dried under high vacuum to afford the desired polymer 4 as a yellow powder (201 mg, 85%). Using a similar procedure, homopolymers (2,3) and copolymers (5-7) with styrene were synthesized with different chain lengths and ratios of monomers.

Example 3

Metalation of Polymers with Cobalt(II) Acetate (Scheme 8)

The reaction was carried out in a glove box and solvents were degassed prior to use. The polymer 4 (95 mg, 0.16 mmol) was dissolved in dichloromethane (2 mL) in a vial charged with a stir bar. A solution of cobalt acetate tetrahydrate (49.8 mg, 0.20 mmol) in methanol (2 mL) was added slowly to the vial, resulting in precipitation of a red-brown powder. After the suspension was stirred at rt for 3 h, additional methanol (6 mL) was added to precipitate more solid. The solid was collected by filtration, washed with 1/10 dichloromethane/methanol (2×10 mL) and methanol (10 mL), and dried under high vacuum to give the desired product

Example 4

Preparation of Norbornene Linked Ligands: 5-(4-Hydroxyphenyl ethinyl)-3-tert-butyl-2-hydroxybenzaldehyde, 6 (Scheme 3; 4a of Scheme 2)

An in-vacuo flame-dried 100 mL Schlenk-flask under argon, equipped with a magnetic stir bar and a septum was charged with 1.714 g 4-iodophenol (7.79 mmol, 1.0 eq.), 278 mg [PdCl$_2$(PPh$_3$)$_2$] (0.397 mmol, 5 mol-%) and 51 mg triphenylphosphine (0.195 mmol, 2.5 mol-%). The flask was evacuated and subsequently flushed with Ar. After the evacuating-flushing procedure had been repeated twice, 10 mL of anhydrous THF, a solution of 1.576 g 5-ethinyl-3-tert-butyl-2-hydroxybenzaldehyde 23 (7.79 mmol, 1.0 eq.) in 15 mL anhydrous THF and 2.2 mL of NEt$_3$ (1.58 g, 15.54 mmol, 2.0 eq.) were added via a syringe, respectively, and the slurry was stirred at room temperature for 20 minutes. 28 mg CuI (0.117 mmol, 1.5 mol %) were added and the dark red solution was stirred at room temperature for 27 hours. The mixture was diluted with 100 mL H$_2$O and 50 mL Et$_2$O and the phases were separated. The aqueous layer was extracted with Et$_2$O (2×50 mL), the combined organic layers were washed with brine (40 mL) and dried over MgSO$_4$. After removal of the solvent under reduced pressure, 4.16 g of the crude product were obtained as a red oil. Purification by column chromatography (SiO$_2$, 4×58 cm$^2$, ethyl acetate/hexanes=1:7) yielded 1.224 g product (51%) as yellow powder. $^1$H-NMR (500 MHz, CDCl$_3$/CD$_2$Cl$_2$): δ=1.41 (s), 5.19 (br. s.), 6.80 (d), 7.40 (d), 7.57 (d), 7.63 (dd), 9.84 (br. s.), 11.88 (dd). $^{13}$C-NMR (125 MHz, CDCl$_3$/CD$_2$Cl$_2$): δ=29.0, 35.0, 86.9, 88.1, 114.6, 115.4, 115.6, 120.5, 133.2, 134.9, 137.0, 138.8, 155.9, 161.0, 196.9. HRMS (ESI): calcd for C$_{19}$H$_{18}$O$_3$: 294.1256, obsd 295.1341 [M+1]$^+$. Anal. Calcd. for C$_{19}$H$_{18}$O$_3$: C, 77.53, H, 6.16; O, 16.31. Found: C, 77.20; H, 6.37; O, 16.27.

Salen Linker Compound 7 (Scheme 3). Under an argon atmosphere in a flame-dried 25 mL three-necked flask, equipped with a magnetic stir bar, a septum and a gas-inlet, 301 mg (R,R)-1,2-diaminocyclohexane-mono-aminochloride 3 (2 mmol, 1.0 eq.) and some 4 Å molecular sieve were slurried up in 7 mL anhydrous ethanol and 7 mL anhydrous methanol. To this slurry, 487 mg 5-(4-hydroxyphenyl ethinyl)-3-tert-butyl-2-hydroxy-benzaldehyde 6 (2 mmol, 1.0 eq.) was added. The bright yellow solution was stirred at room temperature. After four hours, a solution of 589 mg 3,5-di-tert-butyl-2-hydroxybenzaldehyde 4 (2 mmol, 1.0 eq.) in 15 mL anhydrous CH$_2$Cl$_2$ and 0.56 mL anhydrous NEt$_3$ (4 mmol, 2.0 eq.) were added. The red solution was stirred at room temperature for an additional four hours. The mixture was filtered, the solvent removed under reduced pressure and the residue purified by column chromatography (dry SiO$_2$, 2.5×40 cm$^2$, ethyl acetate/hexanes=1:5). 910 mg of the product (64%) could be isolated as a yellow-orange powder. $^1$H-NMR (500 MHz, CDCl$_3$/CD$_2$Cl$_2$): δ=1.26 (s), 1.44 (s), 1.46 (s), 1.40-1.53 (m), 1.82-1.93 (m), 1.66-1.81 (m), 1.93-2.05 (m), 3.25-3.77 (m), 6.81 (d), 7.00 (d), 7.19 (d), 7.35 (d), 7.40 (d), 7.41 (d), 8.22 (s), 8.28 (s). $^{13}$C-NMR (125 MHz, CDCl$_3$/CD$_2$Cl$_2$): δ=24.4, 29.4, 29.6, 31.5, 33.1, 33.2, 35.0, 34.2, 35.1, 72.0, 72.2, 87.2, 88.3, 112.5, 115.7, 115.7, 117.7, 118.8, 126.1, 127.3, 132.7, 133.2, 133.3, 136.7, 137.9, 140.1, 155.7, 158.4, 161.5, 165.2, 166.2. MS (ESI) m/z (%): 607.3888 (±0.025) (56, [M+1]$^+$), 391.2 (C$_{25}$H$_{31}$N$_2$O$_2$, 100), 331.3 (C$_{21}$H$_{35}$N$_2$O, 72). Anal. Calcd. for C$_{40}$H$_{50}$N$_2$O$_3$: C, 79.17; H, 8.30; N, 4.62; O, 7.91. Found: C, 78.61; H, 8.26; N, 4.63; O, 8.06.

Salen-Norbornene Compound (Scheme 3). Under an argon atmosphere, 720 mg salen linker compound 7 (1.186 mmol, 1.0 eq.) was dissolved in 20 mL anhydrous CH$_2$Cl$_2$ in a dry 50 mL Schlenk-flask, equipped with a magnetic stir bar and a septum. The red solution was cooled to 0° C. A solution of 204 mg norbornene carbonyl chloride 8 (1.31 mmol, 1.1 eq.) in 8 mL anhydrous CH$_2$Cl$_2$ and 0.18 mL anhydrous NEt$_3$ (1.31 mmol, 1.1 eq.) were added dropwise via a syringe, respectively. The yellow solution was stirred at 0° C. for 30 minutes and was then allowed to warm up to room temperature over a period of 30 minutes. The reaction mixture was filtered through a pad of dry silica and the silica was flushed with CH$_2$Cl$_2$. After removal of the solvent under reduced pressure, 913 mg product (96%) were obtained as a yellow solid. Usually, the crude product was used in the following steps. For characterization purposes, a part of the norbornene was purified by column chromatography (dry SiO$_2$, Et$_2$O/hexanes=1:10). $^1$H-NMR (500 MHz, CDCl$_3$/CD$_2$Cl$_2$): δ=1.24 (s), 1.42 (s), 1.43 (s), 1.35-1.39 (m), 1.45-1.50 (m), 1.83-1.94 (m), 1.50-1.64 (m), 1.68-1.82 (m), 1.94-2.01 (m), 2.01-2.10 (m), 2.97-3.02 (m), 3.19-3.25 (m), 3.22-3.37 (m), 3.37-3.41 (m), 6.09 (dd), 6.28 (dd), 6.18 (dd), 6.21 (dd), 6.96 (d), 7.01 (d), 7.08 (d), 7.19 (d), 7.32 (d), 7.39 (d), 7.47 (d), 7.80 (d), 8.25 (s), 8.28 (s), 13.62 (br. s.), 14.28 (br. s.). $^{13}$C-NMR (125 MHz, CDCl$_3$/CD$_2$Cl$_2$): δ=24.4, 29.3, 29.6, 29.5, 30.7, 31.6, 33.1, 33.3, 34.2, 35.0, 35.1, 41.9, 42.8, 43.5, 43.8, 46.1, 46.5, 46.9, 49.9, 72.4, 72.5, 86.7, 89.7, 112.2, 117.8, 118.6, 121.2, 121.7, 126.0, 127.1, 132.3, 132.6, 132.7, 133.4, 135.8, 136.6, 137.9, 138.4, 140.2, 150.5, 158.0, 161.3, 165.1, 166.2, 173.2. MS (ESI) m/z (%): 727.5 (100, [M+1]$^+$), 525.4 (19). Anal. Calcd. for C$_{40}$H$_{58}$N$_2$O$_4$: C, 79.30; H, 8.04; N, 3.85; O, 8.80. Found: C, 79.07; H, 8.06; N, 3.79; O, 8.86.

Mn-Salen-Norbornene Compound 9 (Scheme 3). Under an argon atmosphere, an in-vacuo flame-dried 100 mL three-necked flask, equipped with a magnetic stir bar, a septum, an addition funnel and a reflux-condenser with gas-inlet, was charged with 923 mg Mn(OAc)$_2$.4H$_2$O (3.77 mmol, 3.0 eq.) and 15 mL anhydrous ethanol. The white slurry was heated to reflux (90° C. oil bath temperature) and a solution of 913 mg salen-norbornene (1.26 mmol, 1.0 eq.) in 15 mL anhydrous toluene was filled into the addition funnel. The ligand-solution was added dropwise to the manganese solution and the addition funnel was washed with anhydrous ethanol (2×5 mL). The reaction mixture was heated under reflux for two hours. Then, a needle connected to an air cylinder was placed in the solution through the septum, air was slowly bubbled through the refluxing mixture and the conversion of the ligand was monitored by TLC-analysis of the red solution. After one hour, TLC-analysis indicated complete conversion of the free ligand. Then, 160 mg lithium chloride (3.77 mmol, 3.0 eq.) was added and the mixture was allowed to cool down to room temperature over a period of one hour. The mixture was transferred into a separatory funnel and the toluene layer was washed with H$_2$O (3×50 mL) and brine (50 mL) and dried over MgSO$_4$. After removal of the solvent under reduced pressure, 1.93 g crude product were obtained as a dark red oil. Purification by column chromatography (dry SiO$_2$, 4×30 cm$^2$, CH$_2$Cl$_2$->CH$_2$Cl$_2$/ethyl acetate=5:1) yielded 813 mg product (79%) as a dark red solid. MS (ESI) m/z (%): 779.35 (100, [M-Cl]$^+$). Anal. Calcd. for C$_{40}$H$_{56}$ClMnN$_2$O$_3$: C, 70.71; H, 6.92; N, 3.44. Found: C, 70.34; H, 7.11; N, 3.37.

Example 5

Poly(Mn-salen-norbornene), p(9) (where "p" Refers to a Polymer of Compound "9") (Synthesis of a 50-mer) (Scheme 5)

In an in-vacuo flame-dried 50 mL three-necked flask equipped with a magnetic stir bar, a septum and a reflux-condenser with gas-inlet, 122 mg Mn-salen-norbornene 9 (150 μmol, 50 eq.) was dissolved in 3 mL anhydrous $CDCl_3$ and the solution was heated to 40° C. 2.7 mg Grubbs-catalyst (3°-generation) (3 μmol, 1 eq.) was added as a solid and the mixture was stirred for 2.5 hours at 40° C. The polymerization was quenched by adding three drops of ethyl vinyl ether and the polymer was precipitated by adding 30 mL of $Et_2O$. The polymer was separated by centrifugation and washed with $Et_2O$ three times (the polymer was suspended in $Et_2O$ and subsequently separated by centrifugation). After drying the residue in vacuo, 96 mg (79%) of an ether-insoluble polymer-fraction were obtained as a dark, red-brown powder. Anal. Calcd. for $C_{40}H_{56}ClMnN_2O_3$: C, 70.71; H, 6.92; N, 3.44; O, 7.85. Found: C, 68.67; H, 7.02; N, 3.27; O, 9.09. ICP: calcd: Mn, 6.74. Found: Mn, 5.00.

Example 6

Poly(Mn-salen-norbornene-co-n-octyl-norbornenecarbonyl ester), p(9.11) (where "p" Refers to Copolymer of "9.11") (x/y=1:1, x+y=50) (Scheme 5)

In an in vacuo flame-dried 25 mL three-necked flask under Ar, equipped with a magnetic stir bar, a septum and a reflux-condenser with gas-inlet, 79 mg Mn-salen-norbornene 9 (94 μmol, 25 eq.) and 24 mg n-octyl-norbornenecarbonyl ester 11 (94 μmol, 25 eq.) were dissolved in 4 mL anhydrous $CDCl_3$. Then, 3.3 mg Grubbs-catalyst (3°-generation) (3.75 μmol, 1 eq.) were added as a solid and the mixture was stirred at room temperature. After 20 minutes, TLC-analysis as well as analysis of an aliquot by $^1$H-NMR spectroscopy indicated complete conversion of both monomers. The polymerization was quenched by adding two drops of ethyl vinyl ether and the polymer was precipitated by adding 20 mL of $Et_2O$. After separation of the solid by centrifugation and drying in vacuo, 82 mg (82%) of an ether-insoluble polymer-fraction was obtained as a dark, red-brown powder. Anal. Calcd.: C, 72.13; H, 7.78; N, 2.63; O, 9.01, Cl, 3.33. Found: C, 71.10; H, 7.65; N, 2.64; O, 9.72, Cl, 2.26. ICP: calcd: Mn, 5.15. Found: Mn, 4.68.

Example 7

Co-Salen-Norbornene, 10 (Scheme 5)

In an in vacuo flame-dried 10 mL Schlenk-flask under Ar, equipped with a magnetic stir bar and a septum, 146 mg salen-norbornene (0.20 mmol, 1.0 eq.) were dissolved in 1.5 mL anhydrous $CH_2Cl_2$. A solution of 60 mg $Co(OAc)_2·4H_2O$ (0.24 mmol, 1.1 eq.) in 2 mL of anhydrous MeOH was added dropwise via a syringe. The resulting red suspension was stirred for 30 min. at room temperature, cooled in a ice-bath and stirred for another 30 min. at 0° C. The orange-red precipitate was separated by vacuum-filtration, washed with cold MeOH and dried in vacuo to yield 121 mg (77%) 10 as an orange-red powder. MS (ESI) m/z (%): 783.3517 (±0.01) (100, $[M]^+$)—calcd.: 783.3572. Anal. Calcd. for $C_{48}H_{56}CoN_2O_4$: C, 73.54; H, 7.20; N, 3.57; O, 7.52. Found: C, 73.33; H, 7.21; N, 3.49; O, 7.64. ICP: calcd: Co, 7.52. Found: Co, 8.00.

Example 8

Poly(Co(II)-salen-norbornene) p(10)' (Synthesis of a 20-mer) (Scheme 5)

In an in vacuo flame-dried 25 mL three-necked flask under Ar, equipped with a magnetic stir bar, a septum and a gas-inlet, 111 mg Co(II)-salen-norbornene 10 (151 μmol, 20 eq.) were dissolved in 10 mL anhydrous $CDCl_3$. Then, 6.7 mg Grubbs-catalyst (3°-generation) (7.5 μmol, 1 eq.) were added as a solid and the mixture was stirred at room temperature. After two hours, analysis of an aliquot by $^1$H-NMR-spectroscopy showed complete conversion of the monomer (absence of monomeric olefin peaks). The polymerization was quenched by adding three drops of ethyl vinyl ether and mixture was poured into 50 mL of cold $Et_2O$. The precipitated polymer was separated by centrifugation and washed with $Et_2O$ (the polymer was suspended in $Et_2O$ and subsequently separated by centrifugation). After drying the residue in vacuo, 105 mg (94%) of an ether-insoluble polymer-fraction were obtained as a dark, red powder. Anal. Calcd. for $C_{48}H_{56}CoN_2O_4$: C, 73.54; H, 7.20; N, 3.57; O, 7.52. Found: C, 71.06; H, 7.06; N, 3.57; O, 8.16. ICP: calcd: Co, 7.52. Found: Co, 6.96.

Example 9

Poly(Co-salen-norbornene-co-n-octyl-norbornenecarbonyl ester) p(10.11) (x/y=1:1, x+y=50) (Scheme 5)

In an in vacuo flame-dried 10 mL Schlenk-flask under Ar, equipped with a magnetic stir bar and a septum, 78 mg Co-salen-norbornene 10 (100 mmol, 25 eq.) and 25 mg n-octyl-norbornenecarbonyl ester 11 (100 mmol, 25 eq.) were dissolved in 5 mL anhydrous $CDCl_3$. Then, 3.5 mg Grubbs-catalyst (3°-generation) (4 mmol, 1 eq.) was added as a solid and the mixture was stirred at room temperature. After 40 minutes, TLC-analysis as well as analysis of an aliquot by $^1$H-NMR spectroscopy indicated complete conversion of both monomers. The polymerization was quenched by adding two drops of ethyl vinyl ether. The solvent was removed under reduced pressure, the residue was redissolved in some $CH_2Cl_2$, and the polymer was precipitated by adding 40 mL of cold $Et_2O$. After separation of the solid by centrifugation and drying in vacuo, 94 mg (91 m-%) of an ether-insoluble polymer-fraction were obtained as a dark, brown powder. Anal. Calcd.: C, 75.11; H, 8.80; N, 7.82; O, 10.42. Found: C, 74.25; H, 8.73; N, 1.95; O, 11.15. ICP: calcd: Co, 3.84. Found: Co, 3.95.

Example 10

Synthesis of the Co-salen-norbornene monomer 10•I (M=Co, L=I)(Scheme 5)

In an in vacuo flame-dried 10 mL Schlenk-flask under Ar, equipped with a magnetic stir bar and a septum, 73 mg salen-norbornene (0.10 mmol, 1.0 eq.) was dissolved in 1 mL in anhydrous $CH_2Cl_2$. A solution of 27 mg $Co(OAc)_2·4H_2O$ (0.11 mmol, 1.1 eq.) in 1 mL anhydrous MeOH was added dropwise via a syringe. The resulting red suspension was stirred for 60 min. at room temperature. TLC-analysis of the reaction mixture showed complete conversion of the ligand to the Co complex. Next, 27 mg iodine $I_2$ (0.2 mmol I, 2.0 eq.) was added as a solid and the dark solution was stirred for another 60 min. at room temperature. The reaction mixture was filtered through a pad of dry silica and the silica was flushed with $CH_2Cl_2$. After removal of the solvent under reduced pressure, the obtained dark powder was purified by column-chromatography over dry silica ($CH_2Cl_2$/ethyl acetate=5:1) to yield 78 mg (86%) 10•I as a dark powder. $R_F$ ($SiO_2$, $Et_2O$/hexanes=1:10)=0. ESI-MS m/z (%): 7. 783.3 (100, $[M-I]^+$)—calcd.: 910.8.

Polymerization of 10•I to
Poly(Co-I-salen-norbornene) p(10b)

In an in vacuo flame-dried 10 mL three-necked flask under Ar, equipped with a magnetic stir bar, a septum and a gas-inlet, 56 mg Co-1-salen-norbornene 10•I (62 micromol, 20 eq.) were dissolved in 2.5 mL anhydrous $CDCl_3$. 2.7 mg Grubbs-catalyst (3°-generation) (3.1 micromol, 1 eq.) were added as a solid and the mixture was stirred at room temperature. After two hours, analysis of an aliquot by $^1$H-NMR-spectroscopy showed complete conversion of the monomer (absent monomeric olefin signals). The polymerization was quenched by adding 3 drops of ethyl vinyl ether and the polymer was precipitated by adding 20 mL of cold $Et_2O$. The precipitated polymer was then separated by centrifugation and washed with $Et_2O$ (i.e., the polymer was suspended in $Et_2O$ and subsequently separated by centrifugation). After drying the residue in vacuo, 35 mg (62 m-%) of an ether-insoluble polymer-fraction were obtained. GPC: $M_n$=43,000, $M_w$=66,100, $M_w/M_n$=1.54.

Example 11

Hydrolytic Kinetic Resolution of Racemic Epichlorohydrin rac-18 with poly(Co(III)(OTs)-salen-norbornene) p(10c)(Scheme 10)

In a vial with a magnetic stir bar, 48.7 mg poly(Co(III) (OTs)-salen-norbornene) p(10c) (50 μmol, 0.5 mol-%) were dissolved in 100 μL chlorobenzene (as an internal standard) and 784 μL epichlorohydrin (10 mmol, 1.0 eq.). After taking an aliquot (2 μL), 126 μL of water (7 mmol, 0.7 eq.) were added. Aliquots (2 μL) were taken after 5, 10, 15, 20, 30, 60, 120 and 180 minutes. All aliquots were filtered through a pipette with cotton and some silica and the silica was flushed with 1.5-2 mL $Et_2O$. The resulting solutions were analyzed via chiral GC-FID (γ-TA). After three hours, the dark mixture was diluted with 2 mL $CH_2Cl_2$ and added drop-wise to cold $Et_2O$ (ca. 40 mL). The resulting precipitate was separated by centrifugation and washed with cold $Et_2O$, i.e., the polymer was suspended in $Et_2O$ and subsequently separated by centrifugation, then dried in vacuo.

Hydrolytic Kinetic Resolution of (rac)-Epichlorohydrin (Scheme 10). The above procedure was repeated with the exception that a Co(II) salen-norbornene was selected as the starting catalyst instead of a Co(III). The precatalyst Co(II) (2-7) (Scheme 8) (25.5 mg, 0.025 mmol) was dissolved in dichloromethane (1 mL) in 10 mL flask. Glacial acetic acid (0.10 mL) was added and the reaction mixture was stirred in the open air for 30 min. The solvent and excess acetic acid were completely removed under high vacuum. To the residue was added epichlorohydrin (391 microliter, 5.0 mmol) and chlorobenzene (50 microliter, internal reference). The flask was immersed in a water bath at rt. Deionized water (0.70 eq., 63 microl, 3.5 mmol) was injected into the system to start the reaction and the reaction process was monitored by means of GC (G-TA column). With a reaction time of 1 h, the conversion and the ee of epichlorohydrin were 55% and >99%, respectively.

Hydrolytic Kinetic Resolution with polymeric Co-OAc-salen complexes p(38) and p(38.29) The above procedure was repeated with the exception that polymeric Co-OAc-salen complexes p(38) and p(38.29) were selected and other conditions or procedural variations as indicated. The catalytic performances of the polymeric cobalt complexes p(38) and p(38.29) prepared as shown in Scheme 6 were studied in the HKR of racemic epichlorohydrin, where dichloromethane was added as a cosolvent due to the insolubility of the copolymers in ECH. The reaction kinetics of the HKR were studied via chiral GC-analysis. Using the homopolymer p(38a), epoxide (R)-36 (R)-epichlorohydrin was fully converted after less than two hours to its corresponding diol, leaving pure (S)-36 in the reaction mixture in above 99% ee. After this time period, 55% of the racemic 36 is converted, showing that p(38a) with the flexible ethylene glycol linker is more active than its analogue p(28a) with a rigid phenylene acetylene linker (>99% ee, 55% conv. after five hours, while the selectivity is comparable. In contrast to the results with the copolymers of 28, the activity of p(38a-co-29) decreases with increasing dilution (i.e., decreased content of copolymerized monomer compound of formula (I)) of the catalytic centers along the polymer chain. With p(38a-co-29)$_{13}$ it took three hours to obtain (S)-36 with >99% ee (54% conv.), while with p(38a-co-29)$_{19}$ a complete conversion of rac-36 could not even be achieved after 40 hours (49% conv., 92% ee). These results reflect the expectations for a cooperative bimetallic mechanism for the HKR and can thus be interpreted as confirmation of this mechanism.

Under solvent-free condition of the HKR, p(38a) was not only more active but also more selective than its analog with a rigid linker p(28a). Using the polymeric catalyst p(38a), (S)-36 with >99% ee was obtained after only 30 minutes and with 54% conversion of the rac-36 (p(28a): two hours, 62% conv.). Moreover, activity and selectivity of p(38a) were also higher than of the corresponding monomer 38a (complete resolution after two hours and 56% conv. of rac-36), indicating a positive polymer effect by an easier (intramolecular) interaction of two cobalt moieties in p(38a).

Comparisons of the reaction rates for the degradation of the (R)-epoxide 36 reveals that the rate of the monomer 38a was comparable to those of 28a and p(28a) and slightly faster than for a Jacobsen catalyst, indicating that (i) slight diversity of structures 28a and 38a to that of the Jacobsen Co-salen are responsible for the different rates, and (ii) that the polymerization of 28a did not result in a more active catalyst. In contrast to the similar activities of 28a and p(28a), the resolution rate with p(38a) is significantly higher than for monomer 38a (according to the slopes by a factor of around two). Because the salen cores of 38a and p(38a) have exactly the same structure, this increase can only be a result of a better intramolecular interaction of two cobalt centers in the polymer.

The activity differences between monomeric and polymeric 38a as well as between p(38a) and p(28a), that only differ in the linker flexibility, confirm the assumed bimetallic mechanism for the HKR. Moreover, the comparison of the catalytic performances of p(28a) and p(38a) shows that for polymer-supported catalysts for reactions, such as the HKR, where the interaction of two catalytic centers is significant for high performance, the use of flexible linkers and homopolymer-supports is preferred if not compulsory.

Because of the high activity of p(38a) the concentration of cobalt can be reduced from 0.5 mol-% to up to 0.01 mol-%, whereby only the resolution rate but not the selectivity was affected. When the cobalt amount was decreased from 0.5 mol-% to 0.1 mol-% the reaction time for obtaining (S)-36 with >99% ee increased from 30 minutes to five hours (54% conv. of rac-36 in both cases). A further reduction of the Co-concentration to 0.01 mol-% resulted in an even slower HKR. Nevertheless, after 46 hours, 53% of the racemic epichlorohydrin is converted and (S)-36 with 99% ee is obtained, showing that even with a low concentration of p(38a) complete resolution is feasible.

The removal and recycling properties of p(38a) are comparable those of p(28a). The polymeric Co-complexes could be separated easily from the reaction mixtures by precipitation into $Et_2O$ and subsequent centrifugation. After reoxidation with $O_2$/HOAc, the resolution rate of the recycled p(38a) is somewhat less than that of the original polymer and comparable to Jacobsen's cobalt-salen catalyst. The HKR was complete after three hours with 57% conversion of rac-36, showing that selectivity of the catalyst also decreased slightly upon reuse. In the third cycle the polymeric catalyst was not fully soluble in the reaction mixture any more, even after adding $CH_2Cl_2$ as a co-solvent, and the reaction rate dropped significantly. However, after 14 hours (S)-36 with 98% ee was obtained (55% conv. of rac-36), indicating that the polymeric catalyst was still active and very selective and that after an appropriate reaction time enantiomerically pure (S)-36 could be isolated in good yields. Because of the solubility problems after precipitation and reoxidation of p(38a) and experience reusing p(28a) after pumping-off the substrates, the latter methodology was used to recycle p(38a), using $CH_2Cl_2$ as a solvent. Although the solubility issues after recycling could be circumvented this way, activities and selectivities of the reused catalysts p(38a) decreased in each cycle. While the resolution in the first cycle was complete after two hours (55% conv.), it took about 16 hours and almost 66% conversion of rac-36 in the second cycle. In the third cycle, only 30% rac-36 were converted after 23 hours (37% ee of (S)-36), showing that p(38a) is not recyclable this way in contrast to p(28a).

Example 12

Asymmetric Epoxidation of 1,2-dihydronaphthalene 14 with poly(Mn-salen-norbornene) p(9) of Scheme 5 (Scheme 11)

Under an argon atmosphere in a dry 10 mL Schlenk-flask, 13 mg poly(Mn-salen-norbornene) p(9) (16 μmol, 4 mol-%) and 234 mg N-methylmorpholine-N-oxide (NMO) (2 mmol, 5.0 eq.) were dissolved in 2 mL of anhydrous $CH_2Cl_2$. Then, 52 μL 1,2-dihydronaphthalene 14 (52 mg, 0.4 mmol, 1.0 eq.) and ca. 0.04 mL chlorobenzene as an internal standard were added via a microsyringe, respectively, and the solution was cooled to −20° C. 138 mg meta-chloroperoxybenzoic acid (mCPBA) (0.8 mmol, 2.0 eq.) were added in three equal portions at t=0, 60, 120 sec. Aliquots (ca. 0.2 mL) were taken after 0, 30, 90, 150, 210 and 300 seconds. All aliquots were filtered through a pipette with cotton and some $Al_2O_3$ and the $Al_2O_3$ was flushed with ca. 1.5 mL $CH_2Cl_2$. The resulting solutions were analyzed via chiral GC-FID (HP-5). The aliquots at t=210 sec. and t=300 sec. were also analyzed by chiral GC-MS (β-CD).

Example 13

Recycling and reoxidation of the cobalt-polymers. Polymeric Co-complexes were separated from the reaction mixtures by precipitation into $Et_2O$ and subsequent centrifugation. The residue obtained after centrifugation was dissolved in $CH_2Cl_2$, 9.5 mg para-toluenesulfonic acid monohydrate (50 mmol, 1.0 eq. according to Co) was added and the mixture was stirred under an atmosphere of air for one hour. The $CH_2Cl_2$-solution was added dropwise to cold $Et_2O$ (ca. 40 mL), the precipitate separated by centrifugation and "washed" with cold $Et_2O$. The obtained residue was dried in vacuo to yield 45 mg (93%) of re-oxidized p(10c)_rec as a dark green powder. The polymeric catalysts could be recovered quantitatively. For example for CoOAc-salen complex p(10a), we started with 23 mg for the first catalytic cycle, and obtained 24 mg after recycling and reoxidation in the second cycle and also 24 mg for the third cycle. This data clearly proves that the polymer was recycled quantitatively.

The disclosure has been described with reference to various specific embodiments and techniques. However, it should be understood that many variations and modifications are possible while remaining within the spirit and scope of the disclosure.

The claimed invention is:

1. A compound selected from the group consisting of

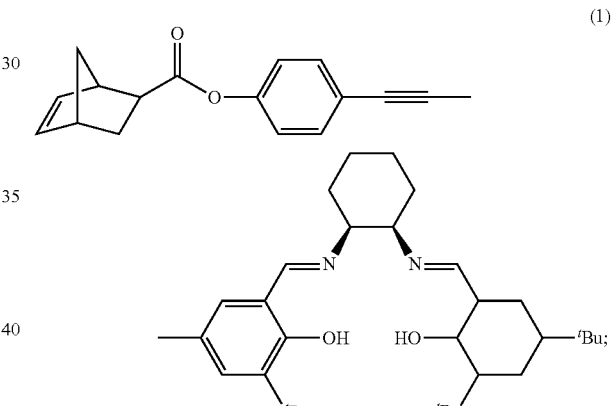

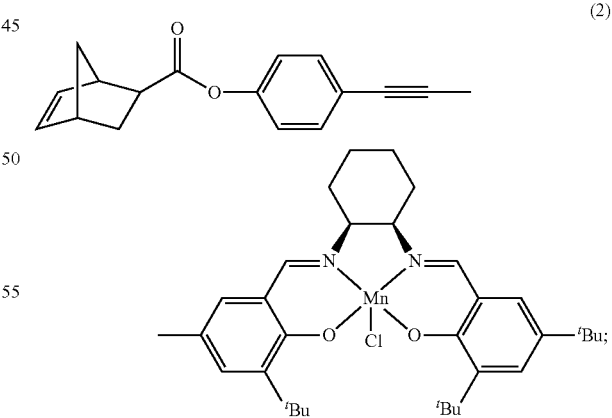

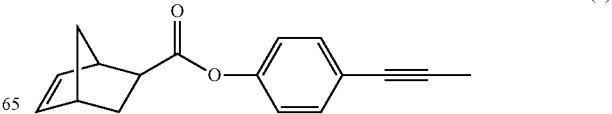

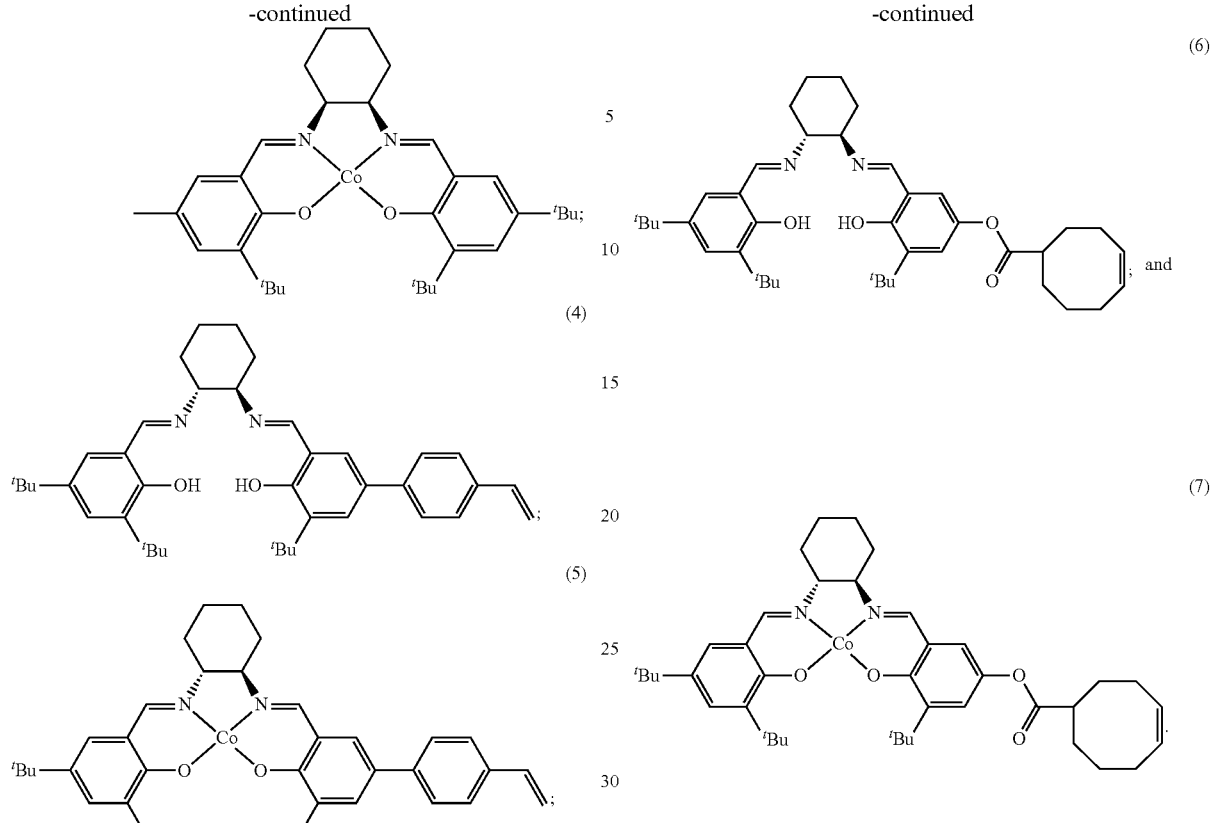
2. The compound of claim 1 having the structure represented by formula (1):
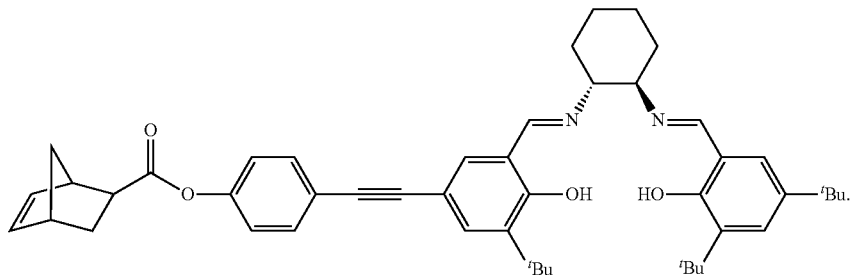
3. The compound of claim 1 selected from the group consisting of:
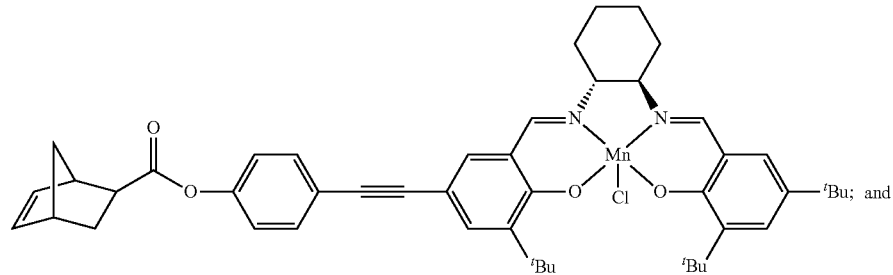

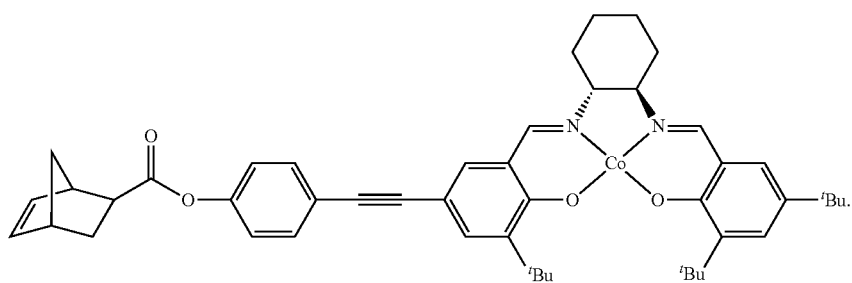

4. The compound of claim 1 having the structure represented by formula (4)

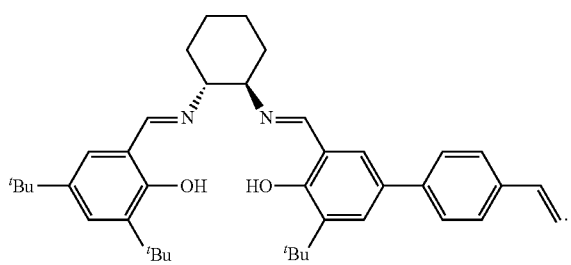

5. The compound of claim 1 having the structure represented by formula (5)

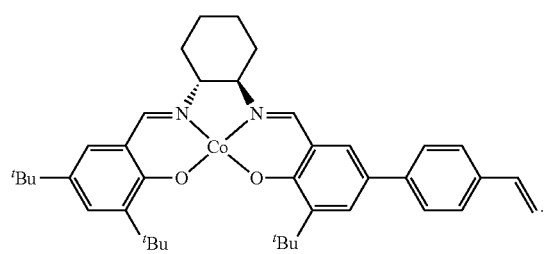

6. The compound of claim 1 having the structure represented by formula (6)

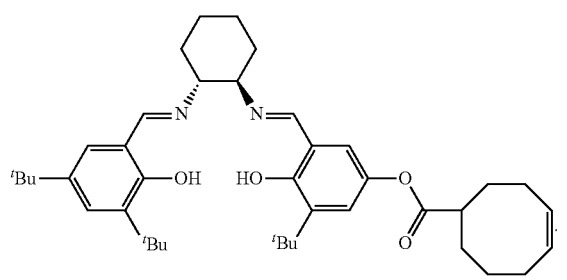

7. The compound of claim 1 having the structure represented by formula (7)

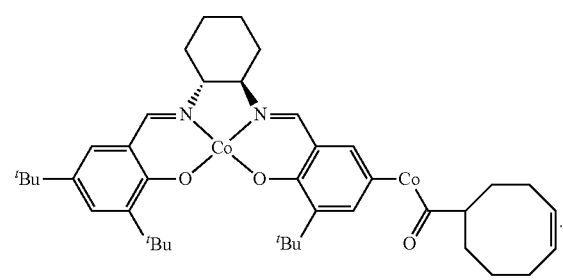

8. A process for preparing the compound of claim 2, which comprises:

a) reacting a salicylaldehyde (8)

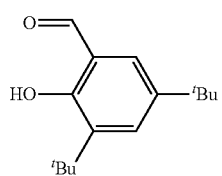

with an (1R,2R)-amino-ammonium cyclohexyl chloride (9)

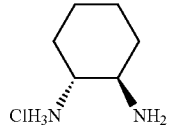

to obtain a compound (10)

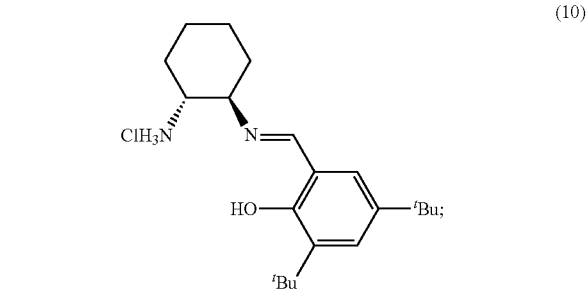

b) reacting a compound (10) in the presence of Et₃N with compound (11) and
c) reacting compound (12) with compound (13)
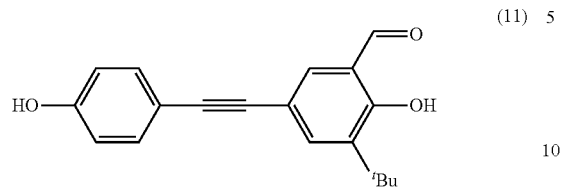
to obtain compound (12);
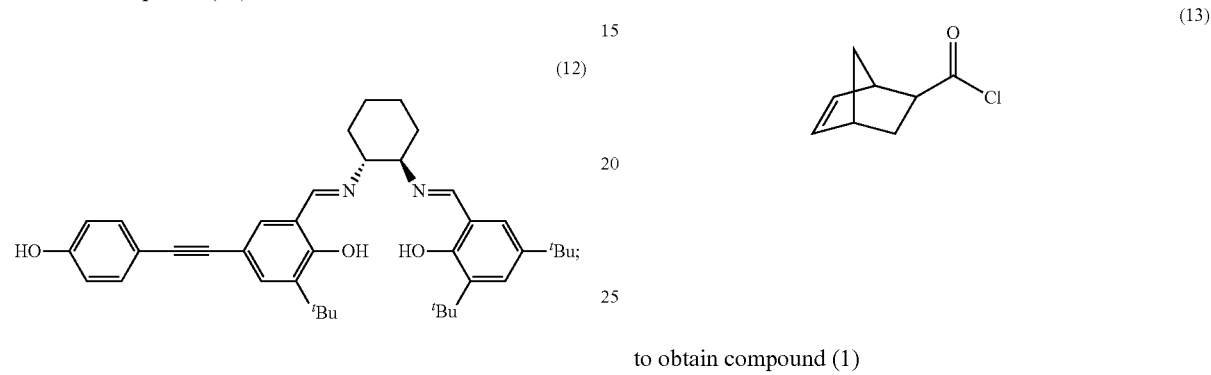
to obtain compound (1)
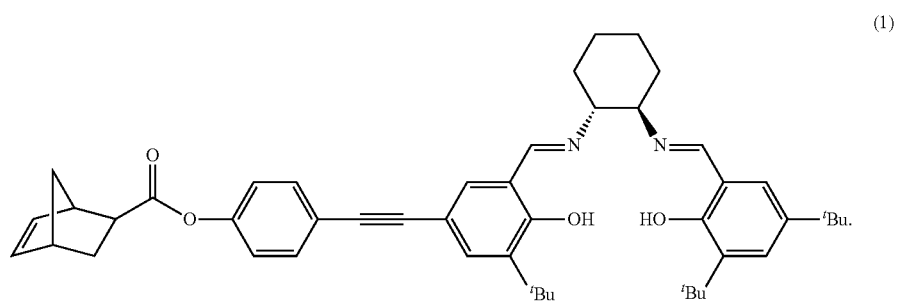
9. The process of claim 8, which further comprises:
d) reacting compound (1) with Mn(OAc)₂ and then LiCl to obtain compound (2)
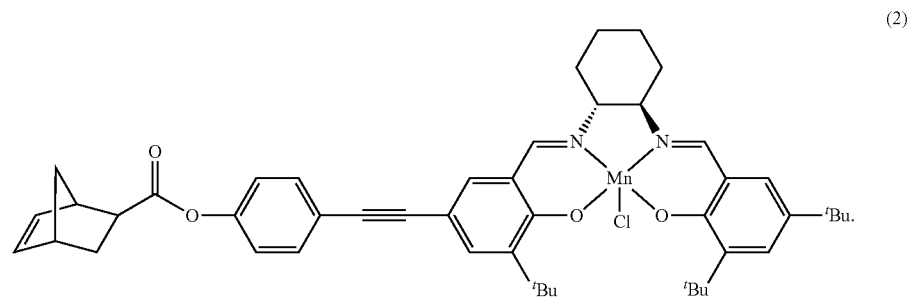

10. The process of claim 8, which further comprises:

d) reacting compound (1) with Co(OAc)$_2$ to obtain compound (3)

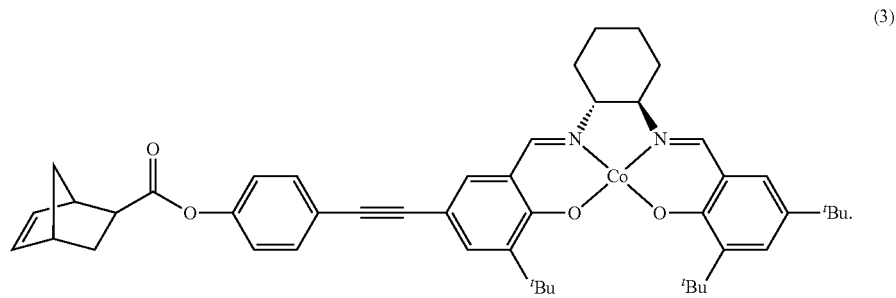

(3)

11. A process for preparing the compound of claim 4, which comprises:

a) reacting a salicylaldehyde (8)

(8)

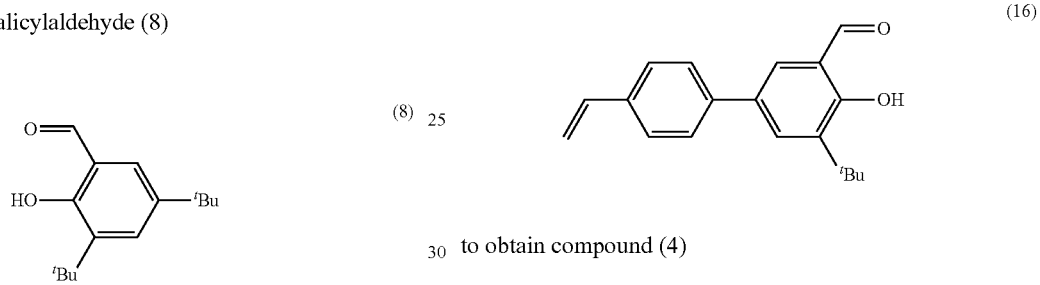

(16)

to obtain compound (4)

with an (R,R)-amino-ammonium cyclohexyl chloride (14)

(14)

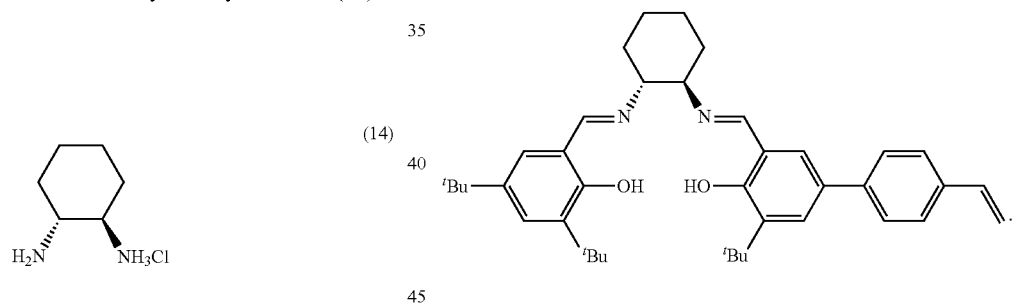

(4)

to obtain a compound (15)

(15)

12. The process of claim 11, which further comprises:

d) reacting compound (4) with Co(OAc)$_2$ to obtain compound (5)

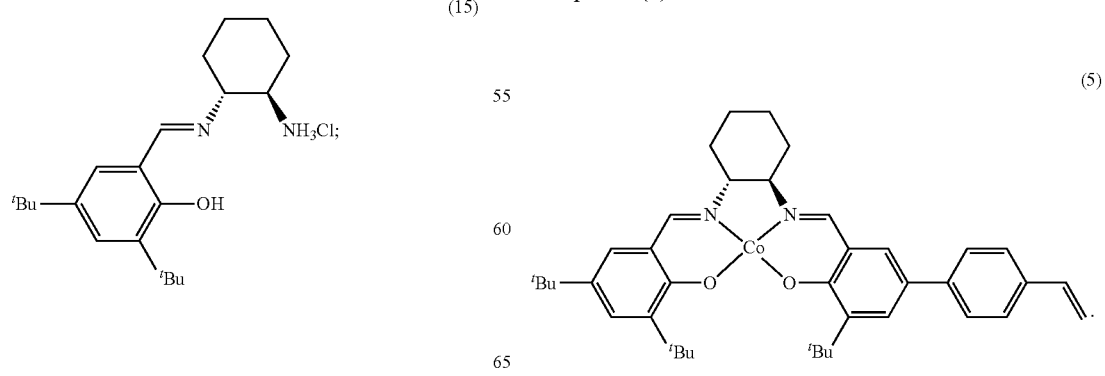

(5)

and b) reacting compound (15) in the presence of Et$_3$N and a compound (16)

13. A process for preparing the compound of claim 6, which comprises:
a) reacting a salicylaldehyde (8)
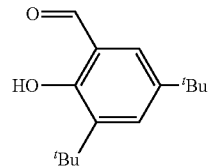
(8)
with an (R,R)-amino-ammonium cyclohexyl chloride (14)
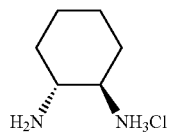
(14)
to obtain a compound (15)
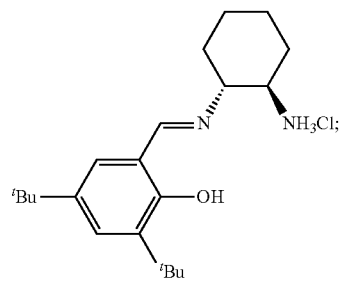
(15)
and
b) reacting a compound (15) in the presence of Et₃N and a compound (17)
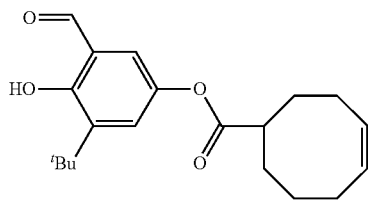
(17)
to obtain compound (6)
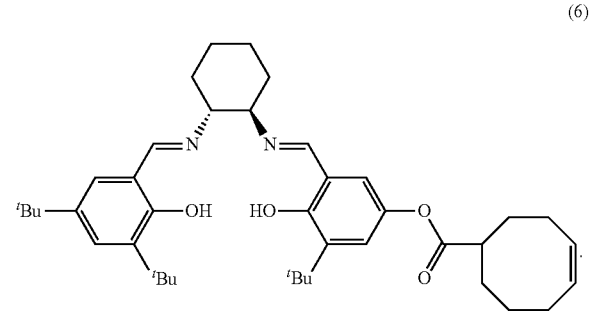
(6)
14. The process of claim 13, which further comprises:
d) reacting compound (6) with Co(OAc)₂ to obtain compound (7)
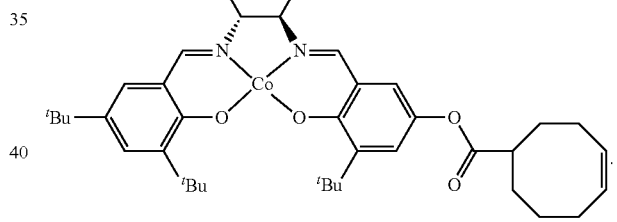
* * * * *